United States Patent
Sidhu et al.

(10) Patent No.: US 10,697,963 B2
(45) Date of Patent: Jun. 30, 2020

(54) NUCLEIC ACIDS ENCODING ANTIBODIES WITH HIGH AFFINITY FOR ALPHA-KLOTHO

(71) Applicants: The Governing Council of the University of Toronto, Toronto (CA); Board of Regents, The University of Texas System, Austin, TX (US)

(72) Inventors: Sachdev S. Sidhu, Toronto (CA); Sarah L. Barker, Toronto (CA); Orson W. Moe, Dallas, TX (US); Makoto Kuro-o, Dallas, TX (US)

(73) Assignees: The Governing Council of the University of Toronto, Toronto (CA); Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 16/261,141

(22) Filed: Jan. 29, 2019

(65) Prior Publication Data

US 2019/0145976 A1     May 16, 2019

Related U.S. Application Data

(62) Division of application No. 15/500,478, filed as application No. PCT/CA2015/050728 on Jul. 31, 2015, now Pat. No. 10,228,374.

(60) Provisional application No. 62/031,477, filed on Jul. 31, 2014.

(51) Int. Cl.
| | |
|---|---|
| *C12N 9/24* | (2006.01) |
| *G01N 33/573* | (2006.01) |
| *C07K 16/28* | (2006.01) |
| *G01N 33/68* | (2006.01) |
| *C07K 14/71* | (2006.01) |
| *C07K 16/40* | (2006.01) |

(52) U.S. Cl.
CPC .......... *G01N 33/573* (2013.01); *C07K 14/71* (2013.01); *C07K 16/28* (2013.01); *C07K 16/40* (2013.01); *C12N 9/2402* (2013.01); *C12Y 302/01031* (2013.01); *G01N 33/6872* (2013.01); *C07K 2317/51* (2013.01); *C07K 2317/515* (2013.01); *C07K 2317/56* (2013.01); *C07K 2317/565* (2013.01); *C07K 2317/92* (2013.01); *G01N 2333/924* (2013.01); *G01N 2800/347* (2013.01); *G01N 2800/52* (2013.01)

(58) Field of Classification Search
CPC .............. G01N 33/573; G01N 33/6872; G01N 2333/924; G01N 2800/347; G01N 2800/52; C07K 14/71; C07K 16/28; C07K 16/40; C07K 2317/51; C07K 2317/515; C07K 2317/56; C07K 2317/565; C07K 2317/92; C12N 9/2402; C12Y 302/01031
See application file for complete search history.

(56) References Cited

FOREIGN PATENT DOCUMENTS

| | | |
|---|---|---|
| WO | 2013/184218 | 12/2013 |
| WO | 2017132772 A1 | 2/2016 |
| WO | 2016/145536 | 9/2016 |

OTHER PUBLICATIONS

Kuro-o M, Matsumura Y, Aizawa H, et al. (1997) Mutation of the mouse klotho gene leads to a syndrome resembling ageing. Nature 390: 45-51.
Nabeshima Y. (2002) Klotho: a fundamental regulator of aging. Ageing Res Rev 1: 627-638.
Matsumura Y, Aizawa H, Shiraki-Iida T, Nagai R, Kuro-o M, Nabeshima Y. (1998) Identification of the human klotho gene and its two transcripts encoding membrane and secreted klotho protein. Biochem Biophys Res Commun 242: 626-630.
Ben-Dov IZ, Galitzer H, Lavi-Moshayoff V, Goetz R, Kuro-o M, Mohammadi M, Sirkis R, Naveh-Many T, Silver J. (2007) The parathyroid is a target organ for FGF23 in rats. J Clin Invest 117: 4003-4008.
Ito S, Kinoshita S, Shiraishi N, Nakagawa S, Sekine S, Fujimori T, Nabeshima YI. Molecular cloning and expression analyses of mouse betaklotho, which encodes a novel Klotho family protein. (2000) Mech Dev 98: 115-119.
Kuro-o M. (2012) Klotho and betaKlotho. Adv Exp Med Biol 728: 25-40.
Hu MC, Shi M, Zhang J, et al. Klotho: a novel phosphaturic substance acting as an autocrine enzyme in the renal proximal tubule. FASEB J 2010;24(9):3438-3450.
Kato Y, Arakawa E, Kinoshita S, et al. Establishment of the anti-Klotho monoclonal antibodies and detection of Klotho protein in kidneys. Biochem Biophys Res Commun 2000;267(2):597-602.
Goetz R, Nakada Y, Hu MC, et al. Isolated C-terminal tail of FGF23 alleviates hypophosphatemia by inhibiting FGF23-FGFR-Klotho complex formation. Proc Natl Acad Sci USA 2010;107(1):407-412.
Kurosu H, Ogawa Y, Miyoshi M, et al. Regulation of fibroblast growth factor-23 signaling by klotho. J Biol Chem 2006;281(10):6120-6123.
Urakawa I, Yamazaki Y, Shimada T, et al. Klotho converts canonical FGF receptor into a specific receptor for FGF23. Nature 2006;444(7120):770-774.
Hu MC, Shi M, Zhang J, et al. Klotho deficiency causes vascular calcification in chronic kidney disease. J Am Soc Nephrol 2011;22(1):124-136.
Imura A, Iwano A, Tohyama 0, et al. Secreted Klotho protein in sera and CSF: implication for post-translational cleavage in release of Klotho protein from cell membrane. FEBS Lett 2004;565(1-3)143-147.

(Continued)

*Primary Examiner* — Robert S Landsman
(74) *Attorney, Agent, or Firm* — Fitch Even Tabin & Flannery LLP

(57) ABSTRACT

An antibody and/or binding fragment thereof, wherein the antibody and/or binding fragment thereof specifically binds to an epitope of a αKlotho polypeptide, optionally a folded αKlotho or optionally with a dissociation constant ($K_D$) of about 2 nM or less, as measured by competitive ELISA assay, methods of making and using to diagnose kidney diseases.

14 Claims, 15 Drawing Sheets

Specification includes a Sequence Listing.

(56) References Cited

OTHER PUBLICATIONS

Bloch L, Sineshchekova 0, Reichenbach D, et al. Klotho is a substrate for alpha-, beta- and gamma-secretase. FEBS Lett 2009;583(19):3221-3224.
Chen CD, Podvin S, Gillespie E, et al. Insulin stimulates the cleavage and release of the extracellular domain of Klotho by ADAM10 and ADAM17. Proc Natl Acad Sci U S A 2007;104(50):19796-19801.
Hu MC, Shi M, Zhang J, et at., Renal production, uptake, and handling of circulating alpha-klotho. J Am Soc Nephrol 27(1): Jan. 2016, pp. 79-90.
Hu MC, Kuro-o M, Moe OW. Secreted klotho and chronic kidney disease. Adv Exp Med Biol 2012;728:126-157.
Aizawa H, Saito Y, Nakamura T, et al. Downregulation of the Klotho gene in the kidney under sustained circulatory stress in rats. Biochem Biophys Res Commun 1998;249(3):865-871.
Cheng MF, Chen LJ, Cheng JT. Decrease of Klotho in the kidney of streptozotocin-induced diabetic rats. J Biomed Biotechnol 2010;2010:513853.
Haruna Y, Kashihara N, Satoh M, et al. Amelioration of progressive renal injury by genetic manipulation of Klotho gene. Proc Natl Acad Sci U S A 2007;104(7):2331-2336.
Koh N, Fujimori T, Nishiguchi S, et al. Severely reduced production of klotho in human chronic renal failure kidney. Biochem Biophys Res Commun 2001;280(4)1 015-1020.
Mitani H, Ishizaka N, Aizawa T, et al. In vivo klotho gene transfer ameliorates angiotensin II-induced renal damage. Hypertension 2002;39(4):838-843.
Wang Y, Sun Z. Klotho gene delivery prevents the progression of spontaneous hypertension and renal damage. Hypertension 2009;54:810-817.
Zhao Y, Banerjee S, Dey N, et al. Klotho depletion contributes to increased inflammation in kidney of the db/db mouse model of diabetes via RelA (serine)536 phosphorylation. Diabetes 2011;60(7)1 907-1916.
Hu MC, Shi M, Zhang J, et al. Klotho deficiency is an early biomarker of renal ischemia-reperfusion injury and its replacement is protective. Kidney Int 2010;78(12):1240-1251.
Hu MC, Moe OW. Klotho as a potential biomarker and therapy for acute kidney injury. Nat Rev Nephrol 2012;8 (7):423-429.
Goetz R, Beenken A, Ibrahim' OA, et al. (2007) Molecular insights into the klotho-dependent, endocrine mode of action of fibroblast growth factor 19 subfamily members. Mol Cell Biol 27:3417-3428.
Shimada T, Kakitani M, Yamazaki Y, Hasegawa H, Takeuchi Y, Fujita T, Fukumoto S, Tomizuka K, Yamashita T. (2004) Targeted ablation of Fgf23 demonstrates an essential physiological role of FGF23 in phosphate and vitamin D metabolism. J Clin Invest 113: 561-568.
Ichikawa S, Imel EA, Kreiter ML, et al. (2007) A homozygous missense mutation in human KLOTHO causes severe tumoral calcinosis. J Clin Invest 117: 2684-2691.
Kuro-o M. (2010) Overview of the FGF23-Klotho axis. Pediatr Nephrol 25: 583-590.
Kurosu H, Kuro OM. (2009) The Klotho gene family as a regulator of endocrine fibroblast growth factors. Mol Cell Endocrinol 299: 72-78.
Ayodele OE, Alebiosu CO. (2010) Burden of chronic kidney disease: an international perspective. Adv Chronic Kidney Dis 17: 215-224.
Soni RK, Weisbord SD, Unruh ML (2010) Health-related quality of life outcomes in chronic kidney disease. Curr Opin Nephrol Hypertens 19: 153-159.
Trivedi H. (2010) Cost implications of caring for chronic kidney disease: are interventions cost-effective? Adv Chronic Kidney Dis 17: 265-270.
Ganesh SK, Stack AG, Levin NW, Hulbert-Shearon T, Port FK. (2001) Association of elevated serum P0(4), Ca x P0 (4) product, and parathyroid hormone with cardiac mortality risk in chronic hemodialysis patients. J Am Soc Nephrol 12:2131-2138.
Tonelli M, Curhan G, Pfeffer M, Sacks F, Thadhani R, Melamed ML, Wiebe N, Muntner P. (2009) Relation between alkaline phosphatase, serum phosphate, and all-cause or cardiovascular mortality. Circulation 120: 1784-1792.
Gutierrez 0, Isakova T, Rhee E, Shah A, Holmes J, Collerone G, Juppner H, Wolf M. (2005) Fibroblast growth factor-23 mitigates hyperphosphatemia but accentuates calciticl deficiency in chronic kidney disease. J Am Soc Nephrol 16: 2205-2215.
Asai 0, Nakatani K, Tanaka T, et al. Decreased renal alpha-Klotho expression in early diabetic nephropathy in humans and mice and its possible role in urinary calcium excretion. Kidney Int 2012; 81 (6): 539-547.
Akimoto T, Kimura T, Watanabe Y, et al. The impact of nephrectomy and renal transplantation on serum levels of soluble Klotho protein. Transplant Proc 2013;45(1):134-136.
Akimoto T, Shiizaki K, Sugase T, et al. The relationship between the soluble Klotho protein and the residual renal function among peritoneal dialysis patients. Clin Exp Nephrol 2012;16(3):442-447.
Akimoto T, Yoshizawa H, Watanabe Y, et al. Characteristics of urinary and serum soluble Klotho protein in patients with different degrees of chronic kidney disease. BMC Nephrol 2012;13:155.
Carpenter TO, Insogna KL, Zhang JH, et al. Circulating Levels of Soluble Klotho and FGF23 in X-Linked Hypophosphatemia: Circadian Variance, Effects of Treatment, and Relationship to Parathyroid Status. J Clin Endociinol Metab 2010;95(11):E352-357.
Crasto CL, Semba RD, Sun K, et al. Relationship of low-circulating "anti-aging" klotho hormone with disability in activities of daily living among older community-dwelling adults. Rejuvenation Res 2012;15(3):295-301.
Devaraj S, Syed B, Chien A, et al. Validation of an immunoassay for soluble klotho protein: decreased levels in diabetes and increased levels in chronic kidney disease. Am J Clin Pathol 2012;137(3):479-485.
Fliser D, Seiler S, Heine GH, et al. Measurement of serum soluble Klotho levels in CKD 5D patients: useful tool or dispensable biomarker? Nephrol Dial Transplant 2012;27(5)1702-1703.
Heijboer AC, Blankenstein MA, Hoenderop J, et al. Laboratory aspects of circulating alpha-Klotho. Nephrol Dial Transplant 2013;28(9):2283-2287.
Kacso IM, Bondor CI, Kacso G. Soluble serum Klotho in diabetic nephropathy: relationship to VEGF-A. Clin Biochem 2012;45(16-17)1 415-1420.
Kim HR, Nam By, Kim DW, et al. Circulating alpha-Klotho levels in CKD and relationship to progression. Am J Kidney Dis 2013;61(6):899-909.
Kitagawa M, Sugiyama H, Morinaga H, et a/. A decreased level of serum soluble Klotho is an independent biomarker associated with arterial stiffness in patients with chronic kidney disease. PLoS One 2013;8(2):e56695.
Komaba H, Koizumi M, Tanaka H, et al. Effects of cinacalcet treatment on serum soluble Klotho levels in haemodialysis patients with secondary hyperparathyroidism. Nephrol Dial Transplant 2012;27(5)1 967-1969.
Pavik I, Jaeger P, Ebner L, et al. Soluble klotho and autosomal dominant polycystic kidney disease. Clin J Am Soc Nephrol 2012;7(2):248-257.
Pavik I, Jaeger P, Ebner L, et al. Secreted Klotho and FGF23 in chronic kidney disease Stage 1 to 5: a sequence suggested from a cross-sectional study. Nephrol Dial Trarisplant 2013;28(2):352-359.
Seiler S, Wen M, Roth HJ, et al. Plasma Klotho is not related to kidney function and does not predict adverse outcome in patients with chronic kidney disease. Kidney Int 2013;83(1):121-128.
Shimamura Y, Hamada K, Inoue K, et al. Serum levels of soluble secreted alpha-Klotho are decreased in the early stages of chronic kidney disease, making it a probable novel biomarker for early diagnosis. Clin Exp Nephrol 2012;16(5):722-729.
Siahanidou T, Garatzioti M, Lazaropoulou C, et al. Plasma soluble alpha-Klotho protein levels in premature and term neonates: correlations with growth and metabolic parameters. Eur J Endocrinol 2012;167(3):433-440.
Sugiura H, Tsuchiya K, Nitta K. Circulating levels of soluble alpha-Klotho in patients with chronic kidney disease. Clin Exp Nephrol 2011 ;1 5(5):795-796.

(56) References Cited

OTHER PUBLICATIONS

Wan M, Smith C, Shah V, et al. Fibroblast growth factor 23 and soluble klotho in children with chronic kidney disease. Nephrol Dial Transplant 2013;28(1)153-161.
Yamazaki Y, Imura A, Urakawa I, et al. Establishment of sandwich ELISA for soluble alpha-Klotho measurement: Age-dependent change of soluble alpha-Klotho levels in healthy subjects. Biochem Biophys Res Commun 2010;398(3):513-518.
Yokoyama K, Imura A, Ohkido I, et al. Serum soluble alpha-Klotho in hemodialysis patients. Clin Nephrol 2012;77(5):347-351.
Semba RD, Cappola AR, Sun K, et al. Plasma klotho and mortality risk in older community-dwelling adults. J Gerontol A Biol Sci Med Sci 2011;66(7):794-800.
Doi S, Zou Y, Togao 0, et al. Klotho inhibits transforming growth factor-beta1 (TGF-beta1) signaling and suppresses renal fibrosis and cancer metastasis in mice. J Biol Chem 2011;286(10):8655-8665.
Ohyama Y, Kurabayashi M, Masuda H, et at Molecular cloning of rat klotho cDNA: markedly decreased expression of klotho by acute inflammatory stress. Biochemical and Biophysical Research Communications 1998;251(3):920-925.
Sugiura H, Yoshida T, Mitobe M, et al. Klotho reduces apoptosis in experimental ischaemic acute kidney injury via HSP-70. Nephrol Dial Transplant 2010;25(1):60-68.
Sugiura H, Yoshida T, Tsuchiya K, et al. Klotho reduces apoptosis in experimental ischaemic acute renal failure. Nephrol Dial Transplant 2005;20(12):2636-2645.
Moreno JA, Izquierdo MC, Sanchez-Nino MD, et al. The inflammatory cytokines TWEAK and TNFalpha reduce renal klotho expression through NFkappaB. J Am Soc Nephrol 2011;22(7):1315-1325.
Fellouse FA, Esaki K, Birtalan S, et al. High-throughput generation of synthetic antibodies from highly functional minimalist phage-displayed libraries. J Mol Biol 2007;373(4):924-940.
Gao J, Sidhu SS, Wells JA. Two-state selection of conformation-specific antibodies. Proc Natl Acad Sci U S A 2009:106(9):3071-3076.
Koellhoffer JF, Chen G, Sandesara RG, et al. Two synthetic antibodies that recognize and neutralize distinct proteolytic forms of the ebola virus envelope glycoprotein. Chembiochem 2012;13(17):2549-2557.
Li B, Russell SJ, Compaan DM, et al. Activation of the proapoptotic death receptor DR5 by oligomeric peptide and antibody agonists. J Mol Biol 2006;361(3):522-536.
Uysal S, Vasquez V, Tereshko V, et al. Crystal structure of full-length KcsA in its closed conformation. Proc Natl Acad Sci U S A 2009;106(16):6644-6649.
Ibrahim' OA, Zhang F, Eliseenkova AV, et al. Biochemical analysis of pathogenic ligand-dependent FGFR2 mutations suggests distinct pathophysiological mechanisms for craniofacial and limb abnormalities. Hum Mol Genet 2004;13(19):2313-2324.
Plotnikov AN, Hubbard SR, Schlessinger J, et al. Crystal structures of two FGF-FGFR complexes reveal the determinants of ligand-receptor specificity. Cell 2000;101(4):413-424.
Persson H, Ye W, Wemimont A, et al. CDR-H3 diversity is not required for antigen recognition by synthetic antibodies. J Mol Biol 2013;425(4):803-811.
Rajan S, Sidhu SS. Simplified synthetic antibody libraries. Methods Enzymol 2012;502:3-21.
Colwill K, Graslund S. A roadmap to generate renewable protein binders to the human proteome. Nat Methods 2011;8(7):551-558.
Olsen SK, Garbi M, Zampieri N, et al. Fibroblast growth factor (FGF) homologous factors share structural but not functional homology with FGFs. J Biol Chem 2003;278(36):34226-34236.
Kurosu H, Choi M, Ogawa Y, et al. Tissue-specific expression of betaKlotho and fibroblast growth factor (FGF) receptor isoforms determines metabolic activity of FGF19 and FGF21. J Biol Chem 2007;282(37):26687-26695.
Kurosu H, Yamamoto M, Clark JD, et al. Suppression of aging in mice by the hormone Klotho. Science 2005; 309(5742):1829-1833.
Hu MC, Shiizaki K, Kuro-o M, et al. Physiology and pathophysiology of an endocrine network of mineral metabolism. Ann Rev Phys 2013;75:503-533.
Hu MC, Kuro-o M, Moe OW. Renal and extrarenal actions of Klotho. Semin Nephrol 2013;33(2):118-129.
Pedersen L, Pedersen SM, Brasen CL, et al. Soluble serum Klotho levels in healthy subjects. Comparison of two different immunoassays. Clin Biochem 2013;46(12):1079-1083.
Grams ME, Chow EK, Segev DL, Coresh J.Lifetime incidence of CKD stages 3-5 in the United States. Am J Kidney Dis. Aug. 2013;62(2):245-52.
Lefranc et al. IMGT unique numbering for immunoglobulin and T cell receptor variable domains and Ig superfamily V-like domains. Development and Comparative Immunology. 2003;27:55-77.
Barker, Sarah L. et al., The demonstration of aKlotho deficiency in human chronic kidney disease with a novel synthetic antibody. Nephrol Dial Transplant (2015) 30:223-233.
Goldstein, Stuart L., Acute kidney injury biomarkers: renal angina and the need for a renal troponin I. BMC Med (2011) 9:135.
Hu, Ming Chang et al., The Emerging Role of Klotho in Clinical Nephrology. Nephrology Dialysis Transplantation, vol. 27, pp. 2650-2657. (2012).
Seo Min Young et al., Renal Klotho Expression in Patients with Acute Kidney Injury is Associated with the Severity of the Injury. The Korean Journal of Internal Medicine, 2015, vol. 30, No. 4, pp. 480-495.
Maltare, Astha et al. "Development and Characterization of Monoclonal Antibodies to Detect Klotho." Monoclonal Antibodies in Immundiagnosis and Immunotherapy. vol. 33 (6) (2014).
Mencke, Rik et al. "Membrane-bound Klotho is not expressed endogenously in healthy or uraemic human vascular tissue." Cardiovascular Research (2015) 108, 220-31.
Rudikoff, Stuart et al. "Single Amino Acid Substitution Altering Antigen-Binding Specificity." Proc. Natl. Acad. Sci. USA. vol. 79, pp. 1979-1983, Mar. 1982, Immunology. (XP007901436).
Scholze, Alexandra et al. "Soluble a-Klotho and its Relation to Kidney Function and Fibroblast Growth Factor-23." J Clin Endocrinol Metal., May 2014, 99(5) : E855-E861.
International Search Report, International Patent Application No. PCT/CA2015/050728, dated Oct. 30, 2015, 7 pages.
Written Opinion, International Patent Application No. PCT/CA2015/050728, dated Oct. 30, 2015, 7 pages.
International Search Report, International Patent Application No. PCT/CA2017/050127, dated May 10, 2017, 6 pages.
Written Opinion, International Patent Application No. PCT/CA2017/050127, dated May 10, 2017, 8 pages.
Paul, WE. Fundamental Immunology, 3rd ed. Raven Press, NY, Chap. 9, pp. 292-295, 1993.
Rudikoff, S. et al. Proc. Natl. Acad. Sci. USA, 79:1979-1983, 1982.
Solman, PM. Research in Immunology, Elsevier, NY, 145(1):33-36, 1994.

A.

C.

A.

B.

C.

A.

B. Healthy volunteer

CKD patient

A. Light chain sequence (SEQ ID NO: 11)

DIQMTQSPSSLSASVGDRVTITCRAS<u>QSVSSA</u>VAWYQQKPGKAPKLLIY<u>SASSLYSGV
PSRFSGSRSGTDFTLTISSLQPEDFATYYC<b>QQAGYSPIT</b></u>FGQGTKVEIK*RTVAAPSVFIF
PPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC*

B. Heavy chain sequence – Fab (SEQ ID NO: 12)

EVQLVESGGGLVQPGGSLRLSCAAS<b>GFNISYYS</b>IHWVRQAPGKGLEWVAY<b>ISPSYGY
T</b>SYADSVKGRFTISADTSKNTAYLQMNSLRAEDTAVYYC<b>ARYYVYASHGWAGYGMD
Y</b>WGQGTLVTVSS*ASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEPKSC
DKTHT*

C. Heavy chain sequence – IgG1 (SEQ ID NO: 13)

EVQLVESGGGLVQPGGSLRLSCAAS<b>GFNISYYS</b>IHWVRQAPGKGLEWVAY<b>ISPSYGY
T</b>SYADSVKGRFTISADTSKNTAYLQMNSLRAEDTAVYYC<b>ARYYVYASHGWAGYGMD
Y</b>WGQGTLVTVSS*ASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK*

D. Heavy chain sequence – IgG4 (SEQ ID NO: 14)

EVQLVESGGGLVQPGGSLRLSCAAS<b>GFNISYYS</b>IHWVRQAPGKGLEWVAY<b>ISPSYGY
T</b>SYADSVKGRFTISADTSKNTAYLQMNSLRAEDTAVYYC<b>ARYYVYASHGWAGYGMD
Y</b>WGQGTLVTVSS*ASTKGPSVFPLAPCSRSTSESTAALGCLVKDYFPEPVTVSWNSGA
LTSGVHTFPAVLQSSGLYSLSSVVTVPSSSLGTKTYTCNVDHKPSNTKVDKRVESKYG
PPCPSCPAPEFLGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSPGK*

NUCLEIC ACIDS ENCODING ANTIBODIES WITH HIGH AFFINITY FOR ALPHA-KLOTHO

CROSS REFERENCE TO RELATED APPLICATIONS

This is a divisional of U.S. application Ser. No. 15/500,478, filed on Jan. 30, 2017, now U.S. Pat. No. 10,228,374, which is a National Phase Entry of PCT international application no. PCT/CA2015/050728, filed on Jul. 31, 2015, which claims the benefit of 35 U.S.C. § 119 based on the priority of U.S. Provisional Patent Application No. 62/031,477, filed Jul. 31, 2014 which is incorporated herein by reference in its entirety.

This invention was made in part with U.S. Government support under NIH Grant Nos. R01DK091392, R01DK092461 and R01DE13686. The U.S. Government may have certain rights in this invention.

INCORPORATION OF SEQUENCE LISTING

A computer readable form of the Sequence Listing "144942-US Sequence Listing_ST25.txt" (36,944 bytes) created on Apr. 8, 2019 is hereby incorporated by reference.

FIELD

An antibody and/or binding fragment thereof that specifically binds to an epitope in αKlotho polypeptide, for example with a dissociation constant ($K_D$) of about 2 nM or less, as measured by competitive ELISA assay, as well as methods of making and using said antibody for example to diagnose kidney diseases.

BACKGROUND

The klotho gene was originally identified as a suppressor of premature aging [1, reviewed in 2]. Klotho is a single-pass transmembrane protein expressed predominantly in kidney, the parathyroid gland, and the choroid plexus [1, 3, 4]. Paralogous proteins with distinct functions and expression profiles, termed βKlotho and γKlotho [5, 6] are also known.

αKlotho has diverse effects including regulating ion transport, Wnt and insulin signaling, renin-angiotensin system, recruitment of stem cells, anti-carcinogenesis, anti-fibrosis, and antioxidation. The highest level of expression of αKlotho is in the kidney [1, 7, 8]. In addition to its transmembrane form which is a co-receptor for fibroblast growth factor (FGF) 23,[9-11] αKlotho is also released into the circulation, urine, and cerebrospinal fluid as an endocrine substance[7, 12, 13] generated by transcript splicing into a truncated peptide[2] or proteolytic release by secretases.[14, 15] A substantial portion of the circulating αKlotho is nephrogenic in origin[16]. The phenotypic similarities between genetic αKlotho ablation and chronic kidney disease (CKD) support the notion that reduced renal expression of αKlotho is pathogenic[1, 16].

Reduced renal αKlotho transcript or protein levels[12,18-24] and serum αKlotho concentration[12, 20] was demonstrated in rodent CKD from nephron reduction surgery, ischemia reperfusion injury, immune complex glomerulonephritis, polygenic or hormonal hypertension, metabolic syndrome, and diabetes.[12, 18-24] This convergence suggests that αKlotho deficiency may be a generic consequence of nephron loss. αKlotho reduction is potentially a sensitive and early biomarker of CKD and also prognostic of CKD complications [22]. Restoration of αKlotho in experimental CKD in rodents ameliorates the kidney disease and extra-renal complications [12, 22, 23]. αKlotho deficiency has also been documented in acute kidney injury (AKI) in both rodents and humans [25]. αKlotho can potentially serve as an early biomarker for AKI as it is reduced much earlier than changes in the current known biomarkers of AKI [26].

αKlotho forms a constitutive binary complex with FGF receptors (FGFRs) to confer selective affinity to FGF23 [10, 27]. Defects in αKlotho expression result in FGF23 resistance and phosphate retention in mice [1, 28] and humans [29]. Therefore, αKlotho and FGF23 have emerged as essential components of the bone-kidney endocrine axis that regulates phosphate metabolism [30, 31].

The extracellular domain of the membrane-anchored form of αKlotho can be secreted as a soluble protein. The soluble form is generated from the membrane-anchored form by membrane-anchored proteases and is released into blood and urine [13, 15]. As noted above, membrane-anchored αKlotho functions as part of the FGF23 receptor complex, whereas secreted αKlotho functions as an endocrine factor that exerts actions on distant organs to exert highly pleiotropic actions as stated above (regulating ion transport, Wnt and insulin signaling, renin-angiotensin system, recruitment of stem cells, anti-carcinogenesis, anti-fibrosis, and antioxidation) [7].

Advanced CKD (Stages 4-5), characterized by kidney damage and decreased kidney function, affects an estimated 2.6 million Canadians, greater than 7% of the population. A recent analysis of National Vital Statistics Report, National Health and Nutrition Examination Surveys and US Renal Data System showed that the lifetime risks for white men, white women, black men, and black women, respectively: CKD stage 3a+, 53.6%, 64.9%, 51.8%, and 63.6% [84]. The impact and burden of CKD and its associated complications on people's lives and the health care system is significant and will worsen in coming years [32-34]. Current approaches to treat CKD include modification of risk factors by diet and medication, and for end stage renal disease (ESRD) by dialysis, and organ replacement. There is an urgent need for additional therapies to, arrest or delay progression of CKD at early stages, before complications arise. The majority of the complications of CKD are embraced within the entity of CKD-mineral bone disturbance (CKD-MBD) which are tied to disturbances of mineral metabolism. Phosphate retention is universally observed in CKD patients and associated with poor outcome [35, 36]. Hyperphosphatemia is usually detected only in advanced stages of CKD, when the disease is destined to progress to end-stage [37].

Recently, it has been discovered that reduced renal αKlotho expression is one of the earliest events in CKD [12].

At present, there are some αKlotho antibodies and diagnostic kits available on the market, but the existing αKlotho antibodies are not of sufficient specificity and not efficient at immunoprecipitating αKlotho from human serum, and the current immune-based assays for αKlotho are costly and inadequate in sensitivity and specificity.

Low αKlotho transcript and protein levels have been described in human kidney from nephrectomy samples of end stage kidneys and biopsies from patients with CKD [21,38]. Studies using an immune-based assay have shown widely disparate results in terms of absolute values of serum αKlotho concentration (100-fold span in levels from different labs) and direction of change (increased, decreased, or no change) with CKD and age[21,39-60]. The discrepant database has thwarted progress and incapacitated the ability to determine whether the promising rodent data can be translated into meaningful human application. In addition to CKD, acute kidney injury (AKI) from a variety of causes is also associated with rapid decrease of αKlotho in the kidney[25, 61-65] and serum in rodents and in urine in humans[25]. There is no data on human serum αKlotho in AKI to date. There is a need for an early, sensitive, and/or specific marker for renal injury in humans[66].

Generating antibodies to conserved proteins is challenging, as animal immunization methods for antibody development are subject to mechanisms that protect against auto-immunity. Synthetic antibody technology offers a powerful alternative because it is applied under defined in vitro conditions, uses antibody libraries that have not been subjected to tolerance selection that remove self-reactive antibodies, and is proven to yield antibodies with high affinities and specificities[67-71]. Within an optimized antibody framework, sequence diversity is introduced into the complementary determining regions (CDR's) by combinatorial mutagenesis. These libraries are coupled with phage display, with each phage particle displaying a unique antigen-binding fragment (Fab) on its surface while carrying the encoding DNA internally, thus achieving direct phenotype-genotype relations. Fab-displaying phage that bind to an antigen of interest are enriched using binding selections with purified antigens on solid support. The CDR's of binding phage clones are identified by DNA sequencing and the Fab proteins are purified from bacteria, or converted to the full-length IgG in mammalian cells.

SUMMARY

This present disclosure relates to an antibody and/or binding fragment thereof that binds specifically to αKlotho protein.

An aspect includes an isolated or purified antibody and/or binding fragment thereof, wherein the antibody and/or binding fragment thereof specifically binds to an epitope of a αKlotho polypeptide with a dissociation constant ($K_D$) of about 2 nM or less, as measured by competitive ELISA assay.

In an embodiment, the αKlotho polypeptide specifically bound by the antibody is a folded αKlotho polypeptide.

A further aspect is antibody and/or binding fragment thereof comprising a light chain variable region and a heavy chain variable region, the light chain variable region comprising complementarity determining region CDR-L3 and the heavy chain variable region comprising complementarity determining regions CDR-H1, CDR-H2 and CDR-H3, with the amino acid sequences of said CDRs comprising one or more of the sequences set forth below:

a. CDR-L3;
(SEQ ID NO: 1)
$X_1X_2X_3X_4PX_5$, i. wherein $X_1$ is A or S, $X_2$ is G or A, $X_3$ is Y or F, $X_4$ is S or A, $X_5$ is I or V;

b. CDR-H1:
(SEQ ID NO: 2)
$X_6X_7X_8X_9X_{10}X_{11}$, wherein $X_6$ is I or V, $X_7$ is S or A, $X_8$ is Y, F or S, $X_9$ is Y, F or S, $X_{10}$ is S or A and $X_{11}$ is I or V;

c. CDR-H2;
(SEQ ID NO: 3)
$X_{12}X_{13}X_{14}X_{15}X_{16}X_{17}X_{18}X_{19}X_{20}X_{21}$, i. wherein and $X_{12}$ is Y, F or S, $X2_{13}$ is I or V, $X_{14}$ is S or A, $X_{15}$ is P or S, $X_{16}$ is S or A, $X_{17}$ is Y or F, $X_{18}$ is G or A, $X_{19}$ is Y or F, $X_{20}$ is T or S and $X_{21}$ is S, A or Y;

d. CDR-H3:
(SEQ ID NO: 4)
$X_{22}X_{23}VYX_{24}X_{25}X_{26}X_{27}WX_{28}GX_{29}GM$, i. wherein $X_{22}$ is Y or F, $X_{23}$ is Y or F, $X_{24}$ is A or S, $X_{25}$ is S or A, $X_{26}$ is H or N, $X_{27}$ is G or A, $X_{28}$ is A or S and $X_{29}$ is Y or F.

Another aspect includes a nucleic acid encoding an antibody and/or binding fragment thereof described herein.

A further aspect is a vector comprising a nucleic acid described herein.

Another aspect includes a recombinant cell producing an antibody and/or binding fragment thereof, nucleic acid or vector described herein.

Another aspect is an immunoassay comprising or using the antibody and/or binding fragment thereof described herein.

Other aspects include a method for producing an antibody and/or binding fragment thereof with specific binding affinity to an epitope of an αKlotho polypeptide described herein, an assay for measuring level of αKlotho polypeptide in a sample, an assay for detecting and/or measuring soluble αKlotho polypeptide as well as methods for screening, for diagnosing or for detecting kidney condition selected from chronic kidney disease (CKD) and acute kidney injury (AKI) in a subject and methods of prognosticating disease progression and/or recovery.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which.

Figure 2:
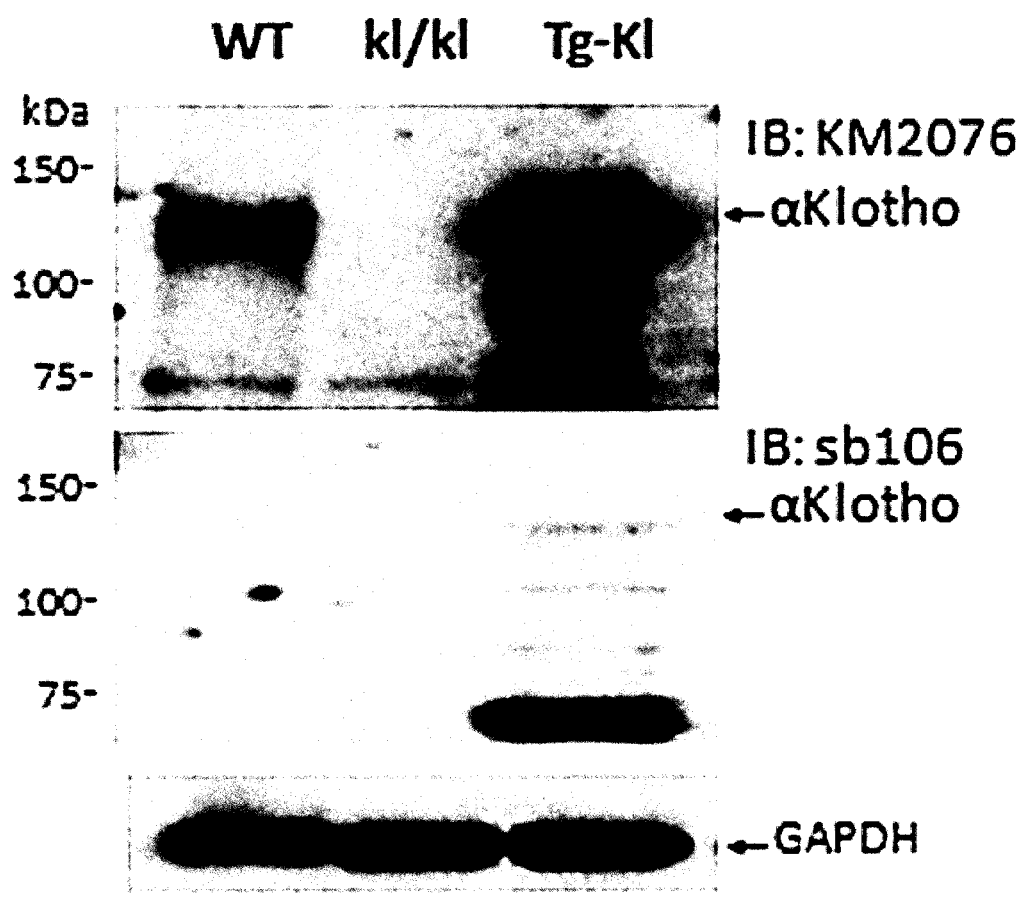
Figure 2:
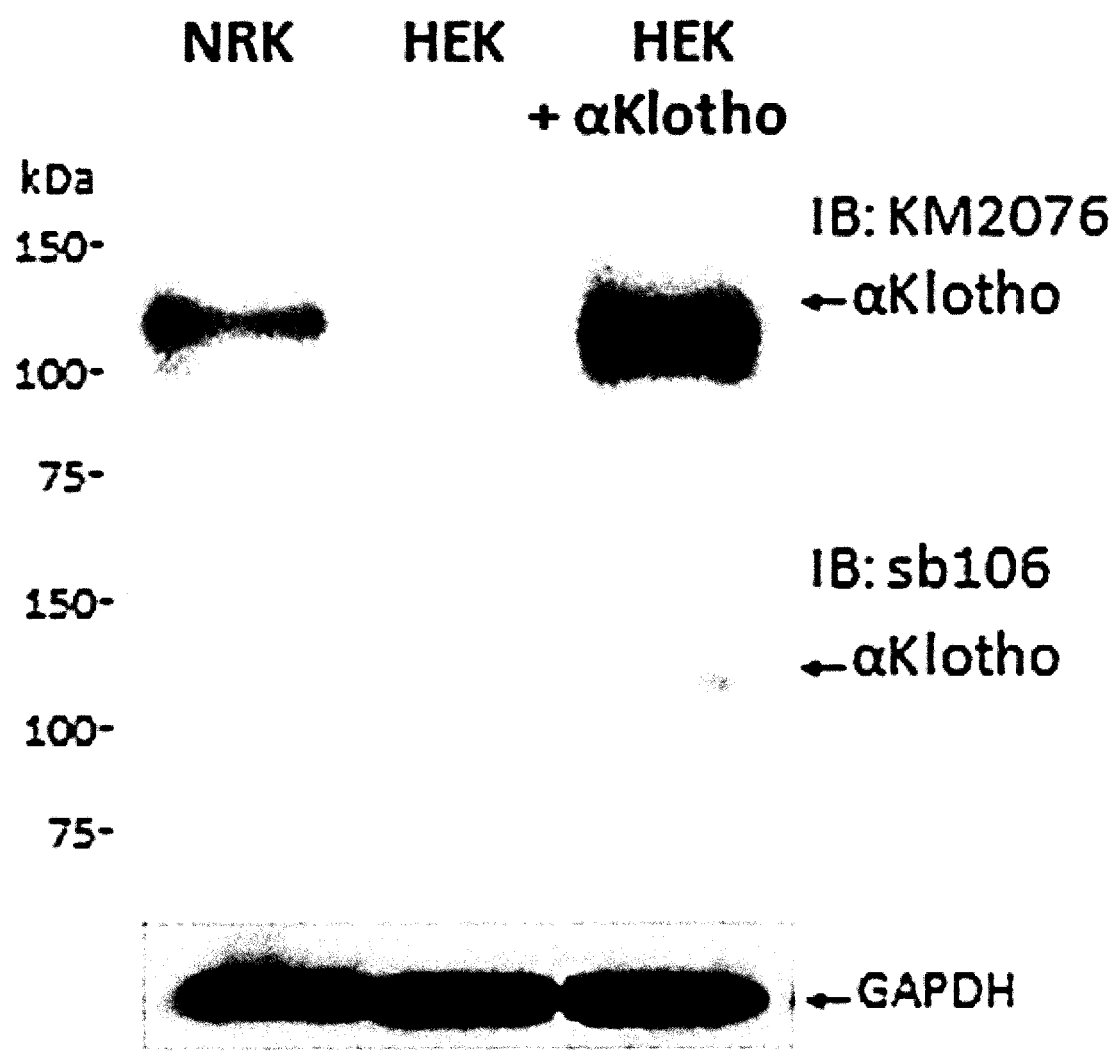
Figure 2:
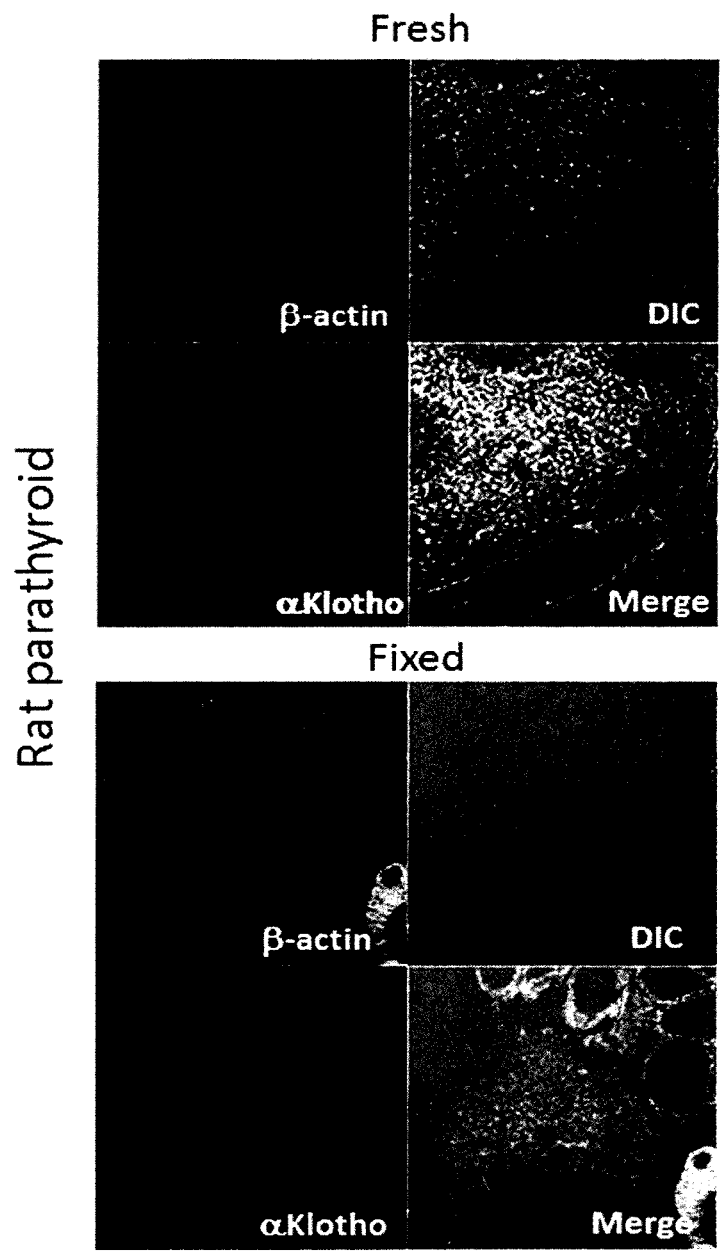
Figure 2:
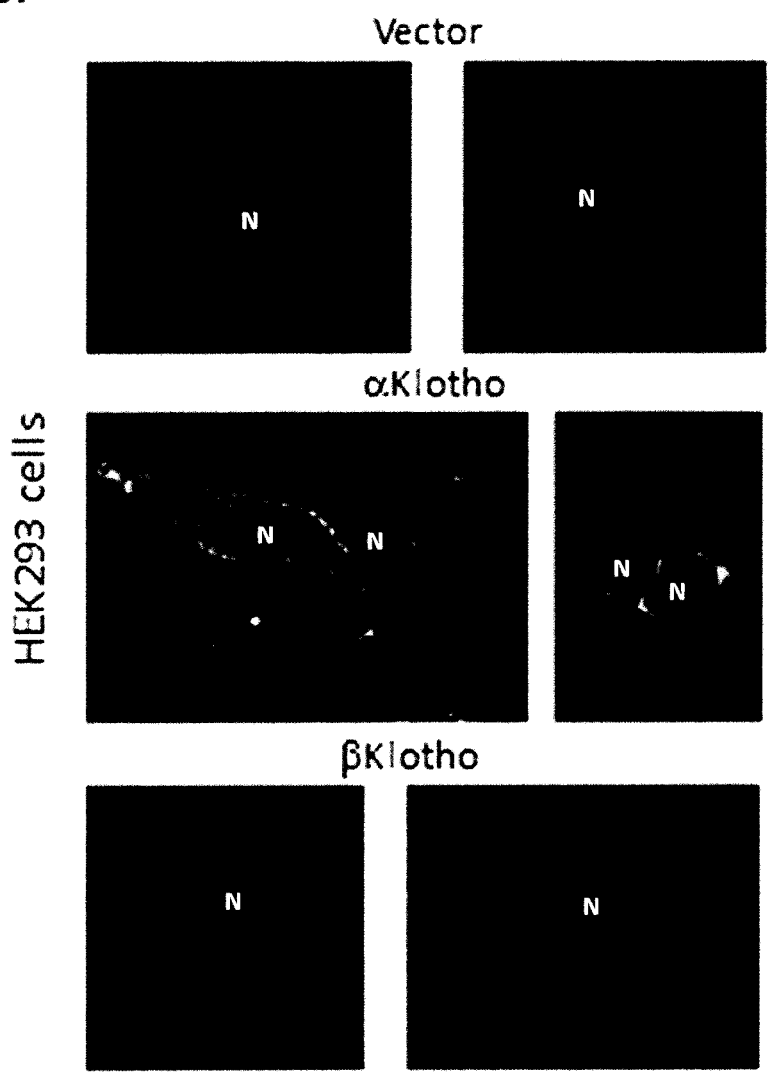

FIG. 2 shows the characterization of sb106-Fab by immunoblot, immunohistochemistry and immunocytochemistry (A) Immunoblot of kidney lysate from wild type mice (WT), homozygous αKlotho hypomorphic mice (kl/kl) and transgenic αKlotho overexpressing mice (Tg-Kl), using the monoclonal antibody KM2076 or the sb106-Fab. GAPDH: Glyceraldehyde phosphate dehydrogenase (B) Immunoblot of lysates from normal rat kidney (NRK) cells, human embryonic kidney (HEK) cells, and HEK cells transfected with a plasmid for over-expression of αKlotho, using the monoclonal antibody KM2076 or the sb106-Fab. (C) Fresh or fixed rat parathyroid tissue probed with phalloidin for β-actin or sb106-IgG. (D) sb106 immunostaining of HEK293T cells transfected with a vector control, or vector for over-expression for αKlotho or βKlotho. Representative cells are shown. The DAPI nuclear staining is labeled "N". (scale bar, 10 μm). αKlotho staining with Fab sb106 was only observed in cells transfected with αKlotho and not in cell transfected with βKlotho.

Figure 3:
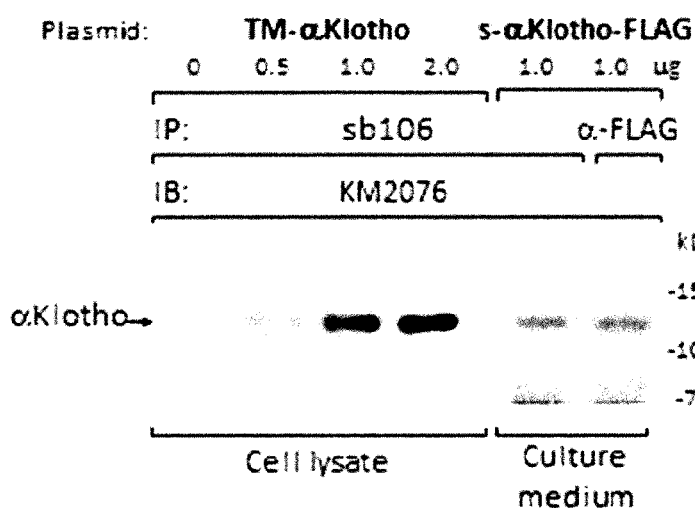
Figure 3:
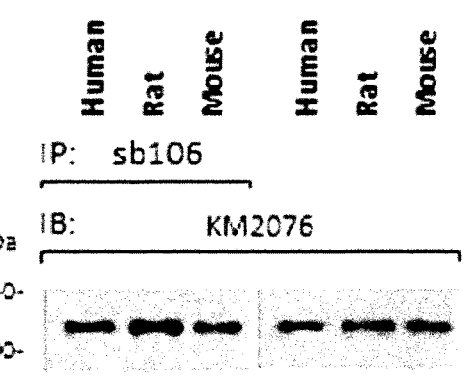
Figure 3:
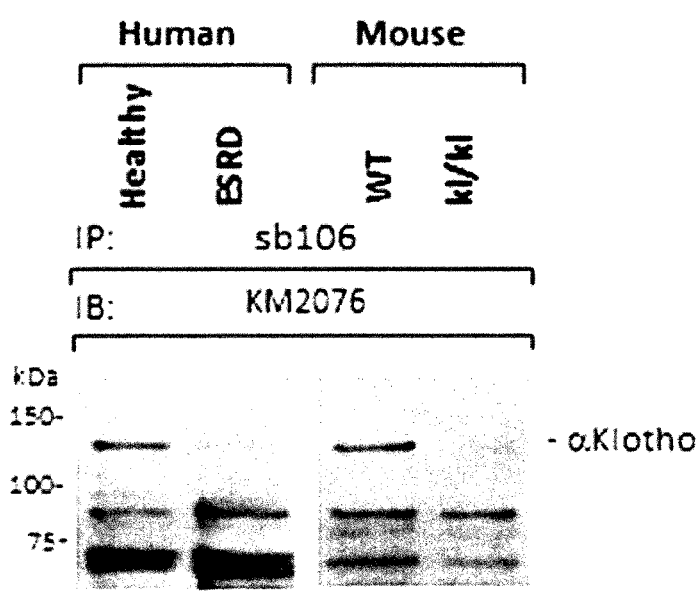

FIG. 3 shows the characterization of sb106-Fab by immunoprecipitation. (A) HEK293 cells were transfected with empty vector or varying quantities (μg/dish) of vector for expression of transmembrane full length αKlotho (TM-αKlotho) or soluble extracellular domain of αKlotho with a C-terminal FLAG epitope (s-αKlotho-FLAG). Cell lysates or cell culture medium was immunoprecipitated (IP) with either sb106-Fab or anti-FLAG MAb. Immunocomplexes were resolved by SDS-PAGE and immunoblotted (IB) with monoclonal anti-αKlotho antibody KM2076. (B) Urine from rat, mouse, or human was immunoprecipitated with sb106-Fab, resolved by SDS-PAGE and immunoblotted (IB) with KM2076 (left three lanes). Size-selected urine (100 kDa cut-off) was directly subjected to SDS-PAGE and immunoblotted (right three lanes). (C) Immunoprecipitations of endogenous αKlotho from serum. Serum samples from wild type (WT) mouse, klotho$^{-/-}$ mouse, normal human, and dialysis patient (ESRD) where incubated with sb106-Fab overnight at 4° C. Sepharose beads conjugated with anti-FLAG antibody were then added and incubated for 2 hours at 4° C. The beads were washed and bound proteins were eluted with 2×SDS sample loading buffer. Immunoblot was performed KM2076 followed by a standard anti-rat IgG secondary for visualization.

Figure 4:
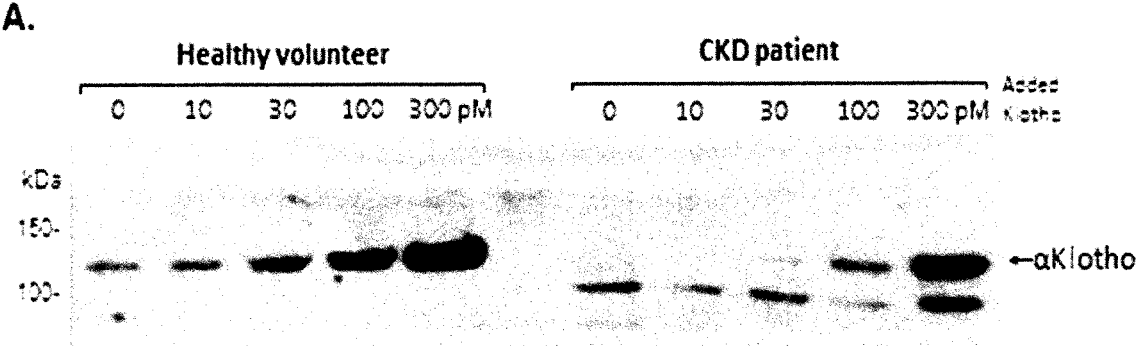
Figure 4:
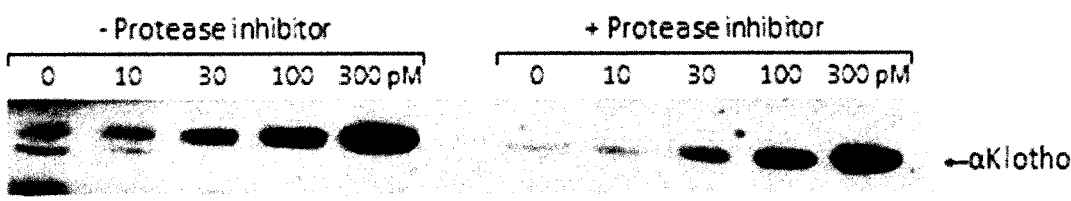
Figure 4:
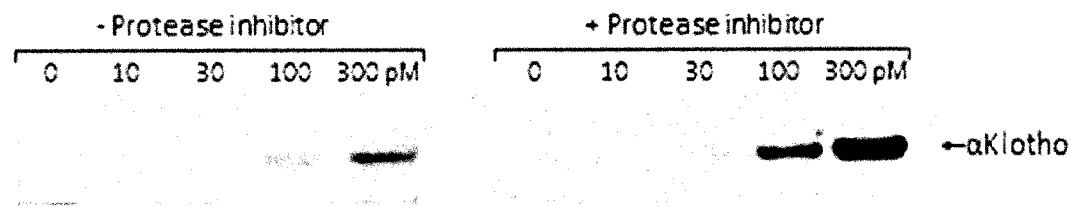
Figure 4:
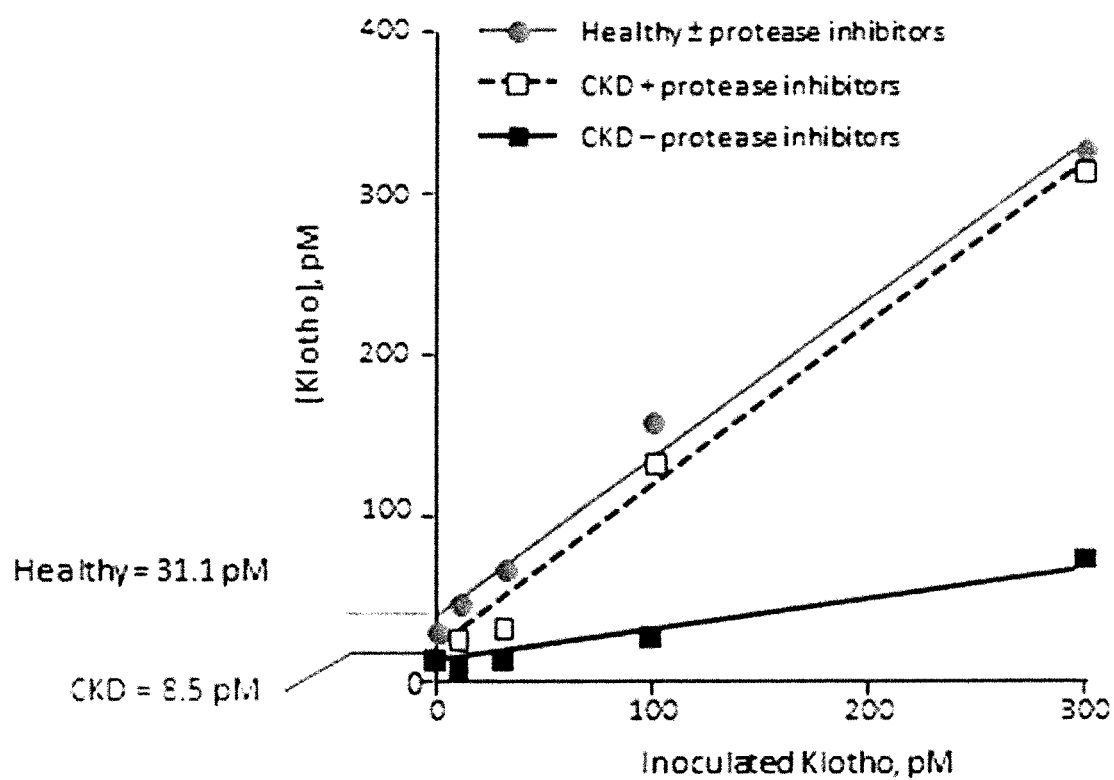

FIG. 4 shows the validation of IP-IB assay using human serum spiked with recombinant αKlotho. (A) Known amounts of soluble human αKlotho ectodomain were added to sera from a healthy volunteer or an anephric dialysis patient (CKD patient). αKlotho was measured in the sera using the IP-IB assay. (B) Similar experiment as in (A) except comparisons were made where protease inhibitors (AEBSF 0.1 mM, aprotinin 0.3 μM, bestatin 10 μM, E-64 1 μM, leupeptin 50 μM, pepstatin A 1 μM) were either included or excluded from the IP. (C) αKlotho levels determined by IP-IB (y-axis) were plotted against the added recombinant αKlotho (x-axis) in the four conditions described above. Extrapolation to zero spiking shows the level of endogenous αKlotho in the serum treated with protease inhibitors. Only one line is shown for healthy serum with or without protease inhibitors as the results were indistinguishable.

Figure 5:
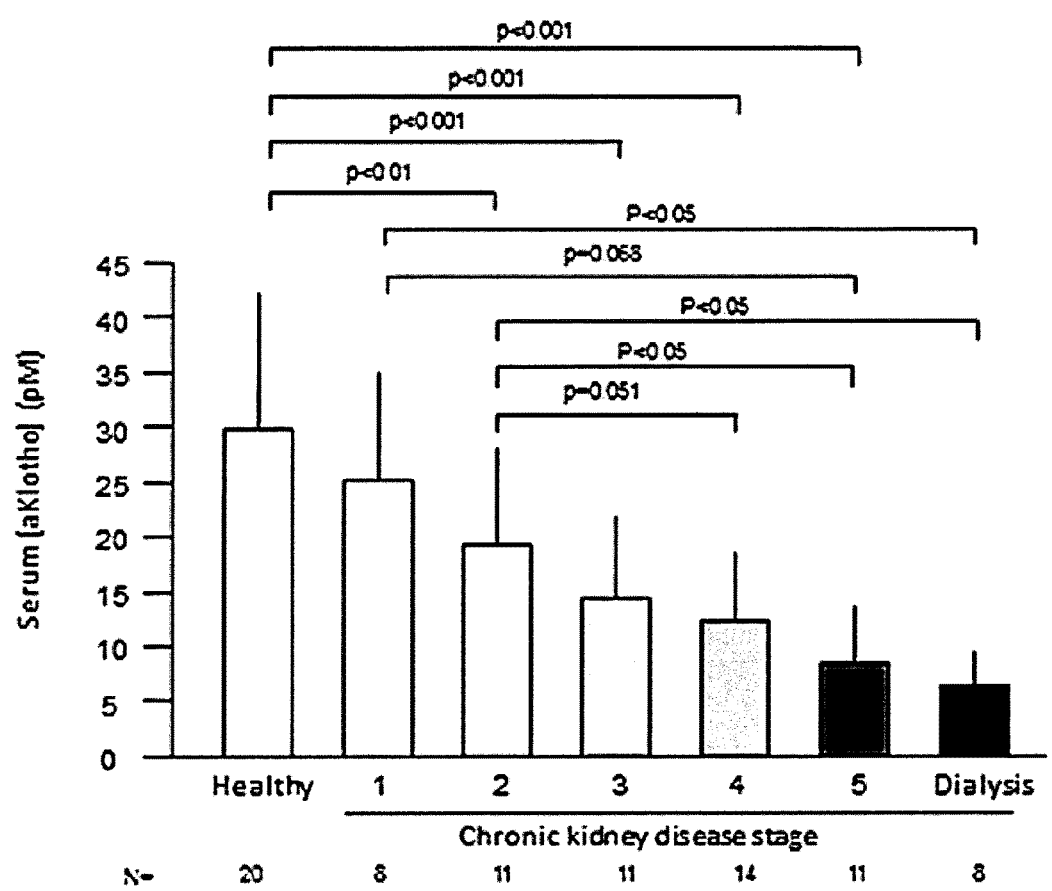
Figure 5:
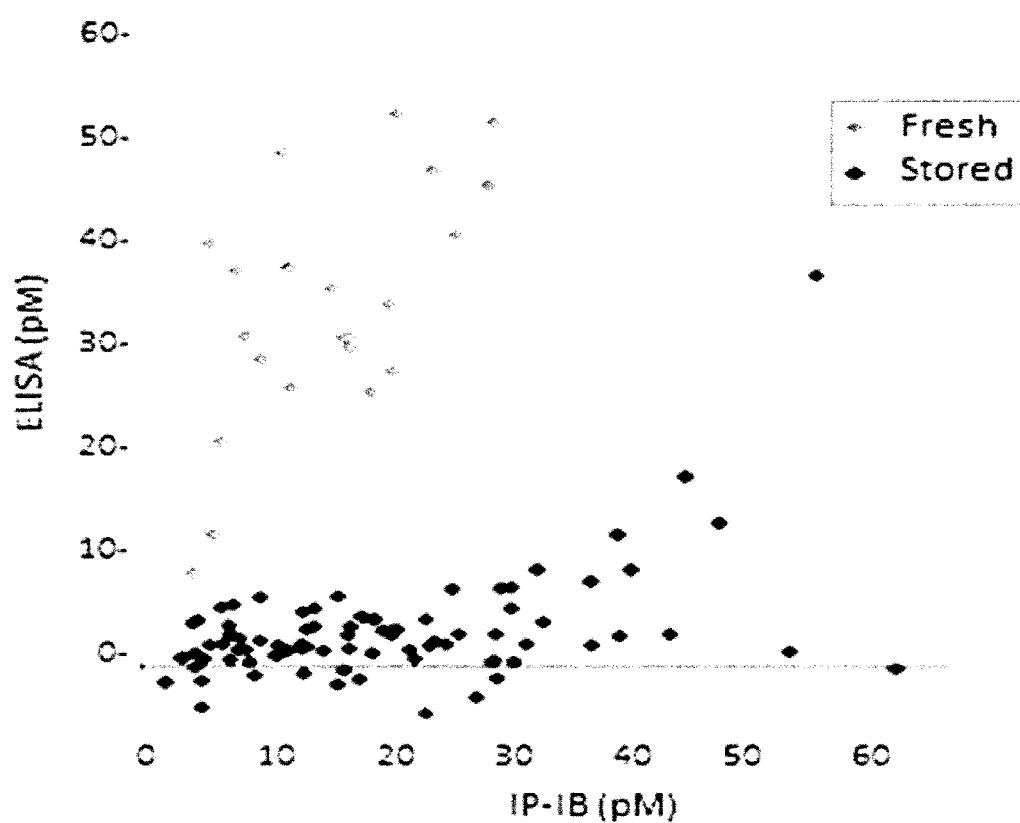
Figure 5:
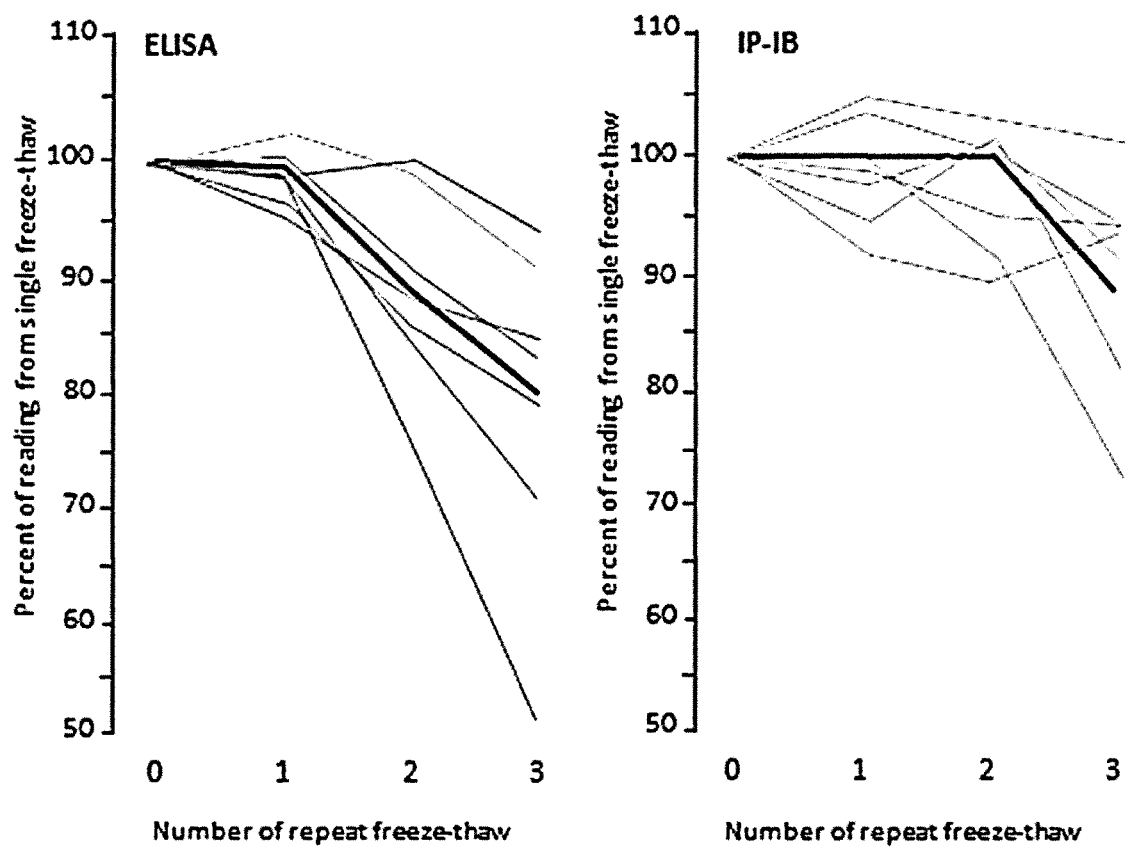

FIG. 5 shows IP-IB assay of serum αKlotho in humans with chronic kidney disease. (A) αKlotho was measured by the IP-IB assay in human sera from normal healthy volunteers and patients from a CKD clinic and dialysis unit using the conventional numerical staging using recombinant αKlotho as a calibration curve. Bars and error bars denote means and standard deviations. The data was analyzed by ANOVA followed by Student-Newman-Keuls test for pairwise multiple comparisons. P values achieving statistical significance between groups are indicated above the brackets. The number of subjects in each group is indicated at the bottom. (B) The concentrations of αKlotho in a large variety of human sera were determined either by IP-IB (x-axis) or by a commercial ELISA (y-axis) in the same samples. The dotted line represents identity. The grey diamonds represent sera that have been through one or more freeze-thaw cycles (stored) and the black diamonds represent sera thawed only once (fresh). (C) Sera from human subjects were assayed by IP-IB and ELISA. The same sera were subjected to the indicated cycles of repeated freeze-thaw and then assayed. Results for each sample were expressed as a percentage of the reading from the same sample thawed only once. The black lines denote the mean of the different subjects.

Figure 6:
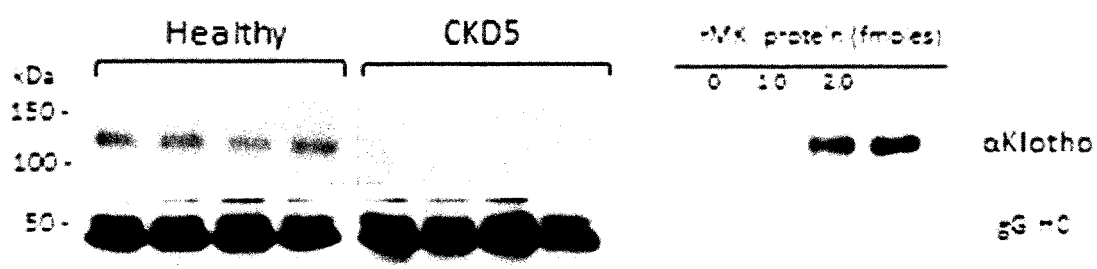
Figure 6:
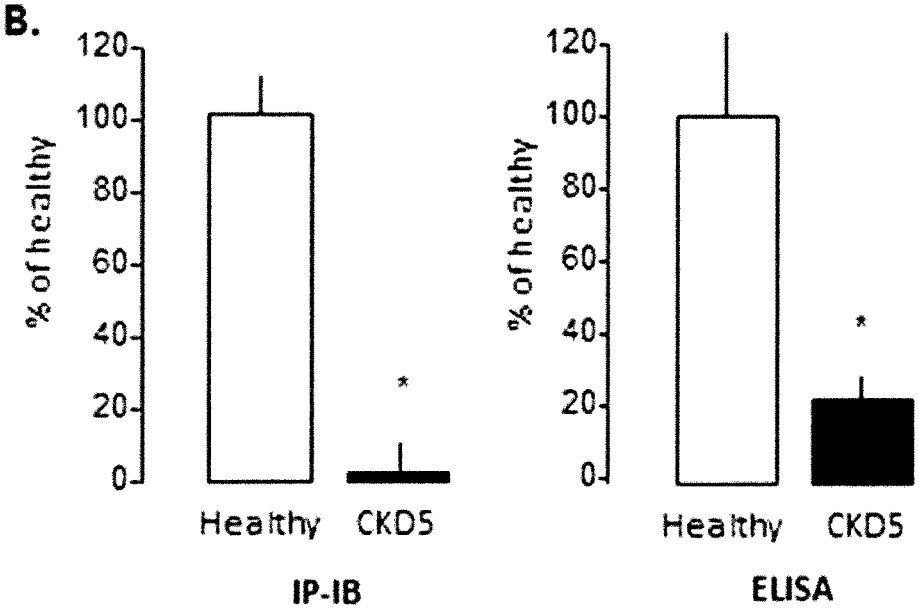

FIG. 6 shows human urinary αKlotho levels. αKlotho was measured in the urine of healthy volunteers or patients with chronic kidney disease stage 5 (CKD5). (A) A representative IP-IB assay using recombinant murine αKlotho (rMKI) as a calibration with four subjects in each group under steady state conditions. Equal amounts of urine creatinine were used for IP-IB. (B) Summary of the data from the IP-IB assay and the commercial ELISA. Bars and error bars represent mean and standard deviation from eight subjects in each group. The mean of the healthy volunteers was set as a reference of 100%.

Figure 7:
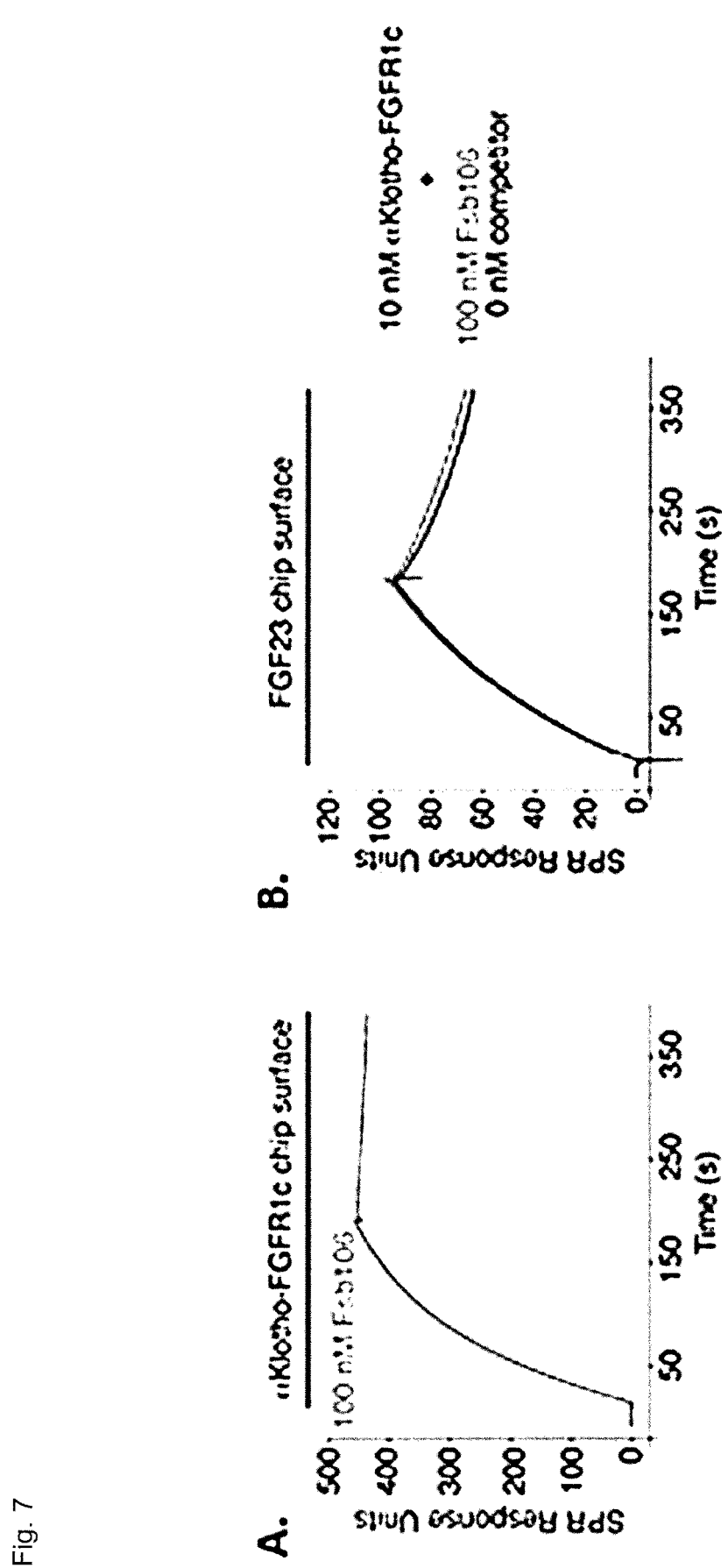

FIG. 7 shows SPR sensorgrams with sb106-Fab (A) SPR sensorgram illustrating binding of sb106-Fab (Fsb106) to the αKlotho-FGFR1c complex. The binary complex of murine αKlotho ectodomain and human FGFR1c ligand-binding domain was immobilized on a biosensor chip and 100 nM of Fsb106 were injected over the chip. Note that the Fsb106 dissociates extremely slowly from the αKlotho-FGFR1c complex. (B) Overlay of SPR sensorgrams showing that sb106-Fab does not inhibit ternary complex formation between FGF23, αKlotho, and FGFR1c. 10 nM of αKlotho-FGFR1c complex alone and a mixture of 10 nM of αKlotho-FGFR1c complex and 100 nM of Fsb106 were injected over a biosensor chip containing immobilized FGF23.

FIG. 8 is a schematic of amino acid sequences of sb106. (A) Light chain sequence (SEQ ID NO: 11) of sb106. (B) Heavy chain sequence—Fab (SEQ ID NO: 12). (C) Heavy chain sequence—IgG1 (SEQ ID NO: 13). (D) Heavy chain sequence—IgG4 (SEQ ID NO: 14). Underlined amino acids are CDR sequences; bold amino acids are variable CDR sequences (L3, H1, H2 & H3); and italicized amino acids are constant domains.

DETAILED DESCRIPTION OF THE DISCLOSURE

I. Definitions

The term "αKlotho" or "alphaKlotho" as used herein refers to all known and naturally occurring αKlotho molecules including, full length αKlotho protein, fragments thereof such as ectodomain fragments, as well as nucleic acids encoding said protein and fragments, as determinable from the context used. Included are the soluble forms of αKlotho (proteolytically cleaved as well as alternatively spliced forms αKlotho, referred to as "soluble αKlotho" when present in a biological fluid such as blood or a fraction thereof, urine or cerebrospinal fluid and having a molecular weight of about 130 kDa, as well as the membrane-anchored form of αKlotho, and including but not limited to mammalian αKlotho such as human αKlotho, or rodent αKlotho including for example mouse and rat αKlotho.

The term "acute kidney injury" or "AKI" as used herein refers to an abrupt and sustained loss of kidney function for example that can lead to accumulation of urea and other chemicals in the blood, that develops within for example seven days of an insult. AKI may be caused by disease, injury such as crushing injury to skeletal muscle and medication. AKI is classified in stages varying from risk (glomerular filtration rate (GFR) decreased by 25%), injury (GFR decreased by 50%), failure (GFR decreased by 75%), loss (complete loss of kidney function for more than four weeks) and end-stage renal disease (complete loss of kidney function for more than three months). AKI can be asymptomatic.

The term "early acute kidney injury" as used herein means prior to rises in serum creatinine.

The term "amino acid" includes all of the naturally occurring amino acids as well as modified amino acids.

The term "antibody" as used herein is intended to include human antibodies, monoclonal antibodies, polyclonal antibodies, single chain and other chimeric antibodies. The antibody may be from recombinant sources and/or produced in transgenic animals. The antibody in an embodiment comprises a heavy chain variable region or a heavy chain comprising a heavy chain complementarity determining region 1, heavy chain complementarity determining region 2 and heavy chain complementarity determining region 3, as well as a light chain variable region or light chain comprising a light chain complementarity determining region 1, light chain complementarity determining region 2 and light chain complementarity determining region 3.

The term "binding fragment" as used herein is intended to include without limitations Fab, Fab', F(ab')2, scFv, dsFv, ds-scFv, dimers, minibodies, diabodies, and multimers thereof, multispecific antibody fragments and Domain Antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-chain length for one another. Examples of conservative amino acid substitution include:

| Conservative Substitutions | |
| --- | --- |
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The term "control" as used herein refers to a sample from a subject or a group of subjects who are either known as having a kidney disease or not having the disease, and/or a value determined from said group of subjects, wherein subjects with an αKlotho level at or below such value are likely to have the disease. The disease can be for example chronic kidney disease (CKD) or acute kidney injury (AKI). The disease can also be for example a stage of CKD such as stage 1 CKD, stage 2 CKD, stage 3 CKD, stage 4 CKD or stage 5 CKD; higher stage being more severe. In addition, the control can be for example derived from tissue of the same type as the sample of the subject being tested. In methods directed to monitoring, the control can also be tissue from the same subject taken at different time point for example the control can be a sample from the same subject taken prior to a treatment for a kidney disease.

The term "chronic kidney disease" or "CKD" refers to a disease causing a progressive loss in renal function. CDK is classified according to five stages which are determined according to a defined glomerular filtration rate (GFR). Stage 1 CKD is defined by a GFR of 90 mL/min/1.73 $m^2$, stage 2 CDK is defined by a GFR between 60-89 mL/min/1.73 $m^2$, stage 3 CKD is defined by a GFR between 30-59 mL/min/1.73 $m^2$, stage 4 CKD is defined by a GFR between 15-29 mL/min/1.73 $m^2$ and stage 5 CKD is defined by a GFR of less than 15 mL/min/1.73 $m^2$. Normal kidney function is defined by a GFR between 100-130 mL/min/1.73 $m^2$ or 90 mL/min/1.73 $m^2$ without proteinuria.

The term "early chronic kidney disease" refers to earlier stages of CKD, and means in an embodiment stage 1 and/or stage 2 CKD are early CKD. Frequently, there are no elevations of FGF23, PTH, and phosphate. Subjects with stage 1 CKD almost never present any symptoms indicating kidney damage. Subjects with stage 2 CKD do not necessarily present symptoms indicating kidney damage but occasionally do.

The term "denatured" as used herein means a polypeptide that has lost tertiary and/or secondary structure (e.g. fully unfolded protein), for example when exposed to denaturing conditions in SDS sample loading buffer.

The term "detectable tag" as used herein refers to moieties such as peptide sequences that can be appended or introduced into recombinant protein.

The term "epitope" as used herein refers to the site on the antigen that is recognized by the antibodies or binding fragments disclosed herein.

The term "heavy chain complementarity determining region" as used herein refers to regions of hypervariability within the heavy chain variable region of an antibody molecule. The heavy chain variable region has three complementarity determining regions termed heavy chain complementarity determining region 1 (CDR-H1), heavy chain complementarity determining region 2 (CDR-H2) and heavy chain complementarity determining region 3 (CDR-H3) from the amino terminus to carboxy terminus. The numbering used herein is the IMGT numbering.

The term "heavy chain variable region" as used herein refers to the variable domain of the heavy chain comprising the heavy chain complementarity determining region 1, heavy chain complementarity determining region 2 and heavy chain complementarity determining region 3. One or more amino acids or nucleotides can be modified for example replaced with a conservative substitution, for example outside the CDR sequences.

The term "host cell" refers to a cell into which a recombinant DNA expression vector can be introduced to produce a recombinant cell. The host cell can be a bacterial cell such as E. coli but can also be any type of microbial, yeast, fungi, insect or mammalian host cell.

The terms "IMGT numbering" or "ImMunoGeneTics database numbering", which are recognized in the art, refer to a system of numbering amino acid residues which are more variable (i.e. hypervariable) than other amino acid residues in the heavy and light chain variable regions of an antibody, or antigen binding portion thereof (85). For the heavy chain variable region, the hypervariable region ranges from amino acid positions 32 to 38 for CDR-H1, amino acid positions 55 to 64 for CDR-H2, and amino acid positions 107 to 117 for CDR-H3. For light chain variable region, the hypervariable region ranges from amino acid positions 24 to 39 for CDR-L1, amino acid positions 56 to 69 for CDR-L2, and amino acid positions 105 to 117 for CDR-L3.

The term "isolated antibody or binding fragment thereof" or "isolated and purified antibody or binding fragment thereof" refers to an antibody or binding fragment thereof that is substantially free of cellular material or culture medium when produced by recombinant DNA techniques, or chemical precursors, or other chemicals when chemically synthesized and/or other antibodies, for example directed to a different epitope.

The term "$K_D$" refers to the dissociation constant of a complex for example of a particular antibody-antigen interaction The term "light chain complementarity determining region" as used herein refers to regions of hypervariability within the light chain variable region of an antibody molecule. Light chain variable regions have three complementarity determining regions termed light chain complementarity determining region 1, light chain complementarity determining region 2 and light chain complementarity determining region 3 from the amino terminus to the carboxy terminus.

The term "light chain variable region" as used herein refers to the variable domain of the light chain comprising the light chain complementarity determining region 1, light chain complementarity determining region 2 and light chain complementarity determining region 3.

The term "native" or "natively folded" as used herein refers to a protein in its native conformation (e.g. 3D conformation) or in a conformation sufficient to confer functionality, including for example partially unfolded protein capable of binding a receptor or ligand. For example, folded αKlotho protein is capable of binding to a FGF receptor such as FGFR1c and can form a FGFR1c: αKlotho complex.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences as well as codon optimized or synonymous codon equivalents. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

The term "polypeptide" as used herein refers to a polymer consisting a large number of amino acid residues bonded together in a chain. The polypeptide can form a part or the whole of a protein. The polypeptide may be arranged in a long, continuous and unbranched peptide chain. The polypeptide may also be arranged in a biologically functional way. The polypeptide may be folded into a specific three dimensional structure that confers it a defined activity. The term "polypeptide" as used herein is used interchangeably with the term "protein".

The term "isolated polypeptide" as used herein means substantially free of cellular material or culture medium when produced by recombinant DNA techniques, or chemical precursors, or other chemicals when chemically synthesized.

The term "reference agent" as used herein refers to an agent that can be used in an assay and that can be for example a standard amount of αKlotho protein used as a reference for example for detecting, screening or for diagnosing kidney condition such as chronic kidney disease and acute kidney disease.

The term "sample" as used herein refers to any biological fluid, cell or tissue sample from a subject, which can be assayed for αKlotho such as soluble biomarkers. For example the sample can comprise urine, serum, plasma or cerebrospinal fluid. The sample can for example be a "post-treatment" sample wherein the sample is obtained after one or more treatments, or a "base-line sample" which is for example used as a base line for assessing disease progression.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, word-length=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(%(G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "subject" as used herein refers to any member of the animal kingdom, preferably a mammal, more preferably a human being or a rodent such as a rat or a mouse. In one embodiment, the subject is suspected of having a kidney disorder such as chronic kidney disease (CKD) or acute kidney injury (AKI).

The term "variant" as used herein includes one or more amino acid and/or nucleotide modifications in a sequence (polypeptide or nucleic acid respectively) for example, one or more modifications of a light chain or a heavy chain complementarity determining region (CDR) disclosed herein that perform substantially the same function as the light chain and heavy chain CDRs disclosed herein in substantially the same way. For instance, variants of the CDRs disclosed herein have the same function of being able to specifically bind to an epitope on the folded αKlotho protein. In one embodiment, variants of CDRs disclosed herein include, without limitation, conservative amino acid substitutions. Variants of the CDRs also include additions and deletions to the CDR sequences disclosed herein. In addition, variant nucleotide sequences and polypeptide sequences include analogs and derivatives thereof.

The term "level" as used herein refers to an amount (e.g. relative amount or concentration) of αKlotho protein that is detectable or measurable in a sample. For example, the soluble αKlotho level can be a concentration such as pM or a relative amount such as 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5.0 and/or 10 times a control level, where for example, the control level is the level of soluble αKlotho in a healthy subject.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Antibody and/or Binding Fragment Thereof

The present disclosure relates to an antibody and/or binding fragment thereof and methods of making and use for example for diagnosing and/or prognosticating kidney diseases.

Figure 1:
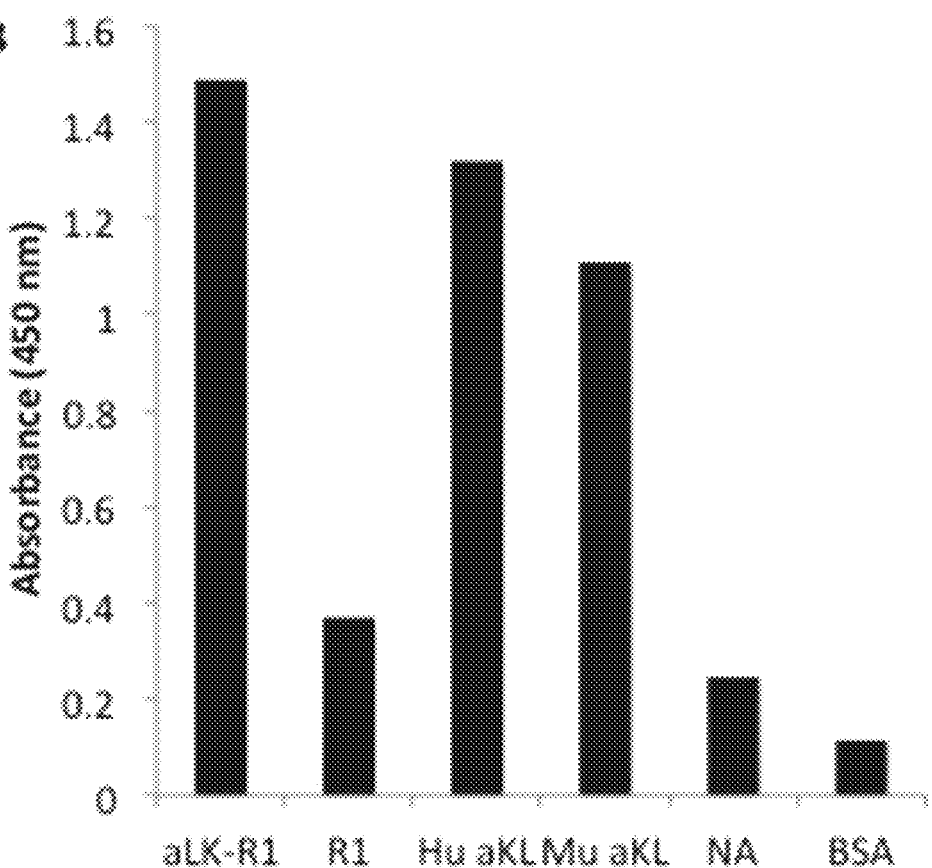
FIG. 1 shows the sequence, specificity and affinity of sb106 (A) CDR sequences for anti-αKlotho sb106 in the IMGT numbering scheme. (B) Specificity determination of anti-αKlotho sb106 by Fab-phage ELISA: sb106 Fab-phage were incubated with the following immobilized antigens: a complex of FGFR1c/αKlotho complex (aKL-R1), FGFR1c alone (R1), human αKlotho (Hu aKL) and mouse αKlotho (Mu aKL), or neutravidin (NA) and bovine serum albumin (BSA) as negative controls. After washing off unbound phage, bound phages were detected using an HRP-conjugated anti-phage antibody. Colorimetric HRP reagents allow for absorbance readings at 450 nm. (C) Estimation of affinity by competitive Fab-phage ELISA. sb106 Fab-phage were pre-incubated with 50, 5, 0.5, 0.05, 0.005 and 0.0005 nM soluble human αKlotho. The binding signals to immobilized human αKlotho reported are an average of two data sets. The reduction in binding to immobilized αKlotho is indicative of the fraction bound to soluble αKlotho, thus a 50% reduction in signal occurs when the soluble αKlotho concentration is approximately equal to the $K_D$ of the interaction.
Figure 1:
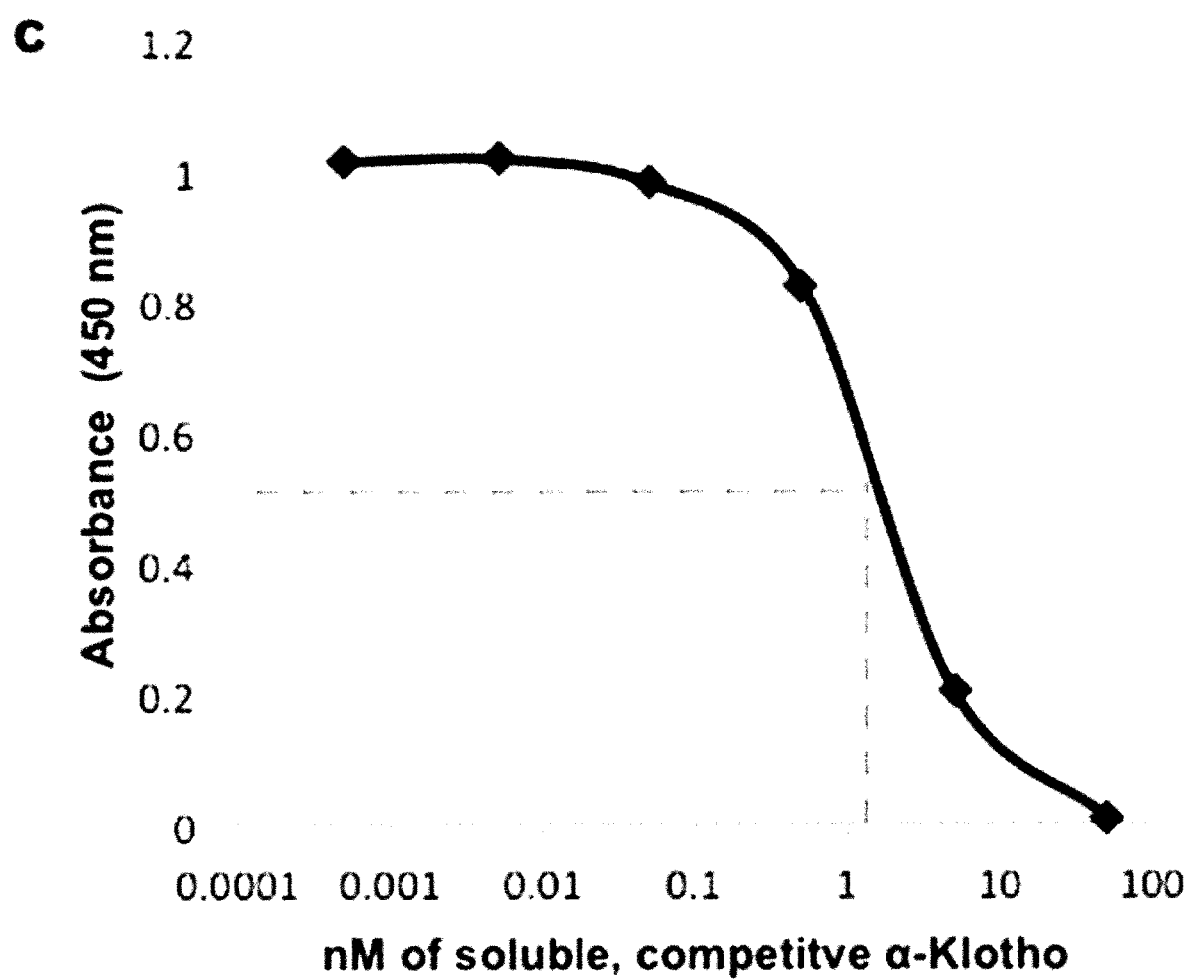

Accordingly, a first aspect is a an antibody and/or binding fragment thereof, wherein the antibody and/or binding fragment thereof specifically binds to an epitope of a αKlotho polypeptide with a dissociation constant ($K_D$) of about 10 nM or less, as measured by competitive ELISA assay. As shown in the Examples below, competitive ELISA assays showed a dose-response curve for anti-αKlotho sb106 binding to αKlotho, and the affinity of the interaction was estimated to be around 1-2 nM (FIG. 1C).

In an embodiment, the αKlotho polypeptide is folded, optionally in native conformation (e.g. fully folded). As demonstrated herein, the anti-αKlotho sb106 antibody has specific binding affinity to folded αKlotho such as natively folded αKlotho. For example, as shown in Example 5, the sb106 antibody has high binding affinity to αKlotho under native conditions but has much weaker or no binding affinity to αKlotho under denaturing conditions.

Accordingly another aspect is an antibody and/or binding fragment thereof, wherein the antibody and/or binding fragment thereof specifically binds to an epitope of a folded αKlotho polypeptide.

Further, anti-αKlotho sb106 has a high binding affinity in freshly prepared or mildly fixed cells.

Accordingly a further aspect is an antibody and/or binding fragment thereof, wherein the antibody and/or binding fragment thereof specifically binds to αKlotho polypeptide in an unfixed or mildly fixed sample.

In an embodiment, the αKlotho polypeptide in the unfixed or mildly fixed sample is folded αKlotho.

The CDR regions of sb106 were determined and are shown In FIG. 1A. Further homologous mutations were introduced at each amino acid position of the SB106 CDRs, (e.g. for each position either the original amino acid was retained or a conservative amino acid change was introduced and a new Fab-phage library was constructed. Selections were performed using the new library using the alphaKlotho-FGFR1c complex as an antigen. Clones that bound to the antigen were isolated and sequenced and are shown in Table 2.

Accordingly another aspect includes an antibody and/or binding fragment thereof comprising a light chain variable region and a heavy chain variable region, the light chain variable region comprising complementarity determining region CDR-L3 and the heavy chain variable region comprising complementarity determining regions CDR-H1, CDR-H2 and CDR-H3, one or more of said CDRs comprising an amino acid sequence as set forth below:

CDR-L3;
(SEQ ID NO: 1)
$X_1X_2X_3X_4PX_5$, wherein $X_1$ is A or S, $X_2$ is G or A, $X_3$ is Y or F, $X_4$ is S or A, $X_5$ is I or V;

CDR-H1:
(SEQ ID NO: 2)
$X_6X_7X_8X_9X_{10}X_{11}$, wherein $X_6$ is I or V, $X_7$ is S or A, $X_8$ is Y, F or S, $X_9$ is Y, F or S, $X_{10}$ is S or A and $X_{11}$ is I or V;

CDR-H2;
(SEQ ID NO: 3)
$X_{12}X_{13}X_{14}X_{15}X_{16}X_{17}X_{18}X_{19}X_{20}X_{21}$, wherein and $X_{12}$ is Y, F or S, $X_{213}$ is I or V, $X_{14}$ is S or A, $X_{15}$ is P or S, $X_{16}$ is S or A, $X_{17}$ is Y or F, $X_{18}$ is G or A, $X_{19}$ is Y or F, $X_{20}$ is T or S and $X_{21}$ is S, A or Y;

CDR-H3:
(SEQ ID NO: 4)
$X_{22}X_{23}VYX_{24}X_{25}X_{26}X_{27}WX_{28}GX_{29}GM$, wherein $X_{22}$ is Y or F, $X_{23}$ is Y or F, $X_{24}$ is A or S, $X_{25}$ is S or A, $X_{26}$ is H or N, $X_{27}$ is G or A, $X_{28}$ is A or S and $X_{29}$ is Y or F.

Antibody fragments were isolated having CDR sequences as described in Table 2. In an embodiment, the antibody or binding fragment thereof has a CDR-L3, CDR-H1, CDR-H2 and CDR-H3 selected from the SEQ ID NOs: 15-120 as listed in Table 2.

In an embodiment, the antibody comprises a CDR-L3 with a sequence selected from SEQ ID NO: 1, a CDRH1 with a sequence selected from SEQ ID NO: 2, a CDR-H2 with a sequence selected from SEQ ID NO:3 and/or a CDR-H3 selected from SEQ ID NO:4 and exhibits a $K_D$ for αKlotho specific binding of about or less than 10 nM, about or less than 9 nM, about or less than 8 nM, about or less than 7 nM, about or less than 6 nM, about or less than 5 nM, about or less than 4 nM, about or less than 3 nM, about or less than 2 nM or about or less than 1 nM.

As mentioned, the sequences of Fab anti-αKlotho sb106 CDRL3 and CDRH1, 2, 3 are shown here (FIG. 1A) and in SEQ ID NOs: 5-8. To further characterize the binding specificity of a clone, the anti-αKlotho sb106 antibody was assayed against a panel of individually purified components (FIG. 1B). Anti-αKlotho sb106 binds to αKlotho alone or within the context of the FGFR1c/αKlotho complex, and is cross-reactive to both human and mouse species. Anti-αKlotho sb106 is also cross-reactive to rat species.

Accordingly in another embodiment, the complementarity determining regions comprise the amino acid sequences set forth below:

Light Chain Variable Region:

(SEQ ID NO: 5)
CDR-L3: AGYSPI

Heavy Chain Variable Region:

(SEQ ID NO: 6)
CDR-H1: ISYYSI (SEQ ID NO: 7)
CDR-H2: YISPSYGYTS (SEQ ID NO: 8)
CDR-H3: YYVYASHGWAGYGM

In a further embodiment, the light chain variable region further comprises complementarity determining regions CDR-L1 and/or CDR-L2 comprising the amino acid sequences set forth below:

CDR-L1: QSVSSA (SEQ ID NO: 9)

CDR-L2: SAS (SEQ ID NO: 10)

In another embodiment, the complementarity determining regions comprise one or more of the amino acid sequences as set forth in SEQ ID NOs: 5-8, or 15-120. In an embodiment, the CDR regions comprise a CDR-L3, CDR-H1, CDR-H2 and CDR-H3

In another embodiment, the antibody and/or binding fragment thereof comprises a light chain with the amino acid sequence set forth below:

Light Chain Sequence:

(SEQ ID NO: 11)
DIQMTQSPSSLSASVGDRVTITCRASQSVSSAVAWYQQKPGKAPKLLIYS

ASSLYSGVPSRFSGSRSGTDFTLTISSLQPEDFATYYCQQAGYSPITFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In another embodiment, the antibody and/or binding fragment thereof comprises a heavy chain variable region with the amino acid sequence set forth below:

Heavy Chain Variable Region Sequence:

(SEQ ID NO: 12)
EVQLVESGGGLVQPGGSLRLSCAASGFNISYYSIHWVRQAPGKGLEWVAY

ISPSYGYTSYADSVKGRFTISADTSKNTAYLQMNSLRAEDTAVYYCARYY

VYASHGWAGYGMDYWGQGTLVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSCDKTHT

The antibody optionally a human antibody can be any class of immunoglobulins including: IgM, IgG, IgD, IgA or IgE; and any isotype, including: IgG1, IgG2, IgG3 and IgG4.

Humanized or chimeric antibody may include sequences from one or more than one isotype or class.

Further, antibodies described herein may be produced as antigen binding fragments such as Fab, Fab' F(ab')$_2$, Fd, Fv and single domain antibody fragments, or as single chain antibodies in which the heavy and light chains are linked by a spacer. Also, the human or chimeric antibodies may exist in monomeric or polymeric form.

Chimeric antibodies can be prepared using recombinant techniques. As described in the Examples, the Fab identified in the screen was reformatted into full length IgG by subcloning the variable domains of the antibody's light and heavy chains into mammalian expression vectors and producing the IgG protein for example as shown in the Examples using human embryonic kidney cells (HEK293T). As described elsewhere any cell type suitable for expressing an antibody can be used.

In yet another embodiment, the antibody and/or binding fragment thereof comprises a heavy chain IgG1 or IgG4 isotype, optionally with the amino acid sequence of an isotype set forth below:

IgG1:

(SEQ ID NO: 13)
EVQLVESGGGLVQPGGSLRLSCAASGFNISYYSIHWVRQAPGKGLEWVA

YISPSYGYTSYADSVKGRFTISADTSKNTAYLQMNSLRAEDTAVYYCAR

YYVYASHGWAGYGMDYWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALH

NHYTQKSLSLSPGK

IgG4:

(SEQ ID NO: 14)
EVQLVESGGGLVQPGGSLRLSCAASGFNISYYSIHWVRQAPGKGLEWVA

YISPSYGYTSYADSVKGRFTISADTSKNTAYLQMNSLRAEDTAVYYCAR

YYVYASHGWAGYGMDYWGQGTLVTVSSASTKGPSVFPLAPCSRSTSEST

AALGCLVKDYFPEPVTVSWNSGALTSGVHTFPAVLQSSGLYSLSSVVTV

PSSSLGTKTYTCNVDHKPSNTKVDKRVESKYGPPCPSCPAPEFLGGPSV

FLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNHY

TQKSLSLSPGK

In yet another embodiment, the light chain complementarity determining region CDR-L3 and heavy chain complementarity determining regions CDR-H1, CDR-H2 and CDR-H3 have at least 70%, at least 80% or at least 90% sequence identity to SEQ ID NOS: 5 to 8, respectively. Specific CDR sequences are provided in SEQ ID NOs: 15-120 as shown in Table 2 which include at least 70% sequence identity to SEQ ID NOs:5-8.

In an embodiment, the antibody, binding fragment thereof, optionally the CDR sequence has one or more conservative substitutions.

In yet another embodiment, the antibody comprises the light chain complementarity determining region CDR-L3 and heavy chain complementarity determining regions CDR-H1, CDR-H2 and CDR-H3 having a sequence set for in SEQ ID NOS: 1 to 4, respectively, optionally with the light chain variable region, the heavy chain variable region having at least 70%, at least 80% or at least 90% sequence identity to SEQ ID NOs: 11 and 12 respectively or optionally in the context of a heavy chain IgG1 or IgG4, having at least 70%, at least 80% or at least 90% sequence identity to SEQ ID NOs:13 and 14. For example one of more CDRs described herein can be grafted into an optimized or selected antibody, antibody chain or variable region.

In one embodiment, the antibody and/or binding fragment thereof is selected from the group consisting of a an immunoglobulin molecule, a Fab, a Fab', a F(ab)2, a F(ab')2, a Fv, a disulfide linked Fv, a scFv, a disulfide linked scFv, a single chain domain antibody, a diabody, a dimer, a minibody, a bispecific antibody fragment, a chimeric antibody, a human antibody, a humanized antibody and a polyclonal antibody.

Fab, Fab' and F(ab')$_2$, scFv, dsFv, ds-scFv, dimers, minibodies, diabodies, bispecific antibody fragments and other fragments can be synthesized by recombinant techniques.

Antibodies can also be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments.

In an embodiment, the antibody is a human antibody.

Human antibodies are optionally obtained from transgenic animals (U.S. Pat. Nos. 6,150,584; 6,114,598; and 5,770,429). In this approach the heavy chain joining region ($J_H$) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

In an embodiment, the antibody is a chimeric antibody comprising one or more CDRs selected from SEQ ID NOs: 1-10 or SEQ ID NOs: 15 to 120.

As mentioned above, FIG. 10 demonstrates for example that anti-αKlotho sb106 binds to αKlotho either alone or in the context of a FGFR/αKlotho complex such as a FGFR1c/αKlotho complex. The affinity of the interaction between anti-αKlotho sb106 and αKlotho, as measured by competitive ELISA assays, is in the single-digit nanomolar range ($IC_{50}$=1.7 nM).

In one embodiment, the antibody and/or binding fragment thereof has a $K_D$ for αKlotho specific binding of about or less than 10 nM, about or less than 9 nM, about or less than 8 nM, about or less than 7 nM, about or less than 6 nM, about or less than 5 nM, about or less than 4 nM, about or less than 3 nM, about or less than 2 nM or about or less than 1 nM.

The antibody and/or binding fragment thereof herein disclosed is cross-reactive to several species. In an embodiment, the αKlotho polypeptide bound is mammalian αKlotho polypeptide, for example, the αKlotho polypeptide is selected from human αKlotho polypeptide or rodent αKlotho polypeptide such as mouse αKlotho polypeptide or rat αKlotho polypeptide.

In another embodiment, the folded αKlotho polypeptide is soluble folded αKlotho polypeptide. For example, the antibody and/or binding fragment thereof binds soluble folded αKlotho polypeptide found in urine, plasma, and/or serum.

In yet another embodiment, the antibody and/or binding fragment thereof binds a complex comprising folded αKlotho polypeptide. For example, the folded αKlotho polypeptide forms a complex with a fibroblast growth factor (FGF) receptor, optionally FGFR1c.

In a further embodiment, the antibody and/or binding fragment is labelled and/or conjugated to a tag, for example to produce a diagnostic agent. For example, the detectable tag can be a purification tag such as a His-tag, a HA-tag, a GST-tag, biotin or a FLAG-tag.

The label is preferably capable of producing, either directly or indirectly, a detectable signal. For example, the label may be radio-opaque or a radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

Another aspect of the disclosure relates to an antibody complex comprising the antibody and/or binding fragment thereof and αKlotho, optionally further comprising FGFR1c.

In an embodiment, the antibody complex comprises FGFR1c and optionally further comprises FGF23.

In an embodiment, the antibody and/or binding fragment thereof is an isolated antibody and/or binding fragment thereof.

Yet another aspect is a nucleic acid encoding an antibody and/or part thereof such as a binding fragment thereof described herein. In an embodiment, the nucleic acid encodes an antibody and/or binding fragment thereof comprising a light chain variable region and a heavy chain variable region, the light chain variable region comprising complementarity determining regions CDR-L1, CDR-L2 and CDR-L3 and the heavy chain variable region comprising complementarity determining regions CDR-H1, CDR-H2 and CDR-H3, with the amino acid sequences of said CDRs comprising one or more of the sequences set forth below:

(SEQ ID NO: 1)
CDR-L3; $X_1X_2X_3X_4PX_5$, wherein $X_1$ is A or S, $X_2$ is G or A, $X_3$ is Y or F, $X_4$ is S or A, $X_5$ is I or V;

(SEQ ID NO: 2)
CDR-H1: $X_6X_7X_8X_9X_{10}X_{11}$, wherein $X_6$ is I or V, $X_7$ is S or A, $X_8$, s Y, F or S, $X_9$ is Y, F or S, $X_{10}$ is S or A and $X_{11}$ is I or V;

(SEQ ID NO: 3)
CDR-H2; $X_{12}X_{13}X_{14}X_{15}X_{16}X_{17}X_{18}X_{19}X_{20}X_{21}$, wherein and $X_{12}$ is Y, F or S, $X2_{13}$ is I or V, $X_{14}$ is S or A, $X_{15}$ is P or S, $X_{16}$ is S or A, $X_{17}$ is Y or F, $X_{18}$ is G or A, $X_{19}$ is Y or F, $X_{20}$ is T or S and $X_{21}$ is S, A or Y;

(SEQ ID NO: 4)
CDR-H3: $X_{22}X_{23}VYX_{24}X_{25}X_{26}X_{27}WX_{28}GX_{29}GM$, wherein $X_{22}$ is Y or F, $X_{23}$ is Y or F, $X_{24}$ is A or S, $X_{25}$ is S or A, $X_{26}$ is H or N, $X_{27}$ is G or A, $X_{28}$ is A or S and $X_{29}$ is Y or F.

Nucleic acids encoding a heavy chain or a light chain are also provided, for example encoding a heavy chain comprising CDR-H1, CDR-H2 and/or CDR-H3 regions described herein or encoding a light chain comprising CDR-L1, CDR-L2 and/or CDR-L3 regions described herein.

The present disclosure also provides variants of the nucleic acid sequences that encode for the antibody and/or binding fragment thereof disclosed herein. For example, the variants include nucleotide sequences that hybridize to the nucleic acid sequences encoding the antibody and/or binding fragment thereof disclosed herein under at least moderately stringent hybridization conditions or codon degenerate or optimized sequences In another embodiment, the variant nucleic acid sequences have at least 70%, most preferably at least 80%, even more preferably at least 90% and even most preferably at least 95% sequence identity to nucleic acid sequences encoding SEQ ID NOs: 1 to 120.

The antibodies described herein can comprise one or more of the features described herein.

In an embodiment, the nucleic acid is an isolated nucleic acid.

Another aspect is a vector comprising the nucleic acid herein disclosed. In an embodiment, the vector is an isolated vector.

The vector can be any vector suitable for producing an antibody and/or binding fragment thereof, including for example vectors described herein. Possible expression vectors include but are not limited to cosmids, plasmids, or modified viruses (e.g. replication defective retroviruses, adenoviruses and adeno-associated viruses).

A further aspect is a recombinant cell producing the antibody and/or binding fragment thereof herein disclosed or the vector herein disclosed.

The recombinant cell can generated using any cell suitable for producing a polypeptide, for example suitable for producing an antibody and/or binding fragment thereof.

Suitable host cells include a wide variety of prokaryotic and eukaryotic host cells. For example, the proteins of the invention may be expressed in bacterial cells such as *E. coli*, insect cells (using baculovirus), yeast cells or mammalian cells.

More particularly, bacterial host cells suitable for producing recombinant antibody producing cells include *E. coli, B. subtilis, Salmonella typhimurium*, and various species within the genus *Pseudomonas, Streptomyces*, and *Staphylococcus*, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the β-lactamase (penicillinase) and lactose promoter system, the trp promoter and the tac promoter. Representative selectable markers include various antibiotic resistance markers such as the kanamycin or ampicillin resistance genes. Suitable expression vectors include but are not limited to bacteriophages such as lambda derivatives or plasmids such as pBR322, the pUC plasmids pUC18, pUC19, pUC118, pUC119, and pNH8A, pNH16a, pNH18a, and Bluescript M13 (Stratagene, La Jolla, Calif.).

Suitable yeast and fungi host cells include, but are not limited to *Saccharomyces cerevisiae, Schizosaccharomyces pombe*, the genera *Pichia* or *Kluyveromyces* and various species of the genus *Aspergillus*. Examples of vectors for expression in yeast *S. cerivisiae* include pYepSec1, pMFa, pJRY88, and pYES2 (Invitrogen Corporation, San Diego, Calif.). Protocols for the transformation of yeast and fungi are well known to those of ordinary skill in the art.

Suitable mammalian cells include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573), NS-1 cells and any derivatives of these lines.

In an embodiment, the mammalian cells used to produce a recombinant antibody are selected from CHO, HEK293 cells or Freestyle™ 293-F cells (Life technologies). FreeStyle 293-F cell line is derived from the 293 cell line and can be used with the FreeStyle™ MAX 293 Expression System, FreeStyle™ 293 Expression System or other expression systems.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences.

In an embodiment, the vector is designed for production of light chain or IgG1 heavy chain.

Suitable insect cells include cells and cell lines from *Bombyx* or *Spodotera* species. Baculovirus vectors available for expression of proteins in cultured insect cells (SF 9 cells) include the pAc series and the pVL series.

The recombinant expression vectors may also contain genes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

"Operatively linked" is intended to mean that the nucleic acid is linked to regulatory sequences in a manner which allows expression of the nucleic acid. Suitable regulatory sequences may be derived from a variety of sources, including bacterial, fungal, viral, mammalian, or insect genes. Selection of appropriate regulatory sequences is dependent on the host cell chosen and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In an embodiment, expression of the antibody or binding fragment thereof is under the control of an inducible promoter. Examples of inducible non-fusion expression vectors include pTrc (28) and pET 11d.

The recombinant expression vectors may also contain a marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest. Other selectable markers include fluorescent proteins such as GFP which may be cotransduced with the nucleic acid of interest.

Yet another aspect is a composition comprising the antibody and/or binding fragment thereof, the nucleic acid herein disclosed or the recombinant cell herein disclosed, optionally in combination with a suitable diluent or carrier.

The composition can be a lyophilized powder or aqueous or non-aqueous solution or suspensions, which may further contain antioxidants, buffers, bacteriostats and solutes. Other components that may be present in such compositions include water, surfactants (such as Tween), alcohols, polyols, glycerin and vegetable oils, for example.

Suitable diluents for nucleic acids include but are not limited to water, saline solutions and ethanol.

Suitable diluents for polypeptides, including antibodies or fragments thereof and/or cells include but are not limited to saline solutions, pH buffered solutions and glycerol solutions or other solutions suitable for freezing polypeptides and/or cells.

The composition can further comprise stabilizing agents, for example reducing agents, hydrophobic additives, and protease inhibitors which are added to physiological buffers.

In an embodiment, the polypeptide is comprised in the solution at a concentration of about 0.5 mg/mL or higher.

Another aspect is an immunoassay comprising the antibody and/or binding fragment thereof herein disclosed as further described below.

In an embodiment, the immunoassay is an enzyme linked immunosorbent assay (ELISA). For example, the ELISA is a sandwich ELISA. In an embodiment the assay is a proximity ligation assay (PLA). In an embodiment, the assay is an immunoprecipation optionally combined with immunoblot detection. In an embodiment, the immunoassay is combined with a mass spectrophometric assay. In an embodiment, the immunoassay is a particle-based flow cytometric assay.

As described in the Examples, the anti-αKlotho sb106 antibody recognizes both the cellular bound and unbound forms of αKlotho. In cell binding studies, anti-αKlotho sb106 bound to HEK293T cells expressing αKlotho but not its paralog βKlotho (FIG. 2A). The anti-αKlotho sb106 antibody can also immunoprecipitate unbound αKlotho from both human and mouse serum (FIG. 2B). This antibody can immunoprecipitate αKlotho with high affinity and specificity devoid of additional bands.

In an embodiment, the immunoassay is a high throughput diagnostic assay.

III. Methods

Another aspect of the disclosure is a method for producing antibody and/or binding fragment thereof with specific binding affinity to an epitope of a folded αKlotho polypeptide.

In one embodiment, the antibody is isolated from an antibody library. For example, the antibody library can be an antibody phage-display library. In one embodiment, the antibody phage-display library is a human Fab phage-display library.

As described below, high throughput, phage-display technology was used to generate the anti-αKlotho sb106 antibody described in the Examples below. Phage-displayed synthetic antibody libraries were screened with the antigen using established methods [67,75]. Antibody binders (phage-displayed or purified) were tested by ELISAs. Purified antigens for the primary screen and subsequent ELISAs included mouse αKlotho, human FGFR1c or a human FGFR1c/mouse αKlotho complex and were produced or purchased from R&D Systems (human αKlotho). As described in the Examples, the sequence of the Fab's antibody-binding region (complementarity determining regions, or CDRs, of the antibody light and heavy chains) was decoded from the DNA carried by the unique binding phage. The CDR regions randomized in the synthetic antibody library used were light chain 3 (CDR-L3) and heavy chain 1, 2, and 3 (CDR-H1, -H2, -H3). An anti-αKlotho antibody that binds αKlotho with for example at least a binding affinity of 10 nM or 2 nM or less can be isolated using a phage library as described.

In an embodiment, the method further comprises randomizing CDR-L1 and/or CDR-L2.

As described in the Examples below, the anti-αKlotho sb106 antibody was generated by targeting an extracellular region of αKlotho present in both the secreted and membrane-anchored forms of αKlotho. The anti-αKlotho sb106 antibody was obtained from a selection in which a purified complex of mouse αKlotho with human FGFR1c receptor (FGFR1c/αKlotho) was exposed to a synthetic antibody phage-display library.

In an embodiment, αKlotho polypeptide is used to isolate an antibody that specifically binds αKlotho polypeptide from the antibody library. In an embodiment, αKlotho complexed with FGFR1c is used to isolate an antibody that specifically binds αKlotho polypeptide from the antibody library.

In another embodiment, the isolated and purified antibody and/or binding fragment thereof is affinity matured. Affinity maturation can performed as described for the initial selection, with antigen adsorbed to plastic plates, using a for example a phage library comprising variants of the CDR sequences for example as described in Example 8.

A person skilled in the art will appreciate that several methods can be used to produce antibodies and/or binding fragments thereof with specific binding affinity to folded αKlotho. A method that can be used is a phage display method. Briefly, a binary αKlotho-FGF1Rc complex is produced (as described in Example 1) in order to isolate and characterize the antibody and/or binding fragment thereof. Phage from a human Fab phage-displayed library are selected following several rounds of panning. Phage with specific binding affinity to the binary αKlotho-FGF1Rc complex, as determined by ELISA, are sequenced and cloned into vectors designed for production of light chain or heavy chain. The heavy chain can be for example an IgG, or an IgG isotype such as an IgG1 or an IgG4. Antigen binding fragments and IgG polypeptides are then affinity purified by using for example Protein A affinity columns.

In another embodiment, a nucleic acid encoding an antibody described herein is expressed in a host cell to make the antibody and/or binding fragment thereof. In an embodiment, the method comprises:
  a. expressing in a host cell a nucleic acid encoding an antibody and/or binding fragment thereof herein disclosed;
  b. culturing the host cell to produce the antibody and/or binding fragment thereof; and
  c. isolating and/or purifying the antibody and/or binding fragment thereof from the host cell.

In some embodiments, a nucleic acid encoding a single chain antibody is expressed. In other embodiments, multiple nucleic acids are expressed, for example encoding a nucleic acid encoding an antibody light chain and a nucleic acid encoding an antibody heavy chain.

Suitable host cells and vectors are described above. Vectors and nucleic acids encoding an antibody described herein may be introduced into mammalian cells via conventional techniques such as calcium phosphate or calcium chloride co-precipitation, DEAE-dextran mediated transfection, lipofectin and other liposome based transfection agents, electroporation or microinjection.

Nucleic acid encoding an antibody described herein may be directly introduced into mammalian cells using delivery vehicles such as retroviral vectors, adenoviral vectors and DNA virus vectors.

As described in the Examples, the sb106 antibody was tested in cells and animal models as follows: the antibody was screened in cultured cells expressing native αKlotho or transfected with αKlotho, in rodents (mice and rats), and in human plasma and urine samples from normal individuals and patients with CKD. The procedures tested included immunoblot, immunoprecipitation, immunohistochemistry, immunocytochemistry, and fluorescence-activated cell sorting (FACS).

The ability of the antibody and/or binding fragment herein disclosed to precipitate soluble αKlotho can be determined using a sequential immunoprecipitation-immunoblot assay as described in Example 6.

A further aspect is an assay for detecting αKlotho polypeptide in a sample the assay comprising:
 a) contacting a sample with the antibody or binding fragment described herein under conditions to form an antibody: αKlotho complex; and
 b) detecting the antibody:αKlotho complex.

In an embodiment, the assay is for detecting folded αKlotho and the assay is performed under non-denaturing or mildly denaturing conditions.

In an embodiment, the complex is detected directly for example wherein the antibody is labeled with a detectable tag or fusion moiety. In an embodiment, the complex is detected indirectly using a secondary antibody specific for the antibody:αKlotho complex.

In an embodiment, the assay is an immunoprecipitation, immunoblot, immunohistochemistry or immunocytochemistry proximity ligation assay (PLA), mass spectroscopy-based techniques and fluorescence-activated cell sorting (FACS), proximity ligation assay (PLA), and mass spectroscopy-based techniques. The antibodies described herein are efficient for immunoprecipitating αKlotho polypeptide and are much better than antibodies such as KM2076 and others [13] tested by the inventors.

In one specific embodiment, the method assay is a sequential immunoprecipitation-immunoblot (IP-IB). The IP-IB can be performed for example as described in the Examples below.

In an embodiment, the method is for detecting soluble αKlotho, for example wherein the sample is a biological fluid.

A further aspect includes a method for detecting and/or measuring soluble αKlotho the method comprising:
 a) contacting a sample, the sample being a biological fluid, with the antibody or binding fragment described herein under conditions to form an antibody: soluble αKlotho complex; and
 b) detecting and/or measuring the antibody:soluble αKlotho complex.

Detecting can be performed using methods that are qualitative or measured using quantitative methods, for example by comparing to a standard or standard curve.

In an embodiment, the biological fluid sample is blood, or a part thereof such as serum or plasma, or urine.

In an embodiment, the assay is a diagnostic assay. For example, as detailed in Example 7, the IP-IB assay comprising the antibody and/or binding fragment thereof herein disclosed is evaluated to test its linearity and to determine whether it can reliably detect serum αKlotho levels in chronic kidney disease (CKD) patients. As such, pre-determined amounts of recombinant αKlotho varying from grade 1 CKD to grade 5 CKD along with serum from a healthy volunteer are used. The results show an incremental relationship between the serum levels and the CKD stage. Further, as shown in FIG. 6B, the IP-IB assay with sb106 shows an important reduction of urinary αKlotho in patients with CKD.

Yet another aspect relates to a method for screening, for diagnosing or for detecting kidney insufficiency condition selected from chronic kidney disease (CKD) and acute kidney injury (AKI) in a subject, the method comprising:
 a. measuring the level of αKlotho in a sample from a subject optionally using an antibody or assay herein disclosed; and
 b. comparing the level of αKlotho in the sample with a control,
 wherein a decreased level of αKlotho in the sample compared to the control is indicative that the subject has a kidney condition selected from CKD or AKI.

In an embodiment, the control is a control value derived from a group of subjects without CKD or AKI e.g. normal controls.

In an embodiment, the CKD is early CKD, optionally stage 1, stage 2, stage 3, stage 4, stage 5 or stage 6 CKD.

An additional aspect of the disclosure is a method for prognosticating CKD progression or AKI progression or lack thereof (e.g. recovery or worsening of disease), or extra-renal complication in CKD, which is assessed by measuring the level of αKlotho deficiency.

Accordingly an aspect is a method of prognosticating a likelihood of recovery after AKI, the method comprising:
 a. measuring a level of αKlotho in a sample from a subject; and
 b. comparing the level of αKlotho in the sample with a control, for example a control value derived from a group of subjects that did not recover or progressed,
 wherein an increased level of αKlotho in the sample compared to the control is indicative that the subject has an increased likelihood of recovery after AKI.

In an embodiment, the control is a control value derived from a group of subjects that did recover and a decreased level of αKlotho in the sample compared to the control is indicative that the subject has a decreased likelihood of recovery after AKI and/or an increased likelihood of disease progression.

Another aspect is a method for prognosticating a likelihood of long term complications after AKI, the method comprising:
 a. measuring a level of αKlotho in a sample from a subject; and
 b. comparing the level of αKlotho in the sample with a control, for example a control value derived from a group of subjects with long term complications or with increased number of long term complications,
 wherein an increased level of αKlotho in the sample compared to the control is indicative that the subject has a increased likelihood of having fewer long term complications after AKI In an embodiment, wherein the control is a control value derived from a group of subjects without long term complications or with fewer long term complications, an decreased level of αKlotho in the sample compared to the control is indicative that the subject has a increased likelihood of having long term complications or an increased number of long term complications after AKI.

A further aspect is a method for prognosticating the likelihood of progression of CKD, the method comprising:
a. measuring a level of αKlotho in a sample from a subject; and
b. comparing the level of αKlotho in the sample with a control,
wherein an increased level of αKlotho in the sample compared to the control, for example wherein the control is a control value derived from a group of subjects that or example a control value derived from a group of subjects that did not recover or progressed is indicative that the subject has an increased likelihood of recovering from CKD.

In an embodiment, the control is a control value derived from a group of subjects that did recover and a decreased level of αKlotho in the sample compared to the control is indicative that the subject has a decreased likelihood of recovery after CKD and/or an increased likelihood of disease progression.

Yet another aspect is a method for prognosticating extra-renal complications in CKD, the method comprising:
a. measuring a level of αKlotho in a sample from a subject; and
b. comparing the level of αKlotho in the sample with a control,
wherein an increased level of αKlotho in the sample compared to the control is indicative that the subject has a higher likelihood of having fewer extra-renal complications related to CKD.

In an embodiment, wherein the control is a control value derived from a group of subjects without extra-renal complications or with fewer extra-renal complications, an decreased level of αKlotho in the sample compared to the control is indicative that the subject has a increased likelihood of having long term complications or an increased number of extra-renal complications after CKD.

A further aspect is a method for monitoring a subject with a kidney insufficiency condition such as CKD or AKI the method comprising:
a. measuring a level of αKlotho in a sample from a subject; and
b. comparing the level of αKlotho in the sample with a previous reference sample other control,
wherein an increased level of αKlotho in the sample compared to the previous reference sample or other control is indicative that the subject has an ameliorating kidney condition and a decreased level of αKlotho in the sample compared to the previous reference sample or other control is indicative that the subject has a worsening kidney condition.

The sample can for example be taken after the subject has received a treatment and compared for example to a pre-treatment sample. Alternatively the patient can be monitored after a repeating interval to assess for example if treatment or other intervention is necessary. In an embodiment, the test is repeated and plotted to assess the subject's progression.

In an embodiment, the sample is a biological fluid such as blood, or a fraction thereof such as plasma or serum and the method is for example detecting soluble αKlotho. In an embodiment the biological fluid is urine.

In another embodiment, the sample is selected from a fresh sample such as a fresh biological fluid sample or tissue sample (e.g. including not frozen or one time frozen (e.g. frozen a single time at the time of obtaining the sample)) and a repeat frozen sample (e.g. frozen and thawed and frozen biological fluid sample or repeat frozen tissue sample). In an embodiment, the sample is a fixed sample such as a mildly fixed sample wherein the fixation induces limited denaturation and/or unfolding.

In an embodiment, the level of αKlotho is measured using an antibody or binding fragment described herein.

The methods disclosed herein to diagnose, detect or monitor a kidney disease or prognosticate a kidney disease complication, can be used in addition to or in combination with traditional diagnostic techniques for kidney disease.

IV. Kits

A further aspect relates to a kit comprising i) an antibody and/or binding fragment thereof, ii) a nucleic acid, iii) composition or iv) recombinant cell described herein disclosed, comprised in a vial such as a sterile vial or other housing and optionally a reference agent and/or instructions for use thereof.

In an embodiment, the kit is a diagnostic kit and the instructions are directed to a method described herein.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

A synthetic antibody library was screened and an antigen-binding fragment (Fab) with high affinity for human and rodent αKlotho was generated. This novel antibody, sb106, was characterized using recombinant proteins, cultured cells, and body fluids and tissues from humans and rodents. αKlotho levels in serum and urine in human and rodents can be accurately quantified, and it is demonstrated that both serum and urine αKlotho are dramatically reduced in early human CKD. The sb106 antibody is specific to the α-form of Klotho and is the first known one to successfully pull down αKlotho from patient serum samples, in a clean and specific manner, as compared to currently commercially available αKlotho detection reagents. In cells, it can immunoprecipitate αKlotho and label it by immunocytochemistry. In animals, the antibody is efficient at immunoprecipitating αKlotho from plasma. The ability of the sb106 antibody to detect small quantities of αKlotho from biological fluids makes it a valuable reagent for diagnosis of diseases where the level of αKlotho is abnormal. Moreover, sb106 antibody is valuable as a research reagent in studies of physiologic and pathologic states that involve any FGF23-mediated signaling pathways. It can be used in specific assays for soluble αKlotho in human and rodent samples such as serum using a variety of techniques such as enzyme-linked immunosorbent assay (ELISA), proximity ligation assay (PLA), and mass spectroscopy-based techniques.

Example 2

Preparation of the Binary αKlotho-FGFR1c Complex

The ligand-binding domain of human FGFR1c (D142 to R365) was expressed in E. coli, refolded in vitro from inclusion bodies, and purified by published methods [72,73]. The extracellular domain of murine αKlotho (A35 to K982) was expressed in HEK293 cells with a C-terminal FLAG tag, and the binary complex of the αKlotho ectodomain and the FGFR1c ligand-binding domain was prepared as described [9].

Isolation and Characterization of sb106

Sb106 was isolated from a synthetic human Fab phage-displayed library (Library F)[74]. Binding selections, phage ELISAs and Fab protein purification were performed as described[67,75,76]. Briefly, phage from library F were cycled through rounds of panning with the binary complex of αKlotho extracellular domain and FGFR1c ligand-binding domain on 96-well Maxisorp Immunoplates (Fisher Scientific, Nepean, ON, Canada) as the capture target. After 5 rounds of selection, phage were produced from individual clones grown in a 96-well format and phage ELISAs were performed to detect specific binding clones. Clones that showed binding were subjected to DNA sequencing. A competitive binding ELISA was performed by pre-incubating sb106-phage with serial dilutions of soluble human αKlotho (50-0.0005 nM×1 hour) prior to binding to an ELISA plate coated with human αKlotho. The genes encoding for variable heavy and light chain domains of sb106 were cloned into vectors designed for production of light chain or IgG1 heavy chain, respectively, and sb106-IgG was expressed from 293F cells (Invivogen, San Diego, Calif. USA). Fab and IgG proteins were affinity-purified on Protein A affinity columns (GE Healthcare, Mississauga, ON, Canada).

Purification of Proteins

The binary complex of FGFR1c ligand-binding domain and murine αKlotho ectodomain (referred to as αKlotho-FGFR1c complex) was prepared by a published protocol[9]. The N-terminally hexahistidine tagged, mature form of human FGF23 (Y25 to I251) was expressed in E. coli and purified by published protocols [73,74,77].

Analysis of Fab Binding to αKlotho-FGFR1c Complex by SPR Spectroscopy

Real time protein-protein interactions were measured using a Biacore 2000 surface plasmon resonance (SPR) spectrometer (Biacore AB/GE Healthcare) at 25° C. in HBS-EP buffer (10 mM HEPES-NaOH, pH 7.4, 150 mM NaCl, 3 mM EDTA, 0.005% (v/v) polysorbate 20). Proteins were covalently coupled through their free amino groups to carboxymethyl (CM) dextran of research grade CM5 biosensor chips (Biacore AB/GE Healthcare). Proteins were injected over a biosensor chip at a flow rate of 50 µl min$^{-1}$, and at the end of each protein injection (180 s), HBS-EP buffer (50 µl min$^{-1}$) was flowed over the chip to monitor dissociation for 180 s. Injecting 2.0 M NaCl in 10 mM sodium acetate, pH 4.5, or 10 mM sodium/potassium phosphate, pH 6.5 regenerated the chip surface in between protein injections. The data were processed with BiaEvaluation software version 4.1 (Biacore AB/GE Healthcare). For each protein injection, the non-specific SPR responses recorded for the control flow channel were subtracted from the responses recorded for the sample flow channel.

To examine whether Fabs selected by ELISA bind to the αKlotho-FGFR1c complex, the binary receptor complex was immobilized on a CM5 chip (~42 fmol mm$^{-2}$ of chip flow channel). To control for non-specific binding, bovine β-glucuronidase (Sigma-Aldrich), which is structurally related to each of the two extracellular glycosidase-like domains of αKlotho, was coupled to the control flow channel of the chip (~45 fmol mm$^{-2}$ of flow channel). 100 nM of each Fab were injected over the chip. As a control, binding of FGF23 to the immobilized αKlotho-FGFR1c complex was examined.

To test if the Fabs can compete with FGF23 and/or binding to the αKlotho-FGFR1c complex, FGF23 was immobilized on a CM5 chip (~16 fmol mm$^{-2}$ of chip flow channel). FHF1B, which is structurally similar to FGFs but has no FGFR binding[77], was used as control for non-specific binding (~15 fmol mm$^{-2}$ of control flow channel). 100 nM of Fab mixed with 10 nM of αKlotho-FGFR1c complex (HBS-EP buffer) was injected over the chip. For control, the binding competition was carried out with FGF23 as the competitor in solution.

Cell Culture, Animal and Human Studies

Cell lines: normal rat kidney (NRK) cells with native αKlotho expression (ATCC, Manassas, Va., USA), and HEK293 cells transfected with vector only, full-length transmembrane murine αKlotho, extracellular domain of murine αKlotho with C-terminal FLAG tag, or full-length murine βKlotho[78]. Cells were cultured at 37° C. in a 95% air, 5% $CO_2$ atmosphere, passed in high-glucose (450 mg/dl) DMEM supplemented with 10% fetal bovine serum, penicillin (100 U/ml), and streptomycin (100 mg/ml).

Animal studies were approved by the University of Texas Southwestern Medical Center Institutional Animal Care and Care Committee. All animals were housed in the Animal Resource Center and experiments were performed in fully approved laboratories. Species used include: Sprague-Dawley rats (Harlan. Indianapolis, Ind.), Klotho transgenic overexpressors (Tg-Klotho; EFmKL46 line)[79], homozygous αKlotho hypomorphic mice (Kl/Kl)[80], and their wild type littermates (129sv background).

Clinical history and routine lab data were obtained from electronic charts. Blood samples from antecubital venipuncture were spun, and the serum was frozen at −80° C. Fresh urine was spun at 4,000 g and the supernatant was frozen at −80° C.

Immunocytochemistry and Immunohistochemistry

HEK293 cells transfected with vector or the stated αKlotho plasmids and seeded (1.8×10$^5$ cells/ml) on 12-well glass cover slips pre-treated with poly-lysine and grown overnight. The cells were washed (4° C. PBS×3), fixed with 3% paraformaldehyde (4° C.×10 min), washed (ice cold PBS×3), blocked with 1% BSA (PBS 44° C.×10 min), incubated with sb106-Fab (5 µg/ml in 1% BSA, PBS) washed (PBS 4° C.×5), incubated with anti-FLAG-Alexa488 (Cell Signaling; diluted 1:400 in PBS containing 1% BSA; 1 hour; 20° C.), washed (PBS; 4° C.×4), and then inverted onto glass slides containing a drop of antifade with DAPI (Invitrogen) and dried at room temperature in the dark. After 24 hours, the slides were stored at −20° C. Images were obtained on a WaveFX spinning disc confocal microscope.

The parathyroid and thyroid (en bloc with the trachea) were from adult Sprague Dawley rats. For non-fixed fresh parathyroids, tissues were embedded in OCT medium and frozen with isopentane pre-cooled in liquid $N_2$ immediately. For fixed parathyroid samples, tissue was immersed in 4% paraformaldehyde in PBS pH 7.4 at 4° C. overnight, washed with PBS, and embedded in OCT medium and frozen with isopentane pre-cooled in liquid $N_2$. Four µm thick cryostat sections were made, washed in PBS (15 min), and permeabilized in 0.1% TritonX-100 (10 min). For labeling, sections were blocked (PBS, 1.5% BSA, 10% goat serum; 40 min) and incubated with the primary antibody sb106 (21 µg/ml in blocking solution; 4° C. overnight). After washing (PBS), sections were incubated with the Alexa 546 goat anti-human IgG (1:800 dilution, Invitrogen) for 1 hour at room temperature. After additional washes with PBS, the sections were fixed with 4% paraformaldehyde in PBS, washed with PBS, and mounted and visualized with a Zeiss LSM510 microscope.

Example 3: αKlotho Assays and Detailed Methods

The ELISA was performed as instructed by the manufacturer (Immuno-Biological Laboratory, Japan). For the IP-IB assay, typically 50 µl of serum or urine were diluted with KRH buffer [25 mM Hepes-NaOH (pH 7.4), 120 mM NaCl, 5 mM KCl, 1.2 mM MgSO4, 1.3 mM CaCl2), 1.3 mM KH2PO4] to a final volume of 0.5 ml incubated with 2 µg of sb106-Fab overnight at 4° C. in low binding, siliconized tubes. Sepharose beads (50 µL) conjugated with anti-FLAG antibody (50% v/v) prewashed 3× with KRH buffer were added, incubated (4° C.×2 h), and washed (KRH—500 µl per tube×3; 22° C.). The immune complex was eluted with 2×SDS sample loading buffer (50 µl; 100° C.×3 min; 4° C.×3 min; spun), and fractionated by SDS-PAGE, transferred to nitrocellulose membranes and blotted with anti-KL1 antibody (KM2076, 1:4000 or 3.1 mg/mL, 1:10000 dilution) and diluent (Dako#53022, Carpinteria, Calif., USA) overnight (4° C., rocker). The membrane was washed (×3, Tris-buffered saline with 0.1% Tween; TBS-T), exposed to anti-rat IgG2A (LSBio cat#LS-059051, 1:20000 in 5% milk/2% goat serum/TBS-T×1 h) and washed (×3 TBS-T). For chemiluminescence, the membrane was covered with SuperSignal West Femto Maximum Sensitivity substrate (Thermo Scientific, Rockford, Ill., USA) and exposed for 30-90 s. The 130-kD bands were scanned, and density was compared with internal control samples of know amount of Klotho using Adobe Photoshop CS4.

Example 4: Identification of an Anti-αKlotho Synthetic Fab

After rounds of biopanning of a phage-displayed synthetic Fab library on recombinant αKlotho ectodomain complexed with the ligand-binding domain of fibroblast growth factor receptor (FGFR)1c, several binding phages were identified. Clone sb106 (FIG. 1A) was chosen for further characterization. In phage ELISA (FIG. 1B), sb106-phage bound to both human and mouse αKlotho, demonstrating cross species reactivity, and to either αKlotho alone or in complex with FGFR1c, indicating that its epitope is not obscured by co-receptor complex formation. Sb106-phage did not bind to FGFR1c alone, neutravidin (NAV) or bovine serum albumin (BSA). Sb106 binds to human αKlotho with affinity in the single-digit nanomolar range (1050=1.7 nM, FIG. 1C). Sb106-Fab also binds with high affinity to the binary αKlotho-FGFR1c complex immobilized on a biosensor chip (FIG. 7A) and it does not interfere with ternary complex formation between FGF23, αKlotho and FGFR1c (FIG. 7B).

Example 5: Characterization of the Anti-αKlotho Fab sb106

Using the unique CDR sequences of sb106 (FIG. 1A), both Fab and full-length IgG proteins were produced (e.g. Fab was produced in bacterial cells and IgG proteins in 293F cells). Sb106 was highly reactive against αKlotho under native conditions. Immunoblot signals under denaturing conditions against mouse, rat, and human kidney tissue were weak, but in samples from transgenic mice overexpressing αKlotho[79], sb106-Fab detected a band corresponding to the full-length extracellular domain of αKlotho (FIG. 2A). In cultured cells, sb106-Fab was not able to detect αKlotho in immunoblots under denaturing conditions with lysates from NRK cells expressing native αKlotho but it was able to detect overexpressed antigen in cell lysates from HEK293 cells transfected with αKlotho (FIG. 2B). In immunohistochemistry with freshly frozen unfixed rat parathyroid tissue (and other tissues known to express αKlotho, sb106-IgG detected αKlotho but the same tissue was negative when fixed (FIG. 2C), suggesting that sb106 binds to the natively folded FGFR1-αKlotho complex (FIG. 1B). In immunocytochemical stains with freshly fixed cells, unequivocal staining was obtained in HEK293 cells heterologously overexpressing αKlotho but not in cells overexpressing βKlotho (FIG. 2D). The cells were seeded at $1.8 \times 10^5$/ml on 12-well glass cover slips treated with poly-lysine and grown overnight. Cells were washed 3 times with ice cold PBS, fixed for 10 min on ice (3% paraformaldehyde), washed 3 times with cold PBS, blocked for 10 min (1% BSA in cold PBS). Cells were then incubated with sb106-Fab (5 µg/ml in 1% BSA in PBS) for 1 hr. Cells were washed 5 times with cold PBS (2 min each) and then incubated with anti-FLAG-Alexa488 (the C-terminus of the Fab light chain contains a Flag epitope tag) (1:400 in 1% BSA in PBS) for 1 hr, while being protected from light. Cells were washed 4 times with cold PBS (5 min each). The glass coverslips were then inverted onto glass slides containing a drop of antifade reagent with DAPI. Images were collected on a spinning disc confocal microscope. Even in cells overexpressing αKlotho, prolonged fixation greatly diminished or abolished the staining with sb106. These data indicate that sb106 reacts specifically with natively folded human, rat, and mouse αKlotho but not with denatured αKlotho protein.

Example 6: Immunoprecipitation of αKlotho

The ability of sb106-Fab to precipitate soluble αKlotho was tested using a sequential immunoprecipitation-immunoblot (IP-IB) assay. Sb106-Fab pulled down αKlotho from total cell lysates and conditioned cell culture medium and from αKlotho-overexpressing cells (FIG. 3A). The sb106-Fab pull-down was compared with that of an anti-FLAG antibody using soluble αKlotho with a C-terminal FLAG tag in HEK293 cells. Sb106-Fab and anti-FLAG precipitated proteins with the exact same electrophoretic mobilities.

Sb106-Fab precipitated a ~130 kDa protein from human, mouse, and rat sera that reacted with the anti-αKlotho antibody KM2076 (FIG. 3B). IP from urine also showed a ~130 kDa band (FIG. 3B), whereas the post-IP urine samples did not show such a band in immunoblot. To further support the authenticity of the IP-IB band by sb106, the intensity of this band was examined in human sera from a normal individual vs. a patient with CKD stage 5, and sera from a wild type mouse vs. a homozygous αKlotho hypomorph (FIG. 3C). Only the ~130 kDa band (FIG. 3C) was reduced in human advanced CKD and was absent in the αKlotho-deficient mice (kl/kl)[80].

Example 7: αKlotho Levels in Human CKD

The IP-IB method was tested to determine whether it can reliably determine serum αKlotho levels from a single center database of CKD patients. Recombinant human αKlotho was spiked in known amounts to test the linearity of the assay as well as the extrapolated y-intercept. IP-IB was performed with sera from a normal healthy volunteer and a patient with stage 5 CKD spiked with a range of different concentrations of recombinant αKlotho (FIG. 4A). There was graded increase in signal with the incrementally inoculated exogenous αKlotho. The serum from the CKD patient also showed increases in signal with increasing exogenous αKlotho but, at any given concentration of αKlotho, the signal intensity was lower than the normal serum.

Interestingly, the serum from the healthy volunteer gave the same signal in the absence or presence of a protease inhibitor cocktail, whereas the serum from the CKD patient displayed a marked increase in measured αKlotho levels in the presence of a protease inhibitor (FIG. 4B). These findings suggest that while endogenous αKlotho exists in a stable steady state in uremia, the exogenously added αKlotho may undergo proteolysis in uremic serum but not in normal serum. A quantitative summary of the spiking experiment is shown in FIG. 4C. Both healthy and CKD sera showed linear responses to αKlotho inoculation but the signal from CKD sera has a lower slope. When protease inhibitors were included, the slope of the CKD line approached that of the healthy subject without affecting its intercept. Extrapolation to zero inoculation showed that the serum from the normal individual had 31.1 pM αKlotho while that from the CKD patient had 8.5 pM αKlotho. Similar extrapolations were obtained from a number of other subjects with normal renal function or with CKD.

The nature of patients recruited from the CKD clinic resembles the national profile of CKD where diabetes and hypertension predominate (Table 1). Despite the scatter, there is a clear progressive decline of αKlotho with stages of CKD (FIG. 5A). The decrease in serum αKlotho occurred early in CKD, and preceded high FGF23, high PTH, and hyperphosphatemia (Table 1). The IP-IB assay was directly compared with a commercial αKlotho ELISA kit with the same samples (FIG. 5B). Overall, there is a correlation between the two but there is separation on both sides of the line of identity. In fresh samples, the ELISA shows higher values than IP-IB (grey diamonds to the left of the line of identity, FIG. 5B) but in samples that have been through one or more cycles of freeze-thaw, the ELISA values are much lower (black diamonds to the right of the line of identity, FIG. 5B). When the exact same samples were tested by the two methods before and after repeated freeze-thaw, the IP-IB assay gave more stable results while the ELISA values dropped rapidly (FIG. 5C).

Low urinary αKlotho in human CKD patients by directly immunoblotting urine was previously described[12]. The IP-IB assay with sb106-Fab showed dramatic reduction of urinary αKlotho in CKD patients (FIG. 6A). In contradistinction from serum, the ELISA yielded more comparable values to the IP-IB assay in the urine but the magnitude of decrease in αKlotho concentration is more dramatic when detected by the IP-IB assay than by ELISA (FIG. 6B). These results show that human CKD is a state of αKlotho deficiency in both serum and urine.

Hence using an immunoprecipitation-immunoblot (IP-IB) assay, both the serum and urinary levels of full-length soluble αKlotho was measured in humans and it was established that human CKD is associated with αKlotho deficiency in serum and urine. αKlotho levels were detectably lower in early CKD preceding disturbances in other parameters of mineral metabolism and levels progressively declined with CKD stages. Exogenously added αKlotho is inherently unstable in the CKD milieu.

Antibody-based reagents are valuable tools in both research and clinical settings for detection of proteins, protein isolation and purification, and numerous downstream applications. The commercial reagents available for αKlotho detection are limiting; for example there are no antibodies for specifically detecting natively folded αKlotho protein. Moreover, the commercial ELISA kit for αKlotho detection yields highly variable results.

Synthetic antibodies with designed antigen-binding sites can be fine-tuned and tailored for molecular recognition of vast repertoires of targets. Coupled with in vitro phage-display, selections are performed in the absence of tolerance mechanisms that eliminate self-reactive antibodies. Selections with an antibody library yielded sb106, an antibody with specificity for natively folded human, mouse and rat αKlotho.

In addition to its role in mineral metabolism, soluble αKlotho circulates in many bodily fluids and has multiple "house-keeping" functions that maintain cellular integrity throughout the body. Although the mechanism of action of soluble αKlotho remains poorly understood, the biologic impact of αKlotho deficiency is unequivocally shown[81]. αKlotho transcripts are present in multiple organs but the kidney by far has the highest expression[80]. CKD is a state of multiple metabolic derangements and is a complex syndrome from accumulation of under-excreted endogenous and exogenous toxins as well as deficiency in substances responsible for health maintenance.

There is evidence in experimental animals that both AKI and CKD are states of systemic αKlotho deficiency. Not only is this an early and sensitive biomarker, restoration of αKlotho can ameliorate the renal dysfunction. Independent from its renoprotective effects, αKlotho can also reduce the extrarenal complications in CKD[12,82]. Based on the preclinical data, anti-αKlotho antibody may have both diagnostic and prognostic value.

Validation of the IP-IB Assay and Comparison with the Commercial ELISA

Available commercial assays for αKlotho have no consistent correlation between them[46, 83]. Studies in healthy humans and CKD patients based on one ELISA[58] have yielded contradictory results. The absolute levels of αKlotho in normal and CKD ranged from 0.4[47] to over 2000 pg/ml[41] with most readings in the mid to high hundreds [48, 50, 55, 58-60,83]. Based on this assay, αKlotho levels have been described to be low[48, 52, 54, 57-60], no relationship to[40, 41, 50, 51, 53] or even increased[44, 47] with decreasing glomerular filtration rate (GFR). Likewise, αKlotho levels have been reported as not changed or decreasing with age[42, 53, 58, 59]. This renders the interpretation of human αKlotho data nearly impossible, and the collective data derived from different centers will have no value.

A high affinity synthetic antibody that recognizes αKlotho in its natively folded conformation (FIGS. 1-3) was generated. Sb106-Fab or IgG pulls down αKlotho from cell lysate, culture medium, serum, and urine. Additional bands may be shorter fragments of αKlotho but the intensity of these bands did not decrease in the kl/kl mice arguing against this possibility. The ~130 kDa band has been analyzed which is full length soluble αKlotho; something that the ELISA cannot achieve.

The linearity of the spiking experiment indicates that all the inoculated αKlotho is detected (FIG. 4). An unexpected finding was that exogenously added recombinant αKlotho is proteolytically degraded in uremic serum whereas no such phenomenon was observed in normal sera. This challenges the view that the low αKlotho in kidney disease stems solely from decreased production and opens up additional mechanisms and new avenues for investigation. In addition to uncovering new mechanisms of αKlotho deficiency in CKD, this may have significant implications in terms of recombinant αKlotho replacement.

There is graded reduction in serum αKlotho with advancing CKD (FIG. 5A). The coefficient of variation of the IP-IB assay was 4% for serum and 7% for urine. The IP-IB assay also showed very low urinary αKlotho in advanced CKD (FIG. 6). In fact, the reduction in urinary αKlotho is more dramatic than that in serum and may represent a more sensitive marker for CKD.

Both IP-IB and the commercial ELISA detected the low urine αKlotho in CKD, although the absolute levels of αKlotho are much higher with the ELISA assay and the percent reduction is not the same as with the IP-IB assay. With drastic reduction in urinary αKlotho levels in CKD, the two assays yielded the same conclusion with quantitative differences. The situation in serum is different. Although there is overall positive correlation, the comparison of the two assays completely segregated into two groups (FIG. 5B). The fresh samples showed higher readings for the ELISA while the stored samples yielded extremely low results with the ELISA. One possibility is that the ELISA is measuring αKlotho and some other reacting proteins in fresh samples. While the IP-IB assay did lose some efficacy with repeated freeze-thaw, this is a much more serious problem with the ELISA.

Another advantage of the IP-IB assay is that it can measure αKlotho in both humans and rodents equally well, whereas the use of the currently available ELISA in rodent can potentially be problematic as it detects very high circulating αKlotho levels in rats with CKD which is a state of pan-αKlotho deficiency.[68]

Example 8

Additional CDR sequences are provided in Table 2. Homologous mutations were introduced at each amino acid position, meaning that for each position either the original amino acid was retained or the closest "homolog" to that amino acid (e.g. conservative amino acid change) was introduced and a new Fab-phage library was constructed. Selections were performed using the new library using the alphaKlotho-FGFR1c complex as an antigen. Clones that bound to the antigen were isolated and sequenced and are shown in Table 2. The binding affinity is expected to be similar or better than Sb106.

Example 9

Human Studies

Nine human subjects (49.066.2 years) who underwent right heart catheterization were enrolled for this study. During right heart catheterization, suprarenal and infrarenal vena caval blood samples were obtained and sera were immediately separated after centrifugation at 4° C. and stored at −80° C. for future study. Serum αKlotho was determined by immunoprecipitation-immunoblot assay described herein. Briefly, 0.1 ml serum was immunoprecipitated with a synthetic anti-αKlotho Fab (sb106) and immune complex was eluted with Laemmli sample buffer, and subject to immunoblot with KM2076 antibody. The specific signals on the autoradiograms based on 130 kD mobility were quantified with ImageJ Program (National Institutes of Health (NIH), Bethesda, Md.).

Animal Studies

αKlotho hypomorphic (kl/kl) mice, kl/kl mice and their wild-type (WT) littermates were maintained at the Animal Research Center at the University of Texas Southwestern Medical Center. Currently all mice are 129 S1/SVImJ (129 SV) background age from 6 to 8 weeks. Normal Sprague-Dawley (SD) rats (220-250 g body weight) were purchased from Charles River Laboratories (Wilmington, Mass.). For αKlotho clearance study, rats underwent bilateral nephrectomy (anephric rats) or laparotomy with manual manipulation of the kidneys (sham rats). Rats or mice were intravenously or intraperitoneally injected once with labeled full extracellular domain of recombinant mouse αKlotho protein (rMKI) (R&D Systems, Minneapolis, Minn.) at a dose of 0.1 mg/kg body weight. To examine if secretases modulate blood αKlotho, doxycline hyclate (Sigma-Aldrich, St. Louis, Mo.), an α-secretase inhibitor at 25 mg/kg/day, and/or β-secretase inhibitor III (Calbiochem, Billerica, Mass.) at 2.5 mg/kg/day were intraperitoneally injected into normal WT mice daily for 2 days, blood and kidneys were harvested at 48 hours to determine serum and renal αKlotho.

Antibodies

Rat monoclonal anti-human Klotho antibody, KM20761,2 was used for immunoblotting and immunoelectron microscopy; and the synthetic anti-αKlotho antibody sb10663 was used for immunoprecipitation of serum Klotho.

Clearance of Labeled αKlotho in Rats and Mice

Normal Munich Wistar rats (220-250 g BW) were anesthetized with Inactin (100 mg/kg BW), and a bonus of labeled αKlotho was injected through the jugular vein (0.1 mg/kg BW). For the experiment of injection of 125I-labeled αKlotho or 125I-labeled albumin, fluid collection by free-flow micropuncture of Bowman's space, and proximal convoluted tubules was performed using our published methods. In brief, the left kidney was exposed, and the left ureter was catheterized for urine collection. Proximal tubules were identified by their characteristic configuration after lissamine green dye injection and punctured with glass capillaries. The volume of fluid was measured in a calibrated constant-bore glass capillary. The radioactivity of fluids was determined by scintillation accounting and normalized to fluid volume. At specified time points, blood was drawn from retro-orbital venous sinus, and spot urine was collected. 125I-labeled αKlotho or 125I-labeled albumin in collected urine and serum was quantified by scintillation counting. Homogenates of different organs were made and radioactivity in organ homogenates was measured by scintillation counting, and normalized to protein in organ homogenates. Organ sections (10 mm) were subjected to autoradiography Immunoelectron Microscopy Mouse recombinant Klotho protein (0.1 mg/kg BW) was intraperitoneally injected once into kl/kl mice and mice were sacrificed 24 hours after injection. Kidneys were harvested and fixed with 2.5% paraformaldehyde via aortic perfusion, removed, and post-fixed in 4% paraformaldehyde (4° C. for 4 hours). Immunogold labeling of ultrathin frozen tissue sections was performed as described.21 Kidney cortex was infiltrated with 2.3 M sucrose overnight, frozen in liquid nitrogen, and 70-80-nm-thick sections were made (Ultramicrotome Reichert Ultracut E; Leica Microsystems, Wetzlar, Germany) and mounted on Formvar-coated nickel grids. The sections were incubated with KM2076 antibody and followed by incubation with gold conjugated protein A (10-nm gold particles, Sigma-Aldrich) for 60 minutes. After staining with uranyl acetate, sections were visualized with Jeol 1200 EX transmission electron microscope (Jeol Ltd., Akishima, Japan).

Results

The role of the kidney in circulating αKlotho production and handling was examined. Serum levels of αKlotho protein in suprarenal and infrarenal vena cava of normal rats by direct puncture and human subjects who underwent right heart catherization. All patients had eGFR≥60 ml/min/1.73 m². Similar infrarenal-to-suprarenal increment in caval αKlotho level was observed in both rat and human serum samples. Serum αKlotho levels were plotted against serum erythropoietin, a well-known renal-derived hormone, and it was found that as serum erythropoietin rose, and serum creatinine (SCr) decreased from infrarenal-to-suprarenal inferior vena cava, whereas αKlotho increased indicating that the kidney secretes αKlotho into the circulation.

When both kidneys were removed from rats, serum αKlotho level dropped significantly to about half the normal level in one day. The anephric state did not permit studies to continue for longer than 40-50 hours.

The method of αKlotho clearance from circulation was investigated. The levels of circulating exogenous αKlotho protein in anephric rats were similar to those in normal rats immediately after injection, but the half-life of exogenous αKlotho protein in normal rats was much shorter than that in anephric rats and the half-life of endogenous αKlotho upon nephrectomy closely approximates that of exogenous αKlotho in the anephric rats. Further experiments examining the anatomic fate of intravenous injected exogenous labeled αKlotho supported that the kidney may be a major organ of αKlotho uptake as well as its excretion Injected labeled αKlotho protein was prominently distributed in the kidney and spleen, sparsely in the heart, and not detectable in aorta, brain, and muscle. Further experiments tracking clearance of radioactively labelled exogenous αKlotho in serum and urine, supported that αKlotho protein is cleared from blood through the kidney to the urine.

Based on these and further experiments, it was determined that the (1) the kidney produces and releases soluble αKlotho into the systemic circulation by secretases-mediated shedding of the ectodomain of αKlotho, (2) the kidney is an important organ to clear soluble αKlotho from the circulation, (3) αKlotho traffics across renal tubules from basolateral to intracellular location and is then secreted across the apical membrane into the urinary lumen.

TABLE 1

Characteristics of human subjects

| Subject | n | Age | Gender (M/F) | PCr (mg/dl) | Serum Pi (mg/dl) | Serum $HCO_3^-$ (mM) | Serum PTH (pg/ml) | FGF23 (pg/ml) | 25(OH) Vitamin D (ng/ml) | Etiology of CKD (number subjects*) |
|---|---|---|---|---|---|---|---|---|---|---|
| Healthy | 34 | 50 ± 17 | 14/20 | 0.8 ± 0.2 | 3.6 ± 0.6 | 23 ± 2 | 59 ± 25 | 30 ± 10 | 32 ± 10 | None |
| CKD1 | 10 | 43 ± 10 | 7/3 | 0.8 ± 0.1 | 3.9 ± 0.5 | 25 ± 2 | 47 ± 19 | 61 ± 23 | 26 ± 7 | DM (1) HTN (3) GN (7) |
| CKD2 | 11 | 50 ± 22 | 4/7 | 1.1 ± 0.2 | 3.6 ± 0.5 | 26 ± 2 | 56 ± 22 | 70 ± 27 | 21 ± 13 | DM (2), HTN (4), GN (4), RK (3) |
| CKD3 | 10 | 57 ± 17 | 5/5 | 1.7 ± 0.4# | 3.2 ± 0.8 | 25 ± 3 | 86 ± 51 | 79 ± 18# | 25 ± 8 | DM (3), HTN (7), GN (3), IN (1) |
| CKD4 | 14 | 62 ± 13 | 8/6 | 2.7 ± 0.6# | 3.5 ± 0.9 | 24 ± 3 | 202 ± 101# | 204 ± 173# | 21 ± 8 | DM (4), HTN (10), GN (3), RK (1) |
| CKD5 | 11 | 62 ± 12 | 5/6 | 4.7 ± 2.0# | 5.1 ± 3.5# | 21 ± 3 | 223 ± 188# | 580 ± 427# | 21 ± 9# | DM (7), HTN (7), GN (2) |
| Dialysis | 14 | 50 ± 12 | 6/8 | 11.9 ± 15.6# | 4.8 ± 1.7# | 22 ± 5 | 500 ± 650# | 760 ± 286# | 26 ± 8 | DM (7), HTN (10), GN (5), PKD (1) | n = number of subjects;
PCr = plasma creatinien;
GFR = estimated glomerular filtration rate;
Serum Pi = serum phosphorus;
Serum HCO3⁻ = serum bicarbonate
PTH = parathyroid hormone;
FGF23+ Fibroblast growth factor 23;
DM = Diabetes mellitus;
HTN = hypertension;
GN = glomerulonephrititis;
RK = Remnant kidney;
IN = Interstitial nephritis;
PKO = Polycystic kidney disease.
*Some patients carry more than one diagnosis.
Results are shown as mean ± standard deviation
p < 0.05 compared to healthy volunteers. ANOVA

TABLE 2

CDR sequence variations

| | L3 | | | | | | ID | H1 | | | | | ID | H2 | | | | | | | | ID |
|---|---|---|---|---|---|---|---|---|---|---|---|---|---|---|---|---|---|---|---|---|---|---|
| sb106 | QQA | G | Y | S | P | IT | 5 | GFNI | S | Y | Y | S | 6 | I | S | P | S | Y | G | Y | T | 7 |
| E12 | A | G | Y | A | P | I | 15 | I | A | Y | Y | A | V | 16 | F | I | A | P | S | Y | G | Y | S | S | 17 |
| E2 | A | G | F | A | P | I | 19 | I | S | Y | F | S | V | 20 | F | I | S | P | A | Y | G | F | T | A | 21 |
| C12 | A | A | F | A | P | V | 23 | I | A | F | Y | A | V | 24 | F | V | S | A | S | Y | G | Y | T | S | 25 |
| E3 | S | A | F | S | P | V | 27 | V | S | F | Y | S | I | 28 | Y | V | A | P | A | Y | G | Y | S | A | 29 |
| D7 | A | A | F | S | P | V | 31 | V | S | F | F | S | I | 32 | Y | I | S | P | S | Y | G | Y | S | S | 33 |
| E4 | A | G | F | A | P | I | 35 | I | S | Y | Y | A | V | 36 | F | V | S | P | A | Y | G | F | S | S | 37 |
| E6 | A | A | F | A | P | V | 39 | F | S | S | S | S | I | 40 | F | V | S | P | A | Y | G | F | T | A | 41 |
| E10 | A | G | Y | A | P | V | 43 | I | S | Y | Y | S | I | 44 | Y | I | S | P | S | F | G | Y | T | A | 45 |
| C9 | A | A | F | A | P | V | 47 | I | S | Y | Y | S | I | 48 | F | I | A | P | F | G | Y | S | S | 49 |
| D11 | A | A | F | S | P | I | 51 | I | A | Y | F | S | I | 52 | Y | V | S | P | A | Y | G | Y | T | S | 53 |
| E1 | A | G | Y | A | P | I | 55 | I | A | F | Y | S | I | 56 | Y | V | S | P | A | Y | A | Y | T | A | 57 |

TABLE 2-continued

CDR sequence variations

| | | | | | | | | | | | | | | | | | | | | | | |
|---|---|---|---|---|---|---|---|---|---|---|---|---|---|---|---|---|---|---|---|---|---|---|
| D5 | A | G | F | A | P | I | 59 | V | S | F | Y | S | I | 60 | S | I | S | S | S | Y | G | Y | T | Y | 61 |
| D12 | A | G | F | A | P | V | 63 | V | S | F | F | S | I | 64 | S | I | S | S | S | Y | G | Y | T | Y | 65 |
| E8 | S | A | Y | A | P | V | 67 | V | A | F | Y | S | I | 68 | F | I | A | P | S | Y | G | Y | S | A | 69 |
| E11 | A | G | F | A | P | V | 71 | I | A | F | F | S | I | 72 | F | V | S | P | A | Y | G | Y | T | A | 73 |
| F1 | S | A | Y | S | P | V | 75 | I | A | F | Y | S | I | 76 | F | V | S | P | A | Y | A | Y | S | A | 77 |
| D1 | A | A | F | A | P | V | 79 | F | S | S | S | S | I | 80 | Y | I | S | P | A | Y | G | Y | S | A | 81 |
| C10 | | | | | | | | V | S | Y | Y | S | I | 83 | S | I | S | S | S | Y | G | Y | T | S | 84 |
| D6 | S | A | F | S | P | V | 86 | I | A | F | F | A | V | 87 | F | V | S | P | S | F | G | Y | S | S | 88 |
| D8 | A | A | F | A | P | V | 90 | V | A | F | Y | S | I | 91 | Y | I | S | P | A | Y | A | Y | S | A | 92 |
| C11 | | | | | | | | I | S | Y | F | S | V | 94 | Y | V | S | P | S | F | A | F | S | S | 95 |
| F2 | A | A | Y | A | P | V | 97 | V | A | F | Y | S | V | 98 | S | I | S | S | S | Y | G | Y | T | A | 99 |
| D9 | A | A | Y | A | P | V | 101 | I | A | Y | Y | A | V | 102 | F | V | S | P | A | Y | G | F | T | S | 103 |
| E5 | A | A | F | A | P | V | 105 | I | A | F | Y | A | V | 106 | Y | V | A | P | P | Y | A | Y | S | A | 107 |
| D10 | A | A | Y | A | P | V | 109 | V | S | F | Y | S | I | 110 | Y | I | S | P | A | Y | G | Y | T | S | 111 |
| D3 | S | A | Y | S | P | V | 113 | V | A | Y | Y | S | I | 114 | Y | I | S | P | A | F | G | Y | S | S | 115 |
| D4 | A | A | Y | A | P | I | 117 | V | A | F | Y | A | V | 118 | S | I | S | S | S | Y | G | Y | T | Y | 119 |
| | QQA | G | Y | S | P | IT | 5 | GFNI | S | Y | Y | S | | 6 | | I | S | P | S | Y | G | Y | T | | 7 |

| | H3 | | | | | | | | | | | | | | ID |
|---|---|---|---|---|---|---|---|---|---|---|---|---|---|---|---|
| | sb106 | ARY | Y | V | Y | A | S | H | G | W | A | G | Y | G | MDY | 8 |
| | E12 | F | Y | V | Y | A | S | N | A | W | A | G | Y | G | M | 18 |
| | E2 | F | Y | V | Y | A | A | N | G | W | A | G | Y | G | M | 22 |
| | C12 | F | Y | V | Y | A | A | N | G | W | A | G | Y | G | M | 26 |
| | E3 | F | Y | V | Y | A | A | H | G | W | A | G | Y | G | M | 30 |
| | D7 | F | Y | V | Y | A | A | N | G | W | A | G | Y | G | M | 34 |
| | E4 | F | F | V | Y | A | A | H | G | W | A | G | Y | G | M | 38 |
| | E6 | F | F | V | Y | S | S | H | G | W | A | G | Y | G | M | 42 |
| | E10 | F | Y | V | Y | S | S | H | G | W | A | G | Y | G | M | 46 |
| | C9 | F | Y | V | Y | A | A | N | G | W | A | G | Y | G | M | 50 |
| | D11 | F | Y | V | Y | S | A | N | G | W | A | G | Y | G | M | 54 |
| | E1 | F | Y | V | Y | A | A | H | G | W | A | G | Y | G | M | 58 |
| | D5 | F | Y | V | Y | A | S | N | G | W | A | G | Y | G | M | 62 |
| | D12 | F | Y | V | Y | S | S | H | G | W | A | G | Y | G | M | 66 |
| | E8 | F | F | V | Y | A | A | H | G | W | A | G | Y | G | M | 70 |
| | E11 | F | Y | V | Y | S | A | N | G | W | A | G | Y | G | M | 74 |
| | F1 | F | Y | V | Y | S | A | N | G | W | A | G | Y | G | M | 78 |
| | D1 | F | F | V | Y | S | A | N | A | W | S | G | Y | G | M | 82 |
| | C10 | F | F | V | Y | A | A | H | G | W | A | G | Y | G | M | 85 |
| | D6 | F | Y | V | Y | A | A | H | G | W | A | G | Y | G | M | 89 |
| | D8 | Y | F | V | Y | A | A | N | G | W | A | G | Y | G | M | 93 |
| | C11 | F | F | V | Y | S | A | H | G | W | A | G | Y | G | M | 96 |
| | F2 | F | Y | V | Y | A | A | H | G | W | A | G | Y | G | M | 100 |
| | D9 | F | Y | V | Y | S | S | H | G | W | A | G | F | G | M | 104 |
| | E5 | F | Y | V | Y | S | A | H | G | W | A | G | Y | G | M | 108 |
| | D10 | F | Y | V | Y | S | A | H | G | W | A | G | Y | G | M | 112 |
| | D3 | F | Y | V | Y | A | A | N | G | W | A | G | Y | G | M | 116 |
| | D4 | Y | Y | V | Y | A | A | H | G | W | A | G | Y | G | M | 120 |
| | | ARY | Y | V | Y | A | S | H | G | W | A | G | Y | G | MDY | 8 |

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1. Kuro-o M, Matsumura Y, Aizawa H, et al. (1997) Mutation of the mouse klotho gene leads to a syndrome resembling ageing. *Nature* 390: 45-51.
2. Nabeshima Y. (2002) Klotho: a fundamental regulator of aging. *Ageing Res Rev* 1: 627-638.
3. Matsumura Y, Aizawa H, Shiraki-lida T, Nagai R, Kuro-o M, Nabeshima Y. (1998) Identification of the human klotho gene and its two transcripts encoding membrane and secreted klotho protein. *Biochem Biophys Res Commun* 242: 626-630.
4. Ben-Dov I Z, Galitzer H, Lavi-Moshayoff V, Goetz R, Kuro-o M, Mohammadi M, Sirkis R, Naveh-Many T, Silver J. (2007) The parathyroid is a target organ for FGF23 in rats. *J Clin Invest* 117: 4003-4008.
5. Ito S, Kinoshita S, Shiraishi N, Nakagawa S, Sekine S, Fujimori T, Nabeshima Yl. (2000) Molecular cloning and expression analyses of mouse betaklotho, which encodes a novel Klotho family protein. *Mech Dev* 98: 115-119.
6. Kuro-o M. (2012) Klotho and betaKlotho. *Adv Exp Med Biol* 728: 25-40.
7. Hu M C, Shi M, Zhang J, et al. Klotho: a novel phosphaturic substance acting as an autocrine enzyme in the renal proximal tubule. FASEB J 2010; 24(9):3438-3450
8. Kato Y, Arakawa E, Kinoshita S, et al. Establishment of the anti-Klotho monoclonal antibodies and detection of Klotho protein in kidneys. Biochem Biophys Res Commun 2000; 267(2):597-602
9. Goetz R, Nakada Y, Hu M C, et al. Isolated C-terminal tail of FGF23 alleviates hypophosphatemia by inhibiting FGF23-FGFR-Klotho complex formation. Proc Natl Acad Sci USA 2010; 107(1):407-412
10. Kurosu H, Ogawa Y, Miyoshi M, et al. Regulation of fibroblast growth factor-23 signaling by klotho. J Biol Chem 2006; 281(10):6120-6123
11. Urakawa I, Yamazaki Y, Shimada T, et al. Klotho converts canonical FGF receptor into a specific receptor for FGF23. Nature 2006; 444(7120):770-774
12. Hu M C, Shi M, Zhang J, et al. Klotho deficiency causes vascular calcification in chronic kidney disease. J Am Soc Nephrol 2011; 22(1):124-136
13. Imura A, Iwano A, Tohyama O, et al. Secreted Klotho protein in sera and CSF: implication for post-translational cleavage in release of Klotho protein from cell membrane. FEBS Lett 2004; 565(1-3):143-147
14. Bloch L, Sineshchekova O, Reichenbach D, et al. Klotho is a substrate for alpha-, beta- and gamma-secretase. FEBS Lett 2009; 583(19):3221-3224
15. Chen C D, Podvin S, Gillespie E, et al. Insulin stimulates the cleavage and release of the extracellular domain of Klotho by ADAM10 and ADAM17. Proc Natl Acad Sci USA 2007; 104(50):19796-19801
16. Hu M C, Shi M, Zhang J, et al. Renal production and metabolism of circulating Klotho. Submitted
17. Hu M C, Kuro-o M, Moe O W. Secreted klotho and chronic kidney disease. Adv Exp Med Biol 2012; 728: 126-157
18. Aizawa H, Saito Y, Nakamura T, et al. Downregulation of the Klotho gene in the kidney under sustained circulatory stress in rats. Biochem Biophys Res Commun 1998; 249(3):865-871
19. Cheng M F, Chen L J, Cheng J T. Decrease of Klotho in the kidney of streptozotocin-induced diabetic rats. J Biomed Biotechnol 2010; 2010:513853
20. Haruna Y, Kashihara N, Satoh M, et al. Amelioration of progressive renal injury by genetic manipulation of Klotho gene. Proc Natl Acad Sci USA 2007; 104(7):2331-2336
21. Koh N, Fujimori T, Nishiguchi S, et al. Severely reduced production of klotho in human chronic renal failure kidney. Biochem Biophys Res Commun 2001; 280(4): 1015-1020
22. Mitani H, Ishizaka N, Aizawa T, et al. In vivo klotho gene transfer ameliorates angiotensin II-induced renal damage. Hypertension 2002; 39(4):838-843
23. Wang Y, Sun Z. Klotho gene delivery prevents the progression of spontaneous hypertension and renal damage. Hypertension 2009; 54:810-817
24. Zhao Y, Banerjee S, Dey N, et al. Klotho depletion contributes to increased inflammation in kidney of the db/db mouse model of diabetes via RelA (serine)536 phosphorylation. Diabetes 2011; 60(7):1907-1916
25. Hu M C, Shi M, Zhang J, et al. Klotho deficiency is an early biomarker of renal ischemia-reperfusion injury and its replacement is protective. Kidney Int 2010; 78(12): 1240-1251
26. Hu M C, Moe O W. Klotho as a potential biomarker and therapy for acute kidney injury. Nat Rev Nephrol 2012; 8(7):423-429
27. Goetz R, Beenken A, Ibrahimi O A, et al. (2007) Molecular insights into the klotho-dependent, endocrine mode of action of fibroblast growth factor 19 subfamily members. *Mol Cell Biol* 27: 3417-3428.
28. Shimada T, Kakitani M, Yamazaki Y, Hasegawa H, Takeuchi Y, Fujita T, Fukumoto S, Tomizuka K, Yamashita T. (2004) Targeted ablation of Fgf23 demonstrates an essential physiological role of FGF23 in phosphate and vitamin D metabolism. *J Clin Invest* 113: 561-568.
29. Ichikawa S, Imel E A, Kreiter M L, et al. (2007) A homozygous missense mutation in human KLOTHO causes severe tumoral calcinosis. *J Clin Invest* 117: 2684-2691.
30. Kuro-o M. (2010) Overview of the FGF23-Klotho axis. *Pediatr Nephrol* 25: 583-590.
31. Kurosu H, Kuro O M. (2009) The Klotho gene family as a regulator of endocrine fibroblast growth factors. *Mol Cell Endocrinol* 299: 72-78.
32. Ayodele O E, Alebiosu C O. (2010) Burden of chronic kidney disease: an international perspective. *Adv Chronic Kidney Dis* 17: 215-224.
33. Soni R K, Weisbord S D, Unruh M L. (2010) Health-related quality of life outcomes in chronic kidney disease. *Curr Opin Nephrol Hypertens* 19: 153-159.
34. Trivedi H. (2010) Cost implications of caring for chronic kidney disease: are interventions cost-effective? *Adv Chronic Kidney Dis* 17: 265-270.
35. Ganesh S K, Stack A G, Levin N W, Hulbert-Shearon T, Port F K. (2001) Association of elevated serum PO(4), Ca×PO(4) product, and parathyroid hormone with cardiac mortality risk in chronic hemodialysis patients. *J Am Soc Nephrol* 12: 2131-2138.
36. Tonelli M, Curhan G, Pfeffer M, Sacks F, Thadhani R, Melamed M L, Wiebe N, Muntner P. (2009) Relation between alkaline phosphatase, serum phosphate, and all-cause or cardiovascular mortality. *Circulation* 120: 1784-1792.
37. Gutierrez O, Isakova T, Rhee E, Shah A, Holmes J, Collerone G, Juppner H, Wolf M. (2005) Fibroblast growth factor-23 mitigates hyperphosphatemia but accentuates calcitriol deficiency in chronic kidney disease. *J Am Soc Nephrol* 16: 2205-2215.
38. Asai O, Nakatani K, Tanaka T, et al. Decreased renal alpha-Klotho expression in early diabetic nephropathy in humans and mice and its possible role in urinary calcium excretion. Kidney Int 2012; 81 (6):539-547
39. Akimoto T, Kimura T, Watanabe Y, et al. The impact of nephrectomy and renal transplantation on serum levels of soluble Klotho protein. Transplant Proc 2013; 45(1):134-136
40. Akimoto T, Shiizaki K, Sugase T, et al. The relationship between the soluble Klotho protein and the residual renal function among peritoneal dialysis patients. Clin Exp Nephrol 2012; 16(3):442-447
41. Akimoto T, Yoshizawa H, Watanabe Y, et al. Characteristics of urinary and serum soluble Klotho protein in patients with different degrees of chronic kidney disease. BMC Nephrol 2012; 13:155

42. Carpenter T O, Insogna K L, Zhang J H, et al. Circulating Levels of Soluble Klotho and FGF23 in X-Linked Hypophosphatemia: Circadian Variance, Effects of Treatment, and Relationship to Parathyroid Status. J Clin Endocrinol Metab 2010; 95(11):E352-357
43. Crasto C L, Semba R D, Sun K, et al. Relationship of low-circulating "anti-aging" klotho hormone with disability in activities of daily living among older community-dwelling adults. Rejuvenation Res 2012; 15(3):295-301
44. Devaraj S, Syed B, Chien A, et al. Validation of an immunoassay for soluble klotho protein: decreased levels in diabetes and increased levels in chronic kidney disease. Am J Clin Pathol 2012; 137(3):479-485
45. Fliser D, Seiler S, Heine G H, et al. Measurement of serum soluble Klotho levels in CKD 5D patients: useful tool or dispensable biomarker? Nephrol Dial Transplant 2012; 27(5):1702-1703
46. Heijboer A C, Blankenstein M A, Hoenderop J, et al. Laboratory aspects of circulating alpha-Klotho. Nephrol Dial Transplant 2013; 28(9):2283-2287
47. Kacso I M, Bondor C I, Kacso G. Soluble serum Klotho in diabetic nephropathy: relationship to VEGF-A. Clin Biochem 2012; 45(16-17):1415-1420
48. Kim H R, Nam B Y, Kim D W, et al. Circulating alpha-Klotho levels in CKD and relationship to progression. Am J Kidney Dis 2013; 61(6):899-909
49. Kitagawa M, Sugiyama H, Morinaga H, et al. A decreased level of serum soluble Klotho is an independent biomarker associated with arterial stiffness in patients with chronic kidney disease. PLoS One 2013; 8(2): e56695
50. Komaba H, Koizumi M, Tanaka H, et al. Effects of cinacalcet treatment on serum soluble Klotho levels in haemodialysis patients with secondary hyperparathyroidism. Nephrol Dial Transplant 2012; 27(5):1967-1969
51. Pavik I, Jaeger P, Ebner L, et al. Soluble klotho and autosomal dominant polycystic kidney disease. Clin J Am Soc Nephrol 2012; 7(2):248-257
52. Pavik I, Jaeger P, Ebner L, et al. Secreted Klotho and FGF23 in chronic kidney disease Stage 1 to 5: a sequence suggested from a cross-sectional study. Nephrol Dial Transplant 2013; 28(2):352-359
53. Seiler S, Wen M, Roth H J, et al. Plasma Klotho is not related to kidney function and does not predict adverse outcome in patients with chronic kidney disease. Kidney Int 2013; 83(1):121-128
54. Shimamura Y, Hamada K, Inoue K, et al. Serum levels of soluble secreted alpha-Klotho are decreased in the early stages of chronic kidney disease, making it a probable novel biomarker for early diagnosis. Clin Exp Nephrol 2012; 16(5):722-729
55. Siahanidou T, Garatzioti M, Lazaropoulou C, et al. Plasma soluble alpha-Klotho protein levels in premature and term neonates: correlations with growth and metabolic parameters. Eur J Endocrinol 2012; 167(3):433-440
56. Sugiura H, Tsuchiya K, Nitta K. Circulating levels of soluble alpha-Klotho in patients with chronic kidney disease. Clin Exp Nephrol 2011; 15(5):795-796
57. Wan M, Smith C, Shah V, et al. Fibroblast growth factor 23 and soluble klotho in children with chronic kidney disease. Nephrol Dial Transplant 2013; 28(1):153-161
58. Yamazaki Y, Imura A, Urakawa I, et al. Establishment of sandwich ELISA for soluble alpha-Klotho measurement: Age-dependent change of soluble alpha-Klotho levels in healthy subjects. Biochem Biophys Res Commun 2010; 398(3):513-518
59. Yokoyama K, Imura A, Ohkido I, et al. Serum soluble alpha-Klotho in hemodialysis patients. Clin Nephrol 2012; 77(5):347-351
60. Semba R D, Cappola A R, Sun K, et al. Plasma klotho and mortality risk in older community-dwelling adults. J Gerontol A Biol Sci Med Sci 2011; 66(7):794-800
61. Doi S, Zou Y, Togao O, et al. Klotho inhibits transforming growth factor-beta1 (TGF-beta1) signaling and suppresses renal fibrosis and cancer metastasis in mice. J Biol Chem 2011; 286(10):8655-8665
62. Ohyama Y, Kurabayashi M, Masuda H, et al. Molecular cloning of rat klotho cDNA: markedly decreased expression of klotho by acute inflammatory stress. Biochemical And Biophysical Research Communications 1998; 251 (3):920-925
63. Sugiura H, Yoshida T, Mitobe M, et al. Klotho reduces apoptosis in experimental ischaemic acute kidney injury via HSP-70. Nephrol Dial Transplant 2010; 25(1):60-68
64. Sugiura H, Yoshida T, Tsuchiya K, et al. Klotho reduces apoptosis in experimental ischaemic acute renal failure. Nephrol Dial Transplant 2005; 20(12):2636-2645
65. Moreno J A, Izquierdo M C, Sanchez-Nino M D, et al. The inflammatory cytokines TWEAK and TNFalpha reduce renal klotho expression through NFkappaB. J Am Soc Nephrol 2011; 22(7):1315-1325
66. Goldstein S L. Acute kidney injury biomarkers: renal angina and the need for a renal troponin I. BMC Med 2011; 9:135
67. Fellouse F A, Esaki K, Birtalan S, et al. High-throughput generation of synthetic antibodies from highly functional minimalist phage-displayed libraries. J Mol Biol 2007; 373(4):924-940
68. Gao J, Sidhu S S, Wells J A. Two-state selection of conformation-specific antibodies. Proc Natl Acad Sci USA 2009; 106(9):3071-3076
69. Koellhoffer J F, Chen G, Sandesara R G, et al. Two synthetic antibodies that recognize and neutralize distinct proteolytic forms of the ebola virus envelope glycoprotein. Chembiochem 2012; 13(17):2549-2557
70. Li B, Russell S J, Compaan D M, et al. Activation of the proapoptotic death receptor DR5 by oligomeric peptide and antibody agonists. J Mol Biol 2006; 361(3):522-536
71. Uysal S, Vasquez V, Tereshko V, et al. Crystal structure of full-length KcsA in its closed conformation. Proc Natl Acad Sci USA 2009; 106(16):6644-6649
72. Ibrahimi O A, Zhang F, Eliseenkova A V, et al. Biochemical analysis of pathogenic ligand-dependent FGFR2 mutations suggests distinct pathophysiological mechanisms for craniofacial and limb abnormalities. Hum Mol Genet 2004; 13(19):2313-2324
73. Plotnikov A N, Hubbard S R, Schlessinger J, et al. Crystal structures of two FGF-FGFR complexes reveal the determinants of ligand-receptor specificity. Cell 2000; 101(4):413-424
74. Persson H, Ye W, Wernimont A, et al. CDR-H3 diversity is not required for antigen recognition by synthetic antibodies. J Mol Biol 2013; 425(4):803-811
75. Rajan S, Sidhu S S. Simplified synthetic antibody libraries. Methods Enzymol 2012; 502:3-23
76. Colwill K, Graslund S. A roadmap to generate renewable protein binders to the human proteome. Nat Methods 2011; 8(7):551-558
77. Olsen S K, Garbi M, Zampieri N, et al. Fibroblast growth factor (FGF) homologous factors share structural but not functional homology with FGFs. J Biol Chem 2003; 278(36):34226-34236

78. Kurosu H, Choi M, Ogawa Y, et al. Tissue-specific expression of betaKlotho and fibroblast growth factor (FGF) receptor isoforms determines metabolic activity of FGF19 and FGF21. J Biol Chem 2007; 282(37):26687-26695
79. Kurosu H, Yamamoto M, Clark J D, et al. Suppression of aging in mice by the hormone Klotho. Science 2005; 309(5742):1829-1833
80. Kuro-o M, Matsumura Y, Aizawa H, et al. Mutation of the mouse klotho gene leads to a syndrome resembling ageing. Nature 1997; 390(6655):45-51
81. Hu M C, Shiizaki K, Kuro-o M, et al. Physiology and pathophysiology of an endocrine network of mineral metabolism. Ann Rev Phys 2013; 75:503-533
82. Hu M C, Kuro-o M, Moe O W. Renal and extrarenal actions of Klotho. Semin Nephrol 2013; 33(2):118-129
83. Pedersen L, Pedersen S M, Brasen C L, et al. Soluble serum Klotho levels in healthy subjects. Comparison of two different immunoassays. Clin Biochem 2013; 46(12):1079-1083
84. Grams M E, Chow E K, Segev D L, Coresh J. Lifetime incidence of CKD stages 3-5 in the United States. Am J Kidney Dis. 2013 August; 62(2):245-52.
85. Lefranc et al. IMGT unique numbering for immunoglobulin and T cell receptor variable domains and Ig superfamily V-like domains. Development and Comparative Immunology. 2003; 27:55-77

The invention claimed is:

1. A nucleic acid encoding an antibody and/or antigen binding fragment thereof, wherein said antibody and/or antigen binding fragment thereof comprises a light chain variable region and a heavy chain variable region, the light chain variable region comprising complementarity determining regions CDR-L1, CDR-L2 and CDR-L3 and the heavy chain variable region comprising complementarity determining regions CDR-H1, CDR-H2 and CDR-H3, with the amino acid sequences of said CDRs set forth below:

CDR-L1: SEQ ID NO: 9;
CDR-L2: SEQ ID NO: 10;
CDR-L3: SEQ ID NO: 5;
CDR-H1: SEQ ID NO: 6;
CDR-H2: SEQ ID NO: 7; and
CDR-H3: SEQ ID NO: 8.

2. The nucleic acid of claim 1, wherein the light chain variable region of the antibody and/or antigen binding fragment thereof comprises the amino acid sequence set forth in SEQ ID NO: 11.

3. The nucleic acid of claim 1, wherein the heavy chain variable region of the antibody and/or antigen binding fragment thereof comprises the amino acid sequence set forth in SEQ ID NO: 12.

4. The nucleic acid of claim 1, wherein the antibody and/or antigen binding fragment thereof comprises heavy chain IgG1 or IgG4 isotypes, with the amino acid sequence of said isotypes set forth in SEQ ID NO: 13 or SEQ ID NO:14.

5. The nucleic acid of claim 1, wherein the antibody and/or antigen binding fragment thereof specifically binds to an epitope of an αKlotho polypeptide, said αKlotho polypeptide being soluble αKlotho polypeptide.

6. The nucleic acid of claim 1, wherein the antibody and/or antigen binding fragment thereof specifically binds to an epitope of an αKlotho polypeptide, said αKlotho polypeptide being mammalian αKlotho polypeptide, optionally human αKlotho polypeptide or rodent αKlotho polypeptide.

7. The nucleic acid of claim 1, wherein the antibody and/or antigen binding fragment thereof binds soluble αKlotho polypeptide found in urine, plasma, and/or serum.

8. The nucleic acid of claim 1, wherein the antibody and/or antigen binding fragment thereof binds a complex comprising folded αKlotho polypeptide.

9. A vector comprising the nucleic acid of claim 1.

10. A recombinant cell comprising the nucleic acid of claim 1 or a vector comprising said nucleic acid.

11. A composition comprising the nucleic acid of claim 1 or a vector comprising said nucleic acid.

12. A composition comprising the recombinant cell of claim 10.

13. A method for producing an antibody and/or antigen binding fragment thereof with specific binding affinity to an epitope of an αKlotho polypeptide, the steps comprising:
  a. expressing in a host cell the nucleic acid according to claim 1;
  b. culturing the host cell to produce the antibody and/or antigen binding fragment thereof; and
  c. isolating and purifying the antibody and/or antigen binding fragment thereof from the host cell.

14. A kit comprising the nucleic acid according to claim 1 or a vector comprising said nucleic acid, a reference agent and optionally instructions for use thereof.

* * * * *

UNITED STATES PATENT AND TRADEMARK OFFICE
CERTIFICATE OF CORRECTION

PATENT NO. : 10,697,963 B2
APPLICATION NO. : 16/261141
DATED : June 30, 2020
INVENTOR(S) : Sachdev S. Sidhu et al.

Page 1 of 1

It is certified that error appears in the above-identified patent and that said Letters Patent is hereby corrected as shown below:

In the Specification

Column 1, Lines 16–19, delete "This invention was made in part with U.S. Government support under NIH Grant Nos. R01DK091392, R01DK092461 and R01DE13686. The U.S. Government may have certain rights in this invention." and insert --This invention was made with government support under grant numbers DK079328 and DK091392 awarded by The National Institutes of Health. The government has certain rights in the invention.--

Signed and Sealed this
Twenty-eighth Day of July, 2020

Andrei Iancu
*Director of the United States Patent and Trademark Office*

SEQUENCE LISTING

```
<160> NUMBER OF SEQ ID NOS: 120

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is A or S
<220> FEATURE:
<221> NAME/KEY: MISC_FEATURE
<222> LOCATION: (2)..(2)
<223> OTHER INFORMATION: Xaa is G or A
<220> FEATURE:
<221> NAME/KEY: MISC_FEATURE
<222> LOCATION: (3)..(3)
<223> OTHER INFORMATION: Xaa is Y or F
<220> FEATURE:
<221> NAME/KEY: MISC_FEATURE
<222> LOCATION: (4)..(4)
<223> OTHER INFORMATION: Xaa is S or A
<220> FEATURE:
<221> NAME/KEY: MISC_FEATURE
<222> LOCATION: (6)..(6)
<223> OTHER INFORMATION: Xaa is I or V

<400> SEQUENCE: 1

Xaa Xaa Xaa Xaa Pro Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is I or V
<220> FEATURE:
<221> NAME/KEY: MISC_FEATURE
<222> LOCATION: (2)..(2)
<223> OTHER INFORMATION: Xaa is S or A
<220> FEATURE:
<221> NAME/KEY: MISC_FEATURE
<222> LOCATION: (3)..(3)
<223> OTHER INFORMATION: Xaa is Y, F or S
<220> FEATURE:
<221> NAME/KEY: MISC_FEATURE
<222> LOCATION: (4)..(4)
<223> OTHER INFORMATION: Xaa is Y, F or S
<220> FEATURE:
<221> NAME/KEY: MISC_FEATURE
<222> LOCATION: (5)..(5)
```

```
<223> OTHER INFORMATION: Xaa is S or A
<220> FEATURE:
<221> NAME/KEY: MISC_FEATURE
<222> LOCATION: (6)..(6)
<223> OTHER INFORMATION: Xaa is I or V

<400> SEQUENCE: 2

Xaa Xaa Xaa Xaa Xaa Xaa
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Y, F or S
<220> FEATURE:
<221> NAME/KEY: MISC_FEATURE
<222> LOCATION: (2)..(2)
<223> OTHER INFORMATION: Xaa is I or V
<220> FEATURE:
<221> NAME/KEY: MISC_FEATURE
<222> LOCATION: (3)..(3)
<223> OTHER INFORMATION: Xaa is S or A
<220> FEATURE:
<221> NAME/KEY: MISC_FEATURE
<222> LOCATION: (4)..(4)
<223> OTHER INFORMATION: Xaa is P or S
<220> FEATURE:
<221> NAME/KEY: MISC_FEATURE
<222> LOCATION: (5)..(5)
<223> OTHER INFORMATION: Xaa is S or A
<220> FEATURE:
<221> NAME/KEY: MISC_FEATURE
<222> LOCATION: (6)..(6)
<223> OTHER INFORMATION: Xaa is Y or F
<220> FEATURE:
<221> NAME/KEY: MISC_FEATURE
<222> LOCATION: (7)..(7)
<223> OTHER INFORMATION: Xaa is G or A
<220> FEATURE:
<221> NAME/KEY: MISC_FEATURE
<222> LOCATION: (8)..(8)
<223> OTHER INFORMATION: Xaa is Y or F
<220> FEATURE:
<221> NAME/KEY: MISC_FEATURE
<222> LOCATION: (9)..(9)
<223> OTHER INFORMATION: Xaa is T or S
<220> FEATURE:
<221> NAME/KEY: MISC_FEATURE
<222> LOCATION: (10)..(10)
<223> OTHER INFORMATION: Xaa is S, A or Y

<400> SEQUENCE: 3

Xaa Xaa Xaa Xaa Xaa Xaa Xaa Xaa Xaa Xaa
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Y or F
<220> FEATURE:
<221> NAME/KEY: MISC_FEATURE
<222> LOCATION: (2)..(2)
<223> OTHER INFORMATION: Xaa is Y or F
```

```
<220> FEATURE:
<221> NAME/KEY: MISC_FEATURE
<222> LOCATION: (5)..(5)
<223> OTHER INFORMATION: Xaa is A or S
<220> FEATURE:
<221> NAME/KEY: MISC_FEATURE
<222> LOCATION: (6)..(6)
<223> OTHER INFORMATION: Xaa is S or A
<220> FEATURE:
<221> NAME/KEY: MISC_FEATURE
<222> LOCATION: (7)..(7)
<223> OTHER INFORMATION: Xaa is H or N
<220> FEATURE:
<221> NAME/KEY: MISC_FEATURE
<222> LOCATION: (8)..(8)
<223> OTHER INFORMATION: Xaa is G or A
<220> FEATURE:
<221> NAME/KEY: MISC_FEATURE
<222> LOCATION: (10)..(10)
<223> OTHER INFORMATION: Xaa is A or S
<220> FEATURE:
<221> NAME/KEY: MISC_FEATURE
<222> LOCATION: (12)..(12)
<223> OTHER INFORMATION: Xaa is Y or F

<400> SEQUENCE: 4

Xaa Xaa Val Tyr Xaa Xaa Xaa Xaa Trp Xaa Gly Xaa Gly Met
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Gln Gln Ala Gly Tyr Ser Pro Ile Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Gly Phe Asn Ile Ser Tyr Tyr Ser
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Ile Ser Pro Ser Tyr Gly Tyr Thr
1               5

<210> SEQ ID NO 8
<211> LENGTH: 18
<212> TYPE: PRT
<213> ORGANISM: Artificial Sequence
<220> FEATURE:
<223> OTHER INFORMATION: Synthetic Construct

<400> SEQUENCE: 8
```

```
Ala Arg Tyr Tyr Val Tyr Ala Ser His Gly Trp Ala Gly Tyr Gly Met
1               5                   10                  15

Asp Tyr
```

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

```
Gln Ser Val Ser Ser Ala
1               5
```

<210> SEQ ID NO 10
<211> LENGTH: 3
<212> TYPE: PRT
<213> ORGANISM: Artificial Sequence
<220> FEATURE:
<223> OTHER INFORMATION: Synthetic Construct

<400> SEQUENCE: 10

```
Ser Ala Ser
1
```

<210> SEQ ID NO 11
<211> LENGTH: 214
<212> TYPE: PRT
<213> ORGANISM: Artificial Sequence
<220> FEATURE:
<223> OTHER INFORMATION: Synthetic Construct

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gly Tyr Ser Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 12
<211> LENGTH: 233
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Ser Ile His Trp Val Arg Gln Ala Pro Gly Lys Gly Leu Glu Trp Val
        35                  40                  45

Ala Tyr Ile Ser Pro Ser Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Val Tyr Ala Ser His Gly Trp Ala Gly Tyr Gly Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230

<210> SEQ ID NO 13
<211> LENGTH: 455
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Ser Ile His Trp Val Arg Gln Ala Pro Gly Lys Gly Leu Glu Trp Val
        35                  40                  45

Ala Tyr Ile Ser Pro Ser Tyr Gly Tyr Thr Ser Tyr Ala Asp Ser Val
```

```
                50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Val Tyr Ala Ser His Gly Trp Ala Gly Tyr Gly Met
                100                 105                 110

Asp Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Glu Glu Met Thr Lys
                355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
                450                 455

<210> SEQ ID NO 14
```

<211> LENGTH: 452
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Ser Ile His Trp Val Arg Gln Ala Pro Gly Lys Gly Leu Glu Trp Val
        35                  40                  45

Ala Tyr Ile Ser Pro Ser Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Val Tyr Ala Ser His Gly Trp Ala Gly Tyr Gly Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Ser Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
        420                 425                 430

Met His Glu Ala Leu His Asn His Tyr Thr Gln Lys Ser Leu Ser Leu
        435                 440                 445

Ser Pro Gly Lys
    450

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Ala Gly Tyr Ala Pro Ile
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Ile Ala Tyr Tyr Ala Val
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Phe Ile Ala Pro Ser Tyr Gly Tyr Ser Ser
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Phe Tyr Val Tyr Ala Ser Asn Ala Trp Ala Gly Tyr Gly Met
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

<400> SEQUENCE: 19

Ala Gly Phe Ala Pro Ile
```

```
1               5
```

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

```
Ile Ser Tyr Phe Ser Val
1               5
```

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

```
Phe Ile Ser Pro Ala Tyr Gly Phe Thr Ala
1               5                  10
```

<210> SEQ ID NO 22
<211> LENGTH: 14
<212> TYPE: PRT
<213> ORGANISM: Artificial Sequence
<220> FEATURE:
<223> OTHER INFORMATION: Synthetic Construct

<400> SEQUENCE: 22

```
Phe Tyr Val Tyr Ala Ala Asn Gly Trp Ala Gly Tyr Gly Met
1               5                  10
```

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

```
Ala Ala Phe Ala Pro Val
1               5
```

<210> SEQ ID NO 24
<211> LENGTH: 6
<212> TYPE: PRT
<213> ORGANISM: Artificial Sequence
<220> FEATURE:
<223> OTHER INFORMATION: Synthetic Construct

<400> SEQUENCE: 24

```
Ile Ala Phe Tyr Ala Val
1               5
```

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

```
Phe Val Ser Ala Ser Tyr Gly Tyr Thr Ser
1               5                  10
```

```
<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

Phe Tyr Val Tyr Ala Ala Asn Gly Trp Ala Gly Tyr Gly Met
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

Ser Ala Phe Ser Pro Val
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Val Ser Phe Tyr Ser Ile
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Tyr Val Ala Pro Ala Tyr Gly Tyr Ser Ala
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30

Phe Tyr Val Tyr Ala Ala His Gly Trp Ala Gly Tyr Gly Met
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Synthetic Construct

<400> SEQUENCE: 31

Ala Ala Phe Ser Pro Val
1               5
```

```
<210> SEQ ID NO 32
<211> LENGTH: 6
<212> TYPE: PRT
<213> ORGANISM: Artificial Sequence
<220> FEATURE:
<223> OTHER INFORMATION: Synthetic Construct

<400> SEQUENCE: 32

Val Ser Phe Phe Ser Ile
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Tyr Ile Ser Pro Ser Tyr Gly Tyr Ser Ser
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic Construct

<400> SEQUENCE: 34

Phe Tyr Val Tyr Ala Ala Asn Gly Trp Ala Gly Tyr Gly Met
1               5                   10

<210> SEQ ID NO 35
<211> LENGTH: 6
<212> TYPE: PRT
<213> ORGANISM: Artificial Sequence
<220> FEATURE:
<223> OTHER INFORMATION: Synthetic Construct

<400> SEQUENCE: 35

Ala Gly Phe Ala Pro Ile
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic Construct

<400> SEQUENCE: 36

Ile Ser Tyr Tyr Ala Val
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Phe Val Ser Pro Ala Tyr Gly Phe Ser Ser
1               5                   10
```

```
<210> SEQ ID NO 38
<211> LENGTH: 14
<212> TYPE: PRT
<213> ORGANISM: Artificial Sequence
<220> FEATURE:
<223> OTHER INFORMATION: Synthetic Construct

<400> SEQUENCE: 38

Phe Phe Val Tyr Ala Ala His Gly Trp Ala Gly Tyr Gly Met
1               5                   10

<210> SEQ ID NO 39
<211> LENGTH: 6
<212> TYPE: PRT
<213> ORGANISM: Artificial Sequence
<220> FEATURE:
<223> OTHER INFORMATION: Synthetic Construct

<400> SEQUENCE: 39

Ala Ala Phe Ala Pro Val
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Construct

<400> SEQUENCE: 40

Phe Ser Ser Ser Ser Ile
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Phe Val Ser Pro Ala Tyr Gly Phe Thr Ala
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic Construct

<400> SEQUENCE: 42

Phe Phe Val Tyr Ser Ser His Gly Trp Ala Gly Tyr Gly Met
1               5                   10

<210> SEQ ID NO 43
<211> LENGTH: 6
<212> TYPE: PRT
<213> ORGANISM: Artificial Sequence
<220> FEATURE:
<223> OTHER INFORMATION: Synthetic Construct

<400> SEQUENCE: 43

Ala Gly Tyr Ala Pro Val
1               5

<210> SEQ ID NO 44
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 44

Ile Ser Tyr Tyr Ser Ile
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Tyr Ile Ser Pro Ser Phe Gly Tyr Thr Ala
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Synthetic Construct

<400> SEQUENCE: 46

Phe Tyr Val Tyr Ser Ser His Gly Trp Ala Gly Tyr Gly Met
1               5                   10

<210> SEQ ID NO 47
<211> LENGTH: 6
<212> TYPE: PRT
<213> ORGANISM: Artificial Sequence
<220> FEATURE:
<223> OTHER INFORMATION: Synthetic Construct

<400> SEQUENCE: 47

Ala Ala Phe Ala Pro Val
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic Construct

<400> SEQUENCE: 48

Ile Ser Tyr Tyr Ser Ile
1               5

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Phe Ile Ala Pro Ala Phe Gly Tyr Ser Ser
1               5                   10

<210> SEQ ID NO 50
<211> LENGTH: 14
```

```
<212> TYPE: PRT
<213> ORGANISM: Artificial Sequence
<220> FEATURE:
<223> OTHER INFORMATION: Synthetic Construct

<400> SEQUENCE: 50

Phe Tyr Val Tyr Ala Ala Asn Gly Trp Ala Gly Tyr Gly Met
1               5                   10

<210> SEQ ID NO 51
<211> LENGTH: 6
<212> TYPE: PRT
<213> ORGANISM: Artificial Sequence
<220> FEATURE:
<223> OTHER INFORMATION: Synthetic Construct

<400> SEQUENCE: 51

Ala Ala Phe Ser Pro Ile
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Construct

<400> SEQUENCE: 52

Ile Ala Tyr Phe Ser Ile
1               5

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

Tyr Val Ser Pro Ala Tyr Gly Tyr Thr Ser
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic Construct

<400> SEQUENCE: 54

Phe Tyr Val Tyr Ser Ala Asn Gly Trp Ala Gly Tyr Gly Met
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct

<400> SEQUENCE: 55

Ala Gly Tyr Ala Pro Ile
1               5

<210> SEQ ID NO 56
<211> LENGTH: 6
<212> TYPE: PRT
```

<213> ORGANISM: Artificial Sequence
<220> FEATURE:
<223> OTHER INFORMATION: Synthetic Construct

<400> SEQUENCE: 56

Ile Ala Phe Tyr Ser Ile
1               5

<210> SEQ ID NO 57
<211> LENGTH: 10
<212> TYPE: PRT
<213> ORGANISM: Artificial Sequence
<220> FEATURE:
<223> OTHER INFORMATION: Synthetic Construct

<400> SEQUENCE: 57

Tyr Val Ser Pro Ala Tyr Ala Tyr Thr Ala
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Synthetic Construct

<400> SEQUENCE: 58

Phe Tyr Val Tyr Ala Ala His Gly Trp Ala Gly Tyr Gly Met
1               5                   10

<210> SEQ ID NO 59
<211> LENGTH: 6
<212> TYPE: PRT
<213> ORGANISM: Artificial Sequence
<220> FEATURE:
<223> OTHER INFORMATION: Synthetic Construct

<400> SEQUENCE: 59

Ala Gly Phe Ala Pro Ile
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic Construct

<400> SEQUENCE: 60

Val Ser Phe Tyr Ser Ile
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Ser Ile Ser Ser Ser Tyr Gly Tyr Thr Tyr
1               5                   10

<210> SEQ ID NO 62
<211> LENGTH: 14
<212> TYPE: PRT
<213> ORGANISM: Artificial Sequence

```
<220> FEATURE:
<223> OTHER INFORMATION: Synthetic Construct

<400> SEQUENCE: 62

Phe Tyr Val Tyr Ala Ser Asn Gly Trp Ala Gly Tyr Gly Met
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Synthetic Construct

<400> SEQUENCE: 63

Ala Gly Phe Ala Pro Val
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic Construct

<400> SEQUENCE: 64

Val Ser Phe Phe Ser Ile
1               5

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct

<400> SEQUENCE: 65

Ser Ile Ser Ser Ser Tyr Gly Tyr Thr Tyr
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetic Construct

<400> SEQUENCE: 66

Phe Tyr Val Tyr Ser Ser His Gly Trp Ala Gly Tyr Gly Met
1               5                   10

<210> SEQ ID NO 67
<211> LENGTH: 6
<212> TYPE: PRT
<213> ORGANISM: Artificial Sequence
<220> FEATURE:
<223> OTHER INFORMATION: Synthetic Construct

<400> SEQUENCE: 67

Ser Ala Tyr Ala Pro Val
1               5

<210> SEQ ID NO 68
<211> LENGTH: 6
<212> TYPE: PRT
<213> ORGANISM: Artificial Sequence
<220> FEATURE:
```

```
<223> OTHER INFORMATION: Synthetic Construct

<400> SEQUENCE: 68

Val Ala Phe Tyr Ser Ile
1               5

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct

<400> SEQUENCE: 69

Phe Ile Ala Pro Ser Tyr Gly Tyr Ser Ala
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Synthetic Construct

<400> SEQUENCE: 70

Phe Phe Val Tyr Ala Ala His Gly Trp Ala Gly Tyr Gly Met
1               5                   10

<210> SEQ ID NO 71
<211> LENGTH: 6
<212> TYPE: PRT
<213> ORGANISM: Artificial Sequence
<220> FEATURE:
<223> OTHER INFORMATION: Synthetic Construct

<400> SEQUENCE: 71

Ala Gly Phe Ala Pro Val
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Construct

<400> SEQUENCE: 72

Ile Ala Phe Phe Ser Ile
1               5

<210> SEQ ID NO 73
<211> LENGTH: 10
<212> TYPE: PRT
<213> ORGANISM: Artificial Sequence
<220> FEATURE:
<223> OTHER INFORMATION: Synthetic Construct

<400> SEQUENCE: 73

Phe Val Ser Pro Ala Tyr Gly Tyr Thr Ala
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic Construct
```

```
<400> SEQUENCE: 74

Phe Tyr Val Tyr Ser Ala Asn Gly Trp Ala Gly Tyr Gly Met
1               5                   10

<210> SEQ ID NO 75
<211> LENGTH: 6
<212> TYPE: PRT
<213> ORGANISM: Artificial Sequence
<220> FEATURE:
<223> OTHER INFORMATION: Synthetic Construct

<400> SEQUENCE: 75

Ser Ala Tyr Ser Pro Val
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic Construct

<400> SEQUENCE: 76

Ile Ala Phe Tyr Ser Ile
1               5

<210> SEQ ID NO 77
<211> LENGTH: 10
<212> TYPE: PRT
<213> ORGANISM: Artificial Sequence
<220> FEATURE:
<223> OTHER INFORMATION: Synthetic Construct

<400> SEQUENCE: 77

Phe Val Ser Pro Ala Tyr Ala Tyr Ser Ala
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Synthetic Construct

<400> SEQUENCE: 78

Phe Tyr Val Tyr Ser Ala Asn Gly Trp Ala Gly Tyr Gly Met
1               5                   10

<210> SEQ ID NO 79
<211> LENGTH: 6
<212> TYPE: PRT
<213> ORGANISM: Artificial Sequence
<220> FEATURE:
<223> OTHER INFORMATION: Synthetic Construct

<400> SEQUENCE: 79

Ala Ala Phe Ala Pro Val
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 80

Phe Ser Ser Ser Ser Ile
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct

<400> SEQUENCE: 81

Tyr Ile Ser Pro Ala Tyr Gly Tyr Ser Ala
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Synthetic Construct

<400> SEQUENCE: 82

Phe Phe Val Tyr Ser Ala Asn Ala Trp Ser Gly Tyr Gly Met
1               5                   10

<210> SEQ ID NO 83
<211> LENGTH: 6
<212> TYPE: PRT
<213> ORGANISM: Artificial Sequence
<220> FEATURE:
<223> OTHER INFORMATION: Synthetic Construct

<400> SEQUENCE: 83

Val Ser Tyr Tyr Ser Ile
1               5

<210> SEQ ID NO 84
<211> LENGTH: 10
<212> TYPE: PRT
<213> ORGANISM: Artificial Sequence
<220> FEATURE:
<223> OTHER INFORMATION: Synthetic Construct

<400> SEQUENCE: 84

Ser Ile Ser Ser Ser Tyr Gly Tyr Thr Ser
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Synthetic Construct

<400> SEQUENCE: 85

Phe Phe Val Tyr Ala Ala His Gly Trp Ala Gly Tyr Gly Met
1               5                   10

<210> SEQ ID NO 86
<211> LENGTH: 6
<212> TYPE: PRT
<213> ORGANISM: Artificial Sequence
<220> FEATURE:
<223> OTHER INFORMATION: Synthetic Construct

<400> SEQUENCE: 86
```

```
Ser Ala Phe Ser Pro Val
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic Construct

<400> SEQUENCE: 87

Ile Ala Phe Phe Ala Val
1               5

<210> SEQ ID NO 88
<211> LENGTH: 10
<212> TYPE: PRT
<213> ORGANISM: Artificial Sequence
<220> FEATURE:
<223> OTHER INFORMATION: Synthetic Construct

<400> SEQUENCE: 88

Phe Val Ser Pro Ser Phe Gly Tyr Ser Ser
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic Construct

<400> SEQUENCE: 89

Phe Tyr Val Tyr Ala Ala His Gly Trp Ala Gly Tyr Gly Met
1               5                   10

<210> SEQ ID NO 90
<211> LENGTH: 6
<212> TYPE: PRT
<213> ORGANISM: Artificial Sequence
<220> FEATURE:
<223> OTHER INFORMATION: Synthetic Construct

<400> SEQUENCE: 90

Ala Ala Phe Ala Pro Val
1               5

<210> SEQ ID NO 91
<211> LENGTH: 6
<212> TYPE: PRT
<213> ORGANISM: Artificial Sequence
<220> FEATURE:
<223> OTHER INFORMATION: Synthetic Construct

<400> SEQUENCE: 91

Val Ala Phe Tyr Ser Ile
1               5

<210> SEQ ID NO 92
<211> LENGTH: 10
<212> TYPE: PRT
<213> ORGANISM: Artificial Sequence
<220> FEATURE:
<223> OTHER INFORMATION: Synthetic Construct

<400> SEQUENCE: 92
```

Tyr Ile Ser Pro Ala Tyr Ala Tyr Ser Ala
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Synthetic Construct

<400> SEQUENCE: 93

Tyr Phe Val Tyr Ala Ser Asn Gly Trp Ala Gly Tyr Gly Met
1               5                   10

<210> SEQ ID NO 94
<211> LENGTH: 6
<212> TYPE: PRT
<213> ORGANISM: Artificial Sequence
<220> FEATURE:
<223> OTHER INFORMATION: Synthetic Construct

<400> SEQUENCE: 94

Ile Ser Tyr Phe Ser Val
1               5

<210> SEQ ID NO 95
<211> LENGTH: 10
<212> TYPE: PRT
<213> ORGANISM: Artificial Sequence
<220> FEATURE:
<223> OTHER INFORMATION: Synthetic Construct

<400> SEQUENCE: 95

Tyr Val Ser Pro Ser Phe Ala Phe Ser Ser
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Synthetic Construct

<400> SEQUENCE: 96

Phe Phe Val Tyr Ser Ala His Gly Trp Ala Gly Tyr Gly Met
1               5                   10

<210> SEQ ID NO 97
<211> LENGTH: 6
<212> TYPE: PRT
<213> ORGANISM: Artificial Sequence
<220> FEATURE:
<223> OTHER INFORMATION: Synthetic Construct

<400> SEQUENCE: 97

Ala Ala Tyr Ala Pro Val
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic Construct

<400> SEQUENCE: 98

Val Ala Phe Tyr Ser Val

```
1               5

<210> SEQ ID NO 99
<211> LENGTH: 10
<212> TYPE: PRT
<213> ORGANISM: Artificial Sequence
<220> FEATURE:
<223> OTHER INFORMATION: Synthetic Construct

<400> SEQUENCE: 99

Ser Ile Ser Ser Ser Tyr Gly Tyr Thr Ala
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Synthetic Construct

<400> SEQUENCE: 100

Phe Tyr Val Tyr Ala Ala His Gly Trp Ala Gly Tyr Gly Met
1               5                   10

<210> SEQ ID NO 101
<211> LENGTH: 6
<212> TYPE: PRT
<213> ORGANISM: Artificial Sequence
<220> FEATURE:
<223> OTHER INFORMATION: Synthetic Construct

<400> SEQUENCE: 101

Ala Ala Tyr Ala Pro Val
1               5

<210> SEQ ID NO 102
<211> LENGTH: 6
<212> TYPE: PRT
<213> ORGANISM: Artificial Sequence
<220> FEATURE:
<223> OTHER INFORMATION: Synthetic Construct

<400> SEQUENCE: 102

Ile Ala Tyr Tyr Ala Val
1               5

<210> SEQ ID NO 103
<211> LENGTH: 10
<212> TYPE: PRT
<213> ORGANISM: Artificial Sequence
<220> FEATURE:
<223> OTHER INFORMATION: Synthetic Construct

<400> SEQUENCE: 103

Phe Val Ser Pro Ala Tyr Gly Phe Thr Ser
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Synthetic Construct

<400> SEQUENCE: 104

Phe Tyr Val Tyr Ser Ser His Gly Trp Ala Gly Phe Gly Met
1               5                   10
```

<210> SEQ ID NO 105
<211> LENGTH: 6
<212> TYPE: PRT
<213> ORGANISM: Artificial Sequence
<220> FEATURE:
<223> OTHER INFORMATION: Synthetic Construct

<400> SEQUENCE: 105

Ala Ala Phe Ala Pro Val
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic Construct

<400> SEQUENCE: 106

Ile Ala Phe Tyr Ala Val
1               5

<210> SEQ ID NO 107
<211> LENGTH: 10
<212> TYPE: PRT
<213> ORGANISM: Artificial Sequence
<220> FEATURE:
<223> OTHER INFORMATION: Synthetic Construct

<400> SEQUENCE: 107

Tyr Val Ala Pro Pro Tyr Ala Tyr Ser Ala
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Synthetic Construct

<400> SEQUENCE: 108

Phe Tyr Val Tyr Ser Ala His Gly Trp Ala Gly Tyr Gly Met
1               5                   10

<210> SEQ ID NO 109
<211> LENGTH: 6
<212> TYPE: PRT
<213> ORGANISM: Artificial Sequence
<220> FEATURE:
<223> OTHER INFORMATION: Synthetic Construct

<400> SEQUENCE: 109

Ala Ala Tyr Ala Pro Val
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic Construct

<400> SEQUENCE: 110

Val Ser Phe Tyr Ser Ile
1               5

<210> SEQ ID NO 111
<211> LENGTH: 10
<212> TYPE: PRT
<213> ORGANISM: Artificial Sequence
<220> FEATURE:
<223> OTHER INFORMATION: Synthetic Construct

<400> SEQUENCE: 111

Tyr Ile Ser Pro Ala Tyr Gly Tyr Thr Ser
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Synthetic Construct

<400> SEQUENCE: 112

Phe Tyr Val Tyr Ser Ala His Gly Trp Ala Gly Tyr Gly Met
1               5                   10

<210> SEQ ID NO 113
<211> LENGTH: 6
<212> TYPE: PRT
<213> ORGANISM: Artificial Sequence
<220> FEATURE:
<223> OTHER INFORMATION: Synthetic Construct

<400> SEQUENCE: 113

Ser Ala Tyr Ser Pro Val
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic Construct

<400> SEQUENCE: 114

Val Ala Tyr Tyr Ser Ile
1               5

<210> SEQ ID NO 115
<211> LENGTH: 10
<212> TYPE: PRT
<213> ORGANISM: Artificial Sequence
<220> FEATURE:
<223> OTHER INFORMATION: Synthetic Construct

<400> SEQUENCE: 115

Tyr Ile Ser Pro Ala Phe Gly Tyr Ser Ser
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Synthetic Construct

<400> SEQUENCE: 116

Phe Tyr Val Tyr Ala Ala Asn Gly Trp Ala Gly Tyr Gly Met
1               5                   10

```
<210> SEQ ID NO 117
<211> LENGTH: 6
<212> TYPE: PRT
<213> ORGANISM: Artificial Sequence
<220> FEATURE:
<223> OTHER INFORMATION: Synthetic Construct

<400> SEQUENCE: 117

Ala Ala Tyr Ala Pro Ile
1               5

<210> SEQ ID NO 118
<211> LENGTH: 6
<212> TYPE: PRT
<213> ORGANISM: Artificial Sequence
<220> FEATURE:
<223> OTHER INFORMATION: Synthetic Construct

<400> SEQUENCE: 118

Val Ala Phe Tyr Ala Val
1               5

<210> SEQ ID NO 119
<211> LENGTH: 10
<212> TYPE: PRT
<213> ORGANISM: Artificial Sequence
<220> FEATURE:
<223> OTHER INFORMATION: Synthetic Construct

<400> SEQUENCE: 119

Ser Ile Ser Ser Ser Tyr Gly Tyr Thr Tyr
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Synthetic Construct

<400> SEQUENCE: 120

Tyr Tyr Val Tyr Ala Ala His Gly Trp Ala Gly Tyr Gly Met
1               5                   10
```